(12) United States Patent
Lambarth

(10) Patent No.: US 12,329,660 B2
(45) Date of Patent: Jun. 17, 2025

(54) BONE PREPARATION DEVICE

(71) Applicant: Stryker Corporation, Kalamazoo, MI (US)

(72) Inventor: Clifford Edwin Lambarth, Portage, MI (US)

(73) Assignee: Stryker Corporation, Portage, MI (US)

(*) Notice: Subject to any disclaimer, the term of this patent is extended or adjusted under 35 U.S.C. 154(b) by 991 days.

(21) Appl. No.: 17/414,606

(22) PCT Filed: Dec. 27, 2019

(86) PCT No.: PCT/US2019/068660
§ 371 (c)(1),
(2) Date: Jun. 16, 2021

(87) PCT Pub. No.: WO2020/139995
PCT Pub. Date: Jul. 2, 2020

(65) Prior Publication Data
US 2022/0047403 A1 Feb. 17, 2022

Related U.S. Application Data

(60) Provisional application No. 62/785,484, filed on Dec. 27, 2018.

(51) Int. Cl.
*A61F 2/46* (2006.01)
*A61B 17/16* (2006.01)
(Continued)

(52) U.S. Cl.
CPC .... *A61F 2/4644* (2013.01); *A61B 2017/1602* (2013.01); *A61B 17/1635* (2013.01);
(Continued)

(58) Field of Classification Search
CPC ........ A61F 2/4644; A61F 2/46; A61F 2/4601; A61F 2/4614; A61F 2/30723;
(Continued)

(56) References Cited

U.S. PATENT DOCUMENTS

| 3,896,522 A | 7/1975 | Lapeyre |
| 4,186,216 A | 1/1980 | Roth |
| (Continued) | | |

FOREIGN PATENT DOCUMENTS

| EP | 1226785 A1 | 7/2002 |
| JP | H07502442 A | 3/1995 |
| (Continued) | | |

OTHER PUBLICATIONS

English language abstract and machine-assisted English translation for EP 1 226 785 A1 extracted from espacenet.com database on Aug. 16, 2021, 8 pages.

(Continued)

*Primary Examiner* — Marcela I. Shirsat
(74) *Attorney, Agent, or Firm* — Howard & Howard Attorneys PLLC

(57) ABSTRACT

An assembly for preparing bone stock includes a shell (52) comprising a base (54) having a support surface (56), and a lid (58). The base and lid have a void space (60) therebetween. A carriage (62) is disposed at least partially within the void space, and moveable across the support surface. The carriage comprises a wall (64), at least a portion (65) of which is resiliently deformable. The wall cooperates with the base to define a preparation chamber (66), and a removal element (68) configured to remove soft tissue from the bone stock is disposed at least partially therein. The resilient portion of the wall is configured to deform when bone stock is positioned between the removal element and the wall. The carriage is configured to receive power from a drive train to actuate movement of the carriage across the support surface, and the removal element is also configured to receive power from the drive train.

22 Claims, 35 Drawing Sheets

(51) Int. Cl.
*A61F 2/28* (2006.01)
*B02C 19/00* (2006.01)
*B02C 19/20* (2006.01)

(52) U.S. Cl.
CPC ....... *A61B 17/1642* (2013.01); *A61B 17/1657* (2013.01); *A61F 2002/2839* (2013.01); *A61F 2002/4645* (2013.01); *A61F 2002/4648* (2013.01); *A61F 2002/4649* (2013.01); *A61F 2310/00359* (2013.01); *B02C 19/0056* (2013.01); *B02C 19/20* (2013.01)

(58) Field of Classification Search
CPC ...... A61F 2002/4645; A61F 2002/4646; A61F 2002/4649; A61F 2002/2835; A61F 2002/2839; A61F 2002/4648; A61F 2002/30759; A61F 2002/30762; A61F 2002/30764; A61F 2310/00359; A61B 17/1635; A61B 17/1637; A61B 17/1642; A61B 17/1657; A61B 17/1662; A61B 17/16; A61B 17/320016; A61B 2017/1602; B02C 19/0056; B02C 19/20; B02C 18/083; A47J 42/56; A47J 43/075; B23Q 11/0825
USPC ...... 606/79, 53, 80, 85, 86 R, 909, 167–189
See application file for complete search history.

(56) References Cited

U.S. PATENT DOCUMENTS

| | | | |
|---|---|---|---|
| 4,629,131 A | 12/1986 | Podell | |
| 4,741,482 A | 5/1988 | Coggiola et al. | |
| 4,767,069 A | 8/1988 | Kim | |
| 5,333,626 A | 8/1994 | Morse et al. | |
| 5,607,269 A | 3/1997 | Dowd et al. | |
| 5,836,528 A | 11/1998 | Hilgarth | |
| 5,906,322 A | 5/1999 | Hama | |
| 5,977,432 A | 11/1999 | Wolfinbarger, Jr. et al. | |
| 6,017,354 A | 1/2000 | Culp et al. | |
| 6,217,614 B1 | 4/2001 | Fages et al. | |
| 6,287,312 B1 | 9/2001 | Clokie et al. | |
| 6,755,365 B1 | 6/2004 | Meredith | |
| 6,824,087 B2 | 11/2004 | McPherson et al. | |
| 7,028,930 B2 | 4/2006 | Carnevale | |
| 7,029,387 B2 | 4/2006 | van den Nieuwelaar et al. | |
| 7,063,283 B2 | 6/2006 | Wanat | |
| 7,131,605 B2 | 11/2006 | McPherson et al. | |
| 7,422,582 B2 | 9/2008 | Malackowski et al. | |
| 7,520,453 B2 | 4/2009 | Clapp et al. | |
| 7,588,202 B2 | 9/2009 | Rasekhi | |
| 8,002,774 B2 | 8/2011 | Burmeister, III et al. | |
| 8,512,342 B2 | 8/2013 | Meredith | |
| 8,622,953 B2 | 1/2014 | Hynes et al. | |
| 8,672,942 B2 | 3/2014 | Chamberlin et al. | |
| 8,740,114 B2 | 6/2014 | Koltz et al. | |
| 9,370,436 B2 | 6/2016 | Stratton | |
| 9,687,361 B2 | 6/2017 | Diehl et al. | |
| 10,034,673 B2 | 7/2018 | Lynch et al. | |
| 10,045,863 B2 | 8/2018 | Stratton et al. | |
| 10,258,201 B1 | 4/2019 | Rasekhi | |
| 10,588,757 B2 | 3/2020 | Stratton et al. | |
| 10,821,006 B2 | 11/2020 | Horton, IV et al. | |
| 10,828,048 B2 | 11/2020 | Lynch et al. | |
| 2002/0176320 A1 | 11/2002 | Wulf et al. | |
| 2004/0155132 A1 | 8/2004 | McPherson et al. | |
| 2006/0138260 A1 | 6/2006 | Hay et al. | |
| 2006/0261685 A1 | 11/2006 | Schindler et al. | |
| 2007/0164137 A1 | 7/2007 | Rasekhi | |
| 2008/0274682 A1 | 11/2008 | Iversen | |
| 2009/0118713 A1 | 5/2009 | Munson | |
| 2009/0118735 A1 | 5/2009 | Burmeister, III et al. | |
| 2010/0291506 A1 | 11/2010 | Olsson et al. | |
| 2010/0308142 A1 | 12/2010 | Krasznai et al. | |
| 2011/0166503 A1 | 7/2011 | Koltz et al. | |
| 2011/0248108 A1 | 10/2011 | Carriere | |
| 2012/0310243 A1 | 12/2012 | Stratton et al. | |
| 2013/0001340 A1 | 1/2013 | Garcia et al. | |
| 2014/0263778 A1 | 9/2014 | Koltz et al. | |
| 2014/0303623 A1 | 10/2014 | Diehl et al. | |
| 2014/0322411 A1 | 10/2014 | Segurola et al. | |
| 2016/0278942 A1 | 9/2016 | Stratton et al. | |
| 2016/0309960 A1 | 10/2016 | Kolar et al. | |
| 2018/0020875 A1 | 1/2018 | Kolar et al. | |
| 2018/0078094 A1 | 3/2018 | Haney et al. | |
| 2019/0000275 A1 | 1/2019 | Sapire | |
| 2019/0029846 A1* | 1/2019 | Horton, IV | ........... A61F 2/4644 |

FOREIGN PATENT DOCUMENTS

| | | | |
|---|---|---|---|
| JP | 2004509631 A | 4/2004 | |
| JP | 2008534191 A | 8/2008 | |
| WO | 9312731 A1 | 7/1993 | |
| WO | 03017913 A1 | 3/2003 | |
| WO | 03082159 A1 | 10/2003 | |
| WO | 2006105950 A2 | 10/2006 | |
| WO | 2009061728 A1 | 5/2009 | |
| WO | 2011057088 A1 | 5/2011 | |
| WO | 20170019827 A2 | 2/2017 | |

OTHER PUBLICATIONS

English language abstract and machine-assisted English translation for JP 2008-534191 extracted from espacenet.com database on Nov. 15, 2017, 24 pages.
English language abstract and machine-assisted English translation for WO 2006/105950 A2 extracted from espacenet.com database on Aug. 16, 2021, 17 pages.
English language abstract for JP 2004-509631 extracted from espacenet.com database on Nov. 15, 2017, 2 pages.
English language abstract for JPH 07-502442 extracted from espacenet.com database on Aug. 16, 2021, 1 page.
International Search Report for Application No. PCT/US2010/055646 dated Feb. 28, 2011, 4 pages.
International Search Report for Application No. PCT/US2012/072160 dated Jul. 10, 2013, 3 pages.
International Search Report for Application No. PCT/US2016/044386 dated Jan. 20, 2017, 4 pages.
International Search Report for Application No. PCT/US2019/068660 dated Apr. 29, 2020, 5 pages.
Marshall Excelsior Company, "LP Gas & Anhydrous Ammonia (NH3) Equipment Catalog", 2020-2021, 228 pages.

* cited by examiner

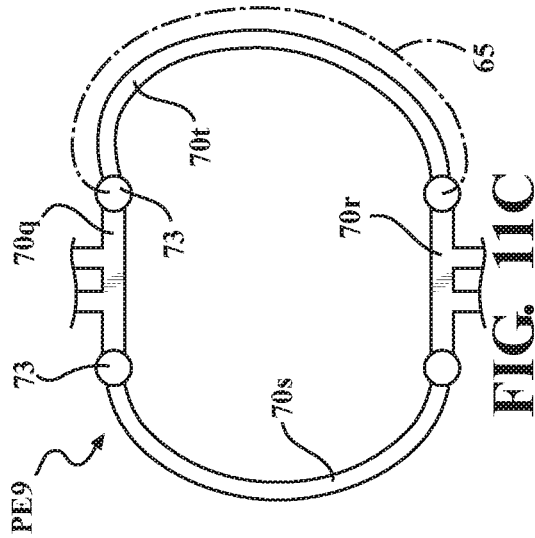
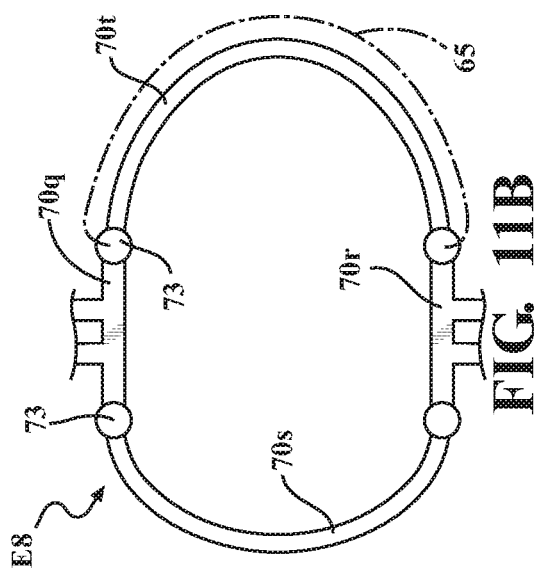
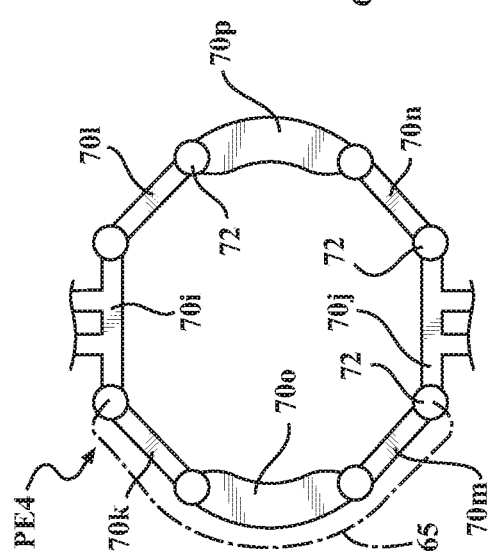
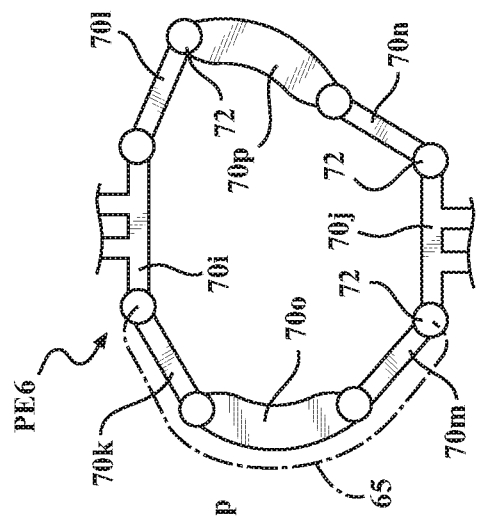
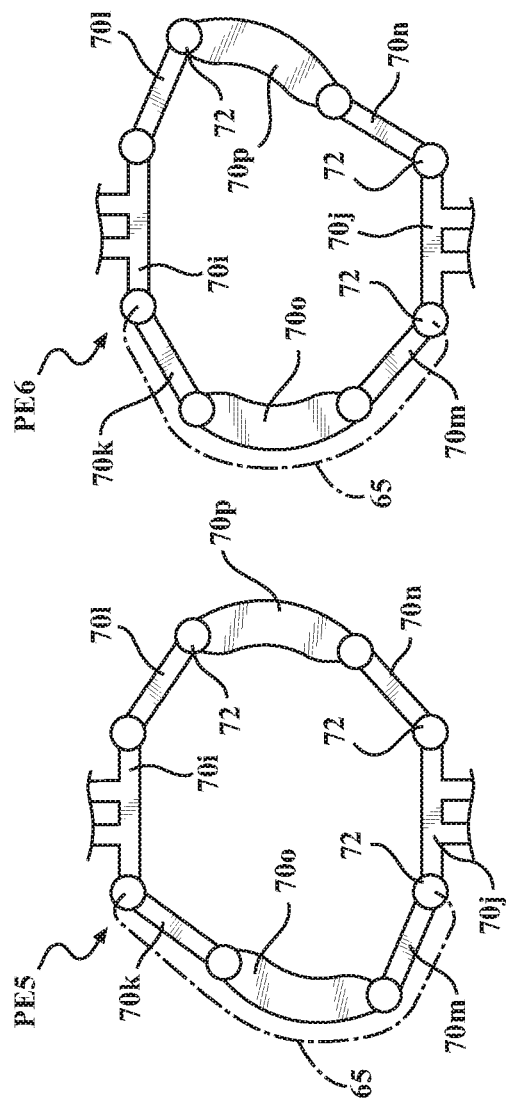
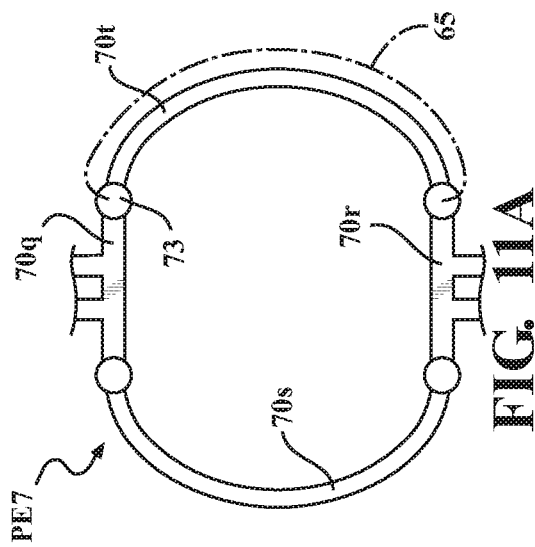

BONE PREPARATION DEVICE

CROSS-REFERENCE TO RELATED APPLICATIONS

The subject application is the National Stage of International Application No. PCT/US2019/068660, filed on Dec. 27, 2019, which claims priority to and all of the benefits of U.S. Provisional Patent Application No. 62/785,484, filed on Dec. 27, 2018, the disclosures of which are hereby incorporated by reference.

FIELD OF THE DISCLOSURE

This disclosure relates generally to an assembly for preparing bone stock for use in surgical procedures.

BACKGROUND OF THE DISCLOSURE

Conventional medical and surgical procedures routinely involve the use of bone fragments, often collectively referred to as bone graft, to bridge gaps between bone segments and provide a natural foundation for bone growth.

For example, spinal procedures (e.g. discectomy) utilize bone graft. In such procedures, bone graft is inserted around implanted rods, which hold adjacent vertebrae in alignment. The bone graft serves as a lattice upon which tissues forming the vertebrae grow to form a foundation of bone around the rods. This foundation distributes the load imposed on the rods. In addition, bone graft may also be placed in the intervertebral disc space or into a cage positioned in the intervertebral disc space.

As another example, orthopedic surgical procedures such as joint reconstruction and revision procedures and maxillofacial procedures utilize bone graft. In such procedures, bone graft is used as a filler and/or growth formation lattice in these procedures because the proteins from which the bone is formed serve as make-up material from which the blast cells of the adjacent living bone cells form new bone.

The ideal source of bone stock for bone fragments is the patient into whom the bone fragments are to be packed. This is because the patient's own bone is less likely than donor bone to be rejected by the patient's immune system. Accordingly, in a procedure in which bone chips are required, bone stock is often harvested from one of the patient's bones that may afford to lose a small section of bone, typically between 0.25 and 3 cubic centimeters. Bone stock that is removed from the patient for transplant into another part of the patient is referred to as autograft bone stock.

Converting bone stock into bone fragments is typically a two-part process. In the first part of the process, the harvested bone is prepared for milling and use by removing the ligaments and other soft tissue that is not suitable for forming bone fragments. The prepared bone is then milled into bone fragments, which are used as bone graft.

In a typical bone preparing process, prior to milling the bone stock, surgical personnel manually remove ligaments and other soft tissue from the bone stock. Presently, surgical personnel perform this manual process using curettes and/or rongeurs. It may take 15 minutes or more for surgical personnel to perform this task. Moreover, in such typical processes, the surgical personnel may need to firmly grasp the bone. Exerting such force on the bone may cause tearing of the gloves worn by the surgical personnel. Furthermore, the sharp cutting tools being used by the surgical personnel could cut or tear through the gloves. Such cutting or tearing through the gloves could result in the possibility that skin of the surgical personnel may come into direct contact with the bone. This contact may result in contamination of the bone.

In mechanized bone preparing processes, the preparing process may yield inconsistent results due to variations in the consistency and the homogeneity of the bone stock. That is, the bone stock may agglutinate and/or agglomerate within bone preparing devices and thus yield bone stock that still has ligaments and other soft tissue adhered thereto.

Accordingly, there is a need in the art for assemblies that consistently remove soft tissue from bone stock in a sterile and efficient manner.

BRIEF DESCRIPTION OF THE DRAWINGS

The disclosure is pointed out with particularity in the claims. The above and further features and benefits of this disclosure are understood from the following Detailed Description taken in conjunction with the accompanying drawings in which:

FIGS. 10A-C are isolated top views of an exemplary resiliently deformable wall arranged in three exemplary wall profiles $P_{E4}$, $P_{E5}$, and $P_{E6}$.

FIGS. 11A-C are isolated top views of, yet another exemplary resiliently deformable wall arranged in three exemplary wall profiles $P_{E7}$, $P_{E8}$, and $P_{E9}$.

FIGS. 1-42 are exemplary in nature, are not necessarily drawn to scale, and are thus not intended to represent the relative sizes of the various components of the system described herein.

DETAILED DESCRIPTION

Figure 1:
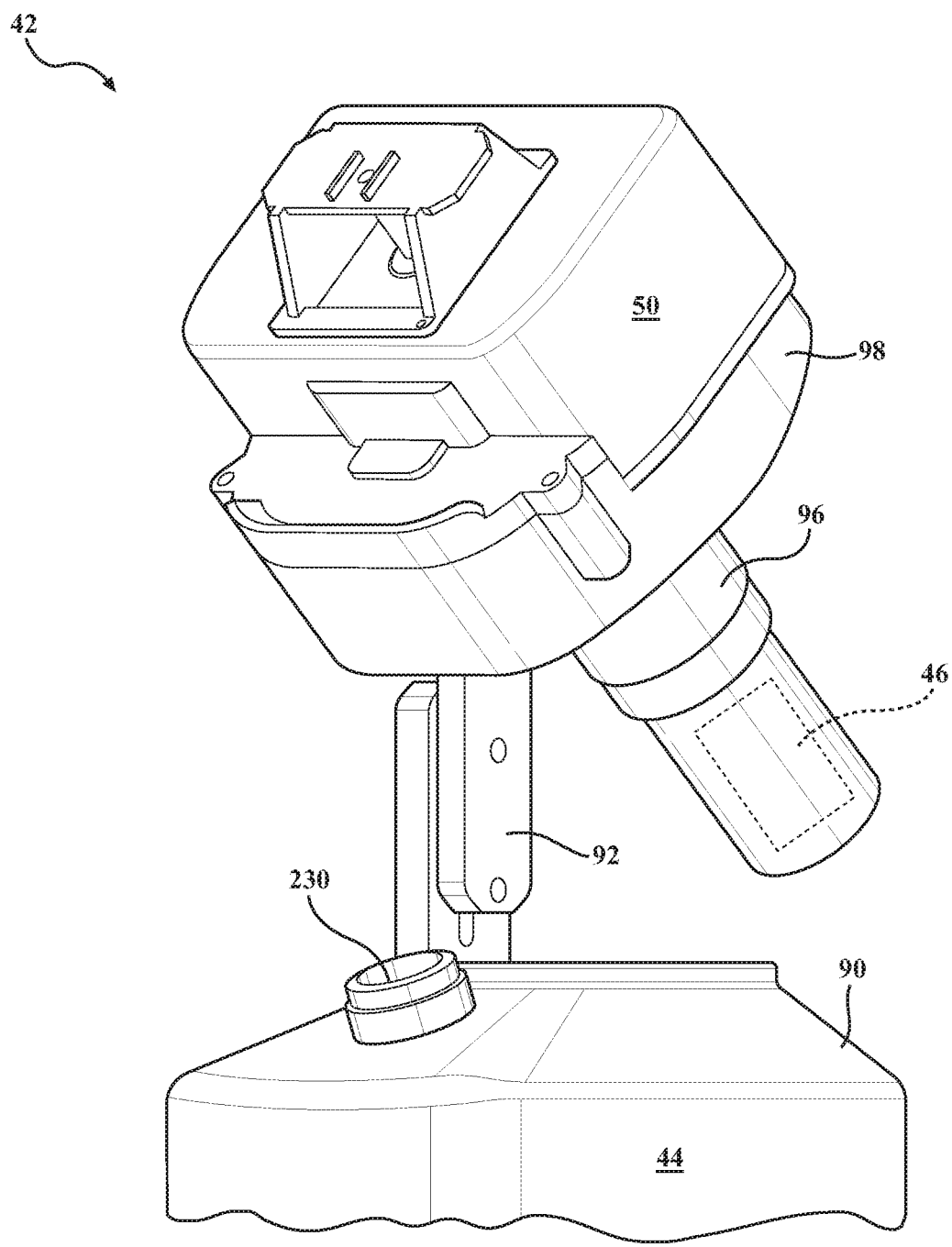
FIG. 1 is a perspective view of a modular system for preparing bone stock with a preparation module attached to a base module.

Referring to the Figures, an assembly for preparing bone stock is disclosed. The assembly for preparing bone stock may be included in a modular system 42 ("system 42") for preparing (e.g. cleaning) and optionally milling bone stock. An example of the system 42 is illustrated in FIGS. 1-28. The system 42 includes a base module 44. Internal to the base module 44 is a motor 46 and a drive train. The system 42 includes a preparation module 50, which is removably attachable to the base module 44. The preparation module 50 at least partially includes the bone preparing assembly 40.

Figure 2:
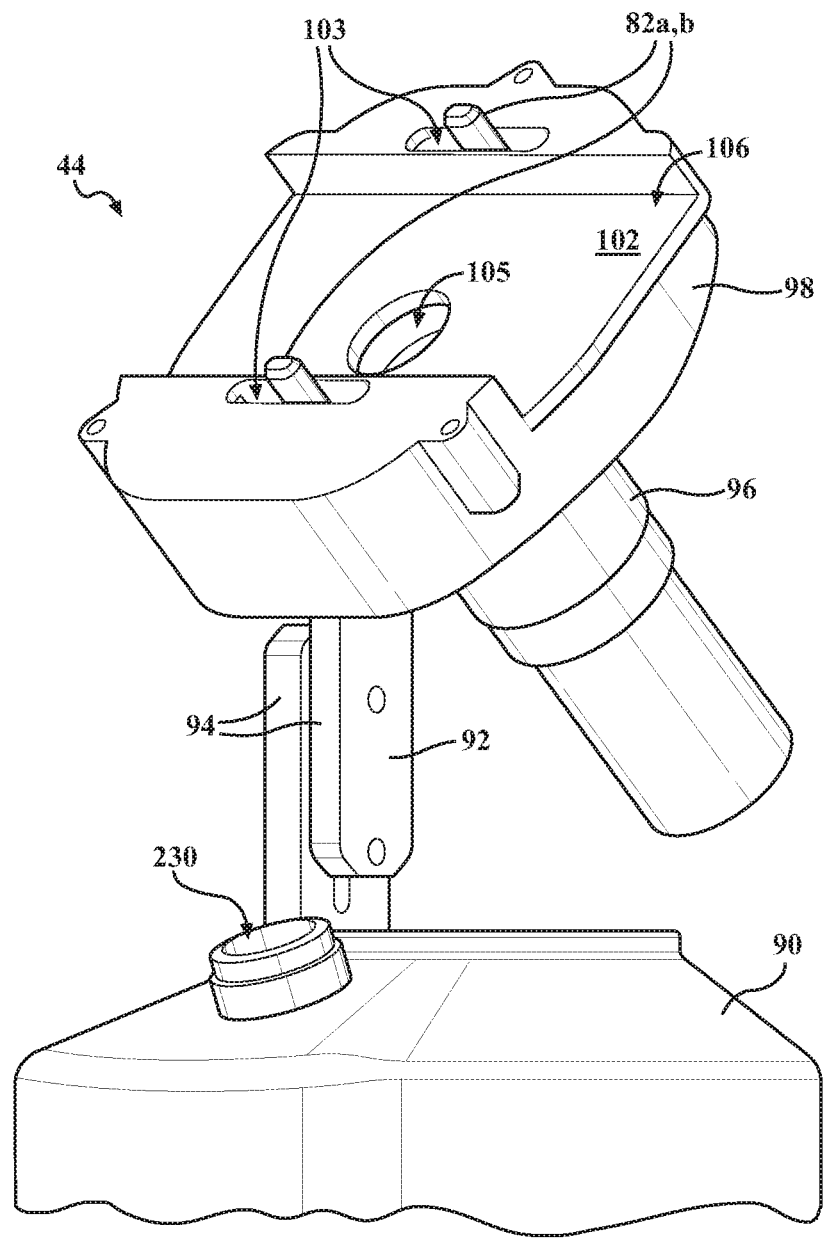
FIG. 2 is a perspective view of the base module of the system of FIG. 1 with the preparation module detached therefrom.
Figure 3:
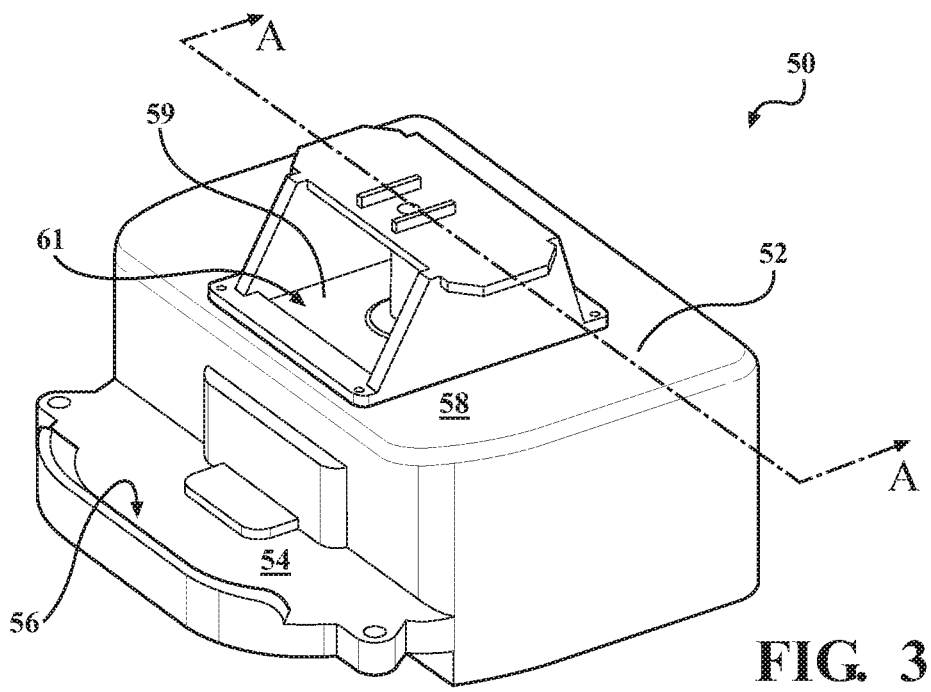
FIG. 3 is a top perspective view of the detached preparation module of the system of FIG. 1.
Figure 4:
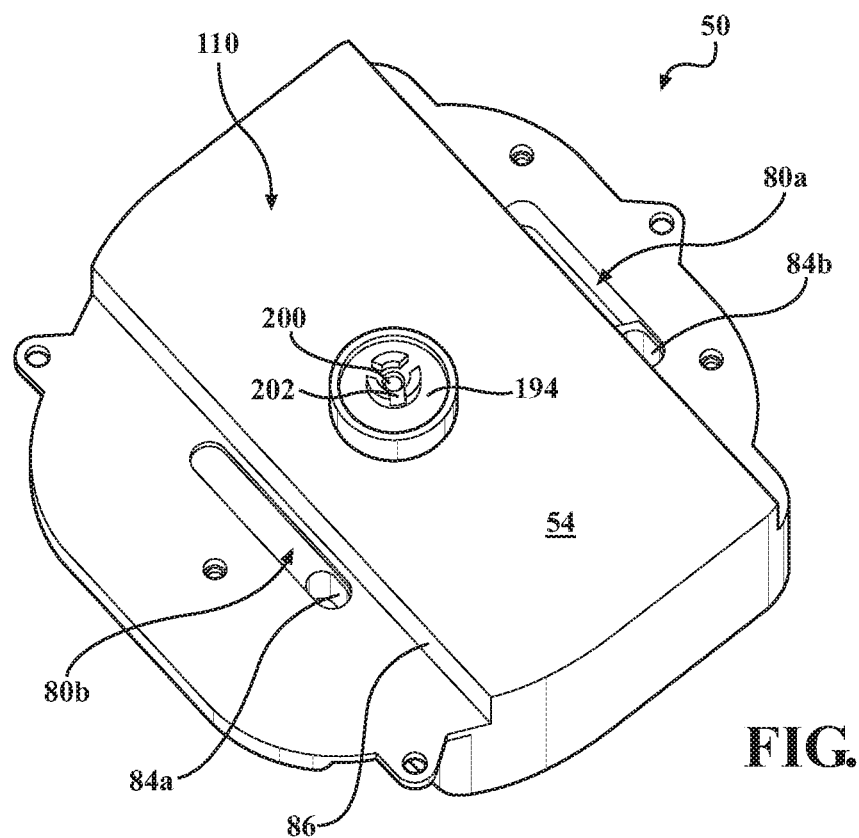
FIG. 4 is a bottom perspective view of the detached preparation module of the system of FIG. 1.

FIG. 1 is a perspective view of the base module 44 of the system 42 of FIG. 1 with the preparation module 50 attached to the base module 44. FIG. 2 is a perspective view of the base module 44 of the system 42 of FIG. 1 with the preparation module 50 detached, while FIGS. 3 and 4 are top and bottom perspective views of the preparation module 50 of the system 42 shown in FIG. 2. In the example illustrated in FIG. 1, the base module 44 is reusable, and the preparation module 50 is disposable. As such, the preparation module 50 may thus be discarded after use, and an unused preparation module 50 may be attached for further use. Of course, other examples of the system 42 include the preparation module 50 that is reusable and may be autoclaved.

Figure 5:
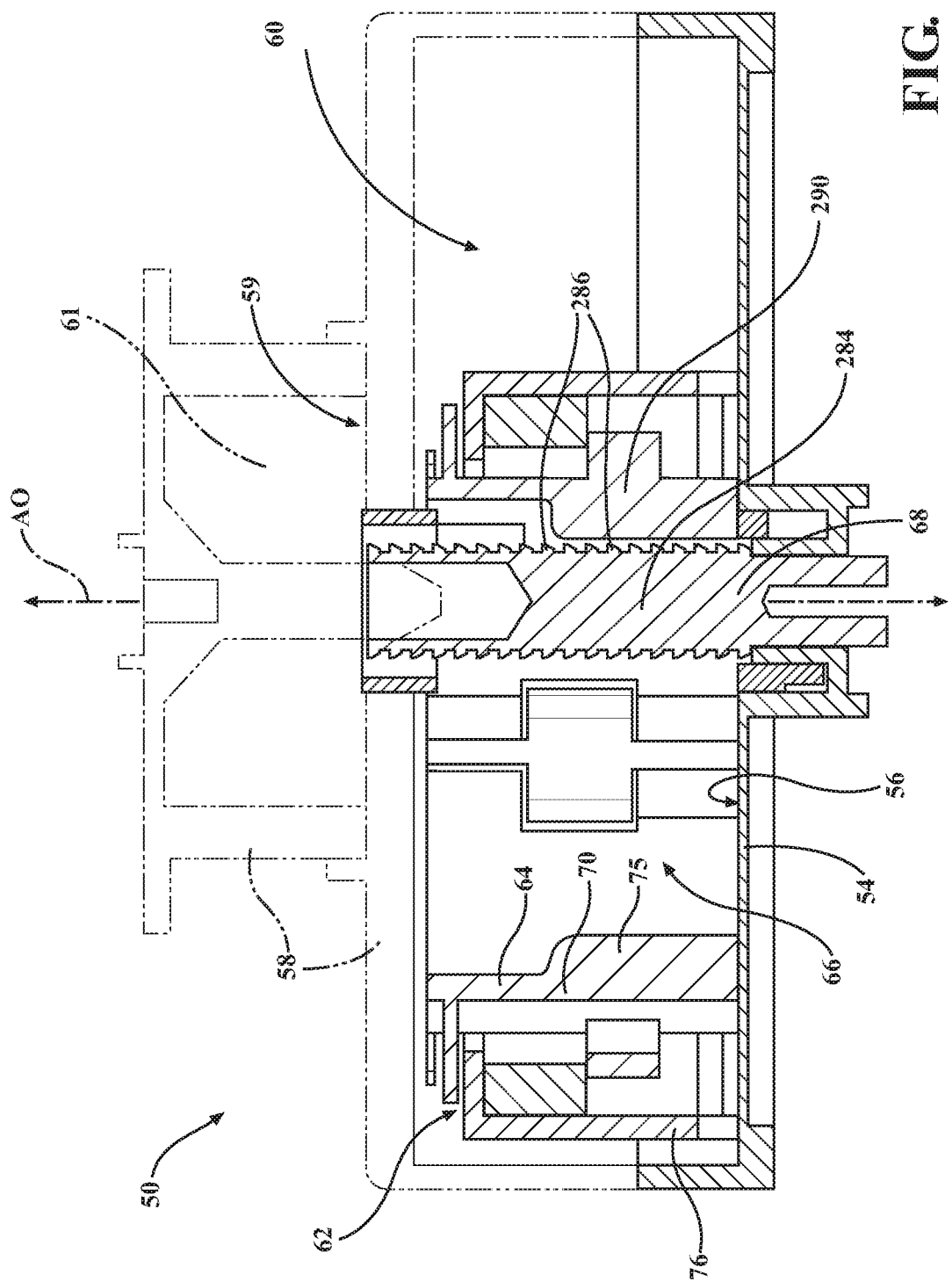
FIG. 5 is a cross-sectional view of the preparation module of FIG. 3.
Figure 6:
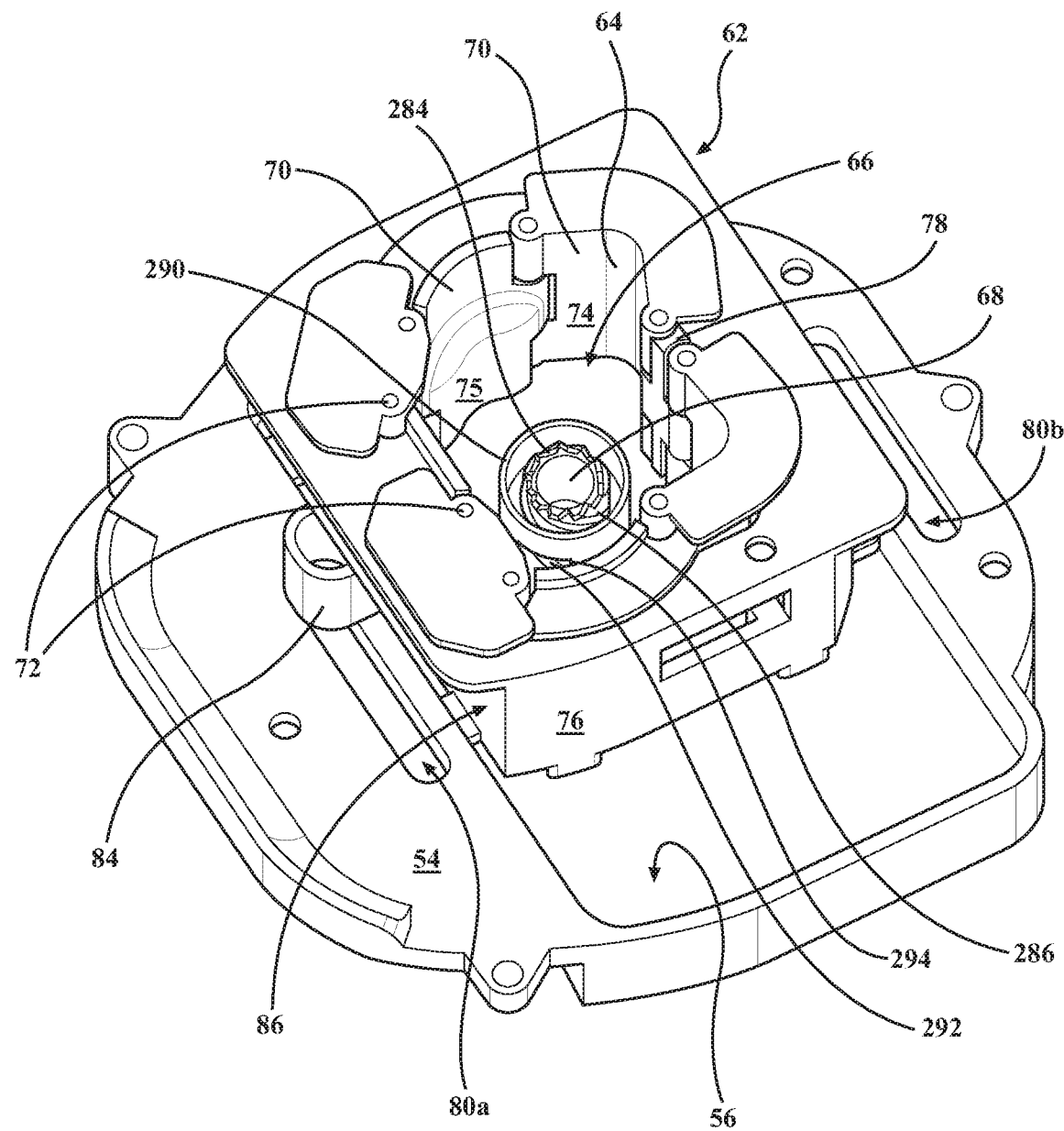
FIG. 6 is an isolated top perspective view of the preparation module of the system of FIG. 1 including a carriage moveably disposed on a support surface partially defining a preparation chamber with a removal element therein.

Referring now to FIG. 6, the base module 44 includes features that facilitate the releasable coupling of the preparation module 50 to the base module 44 which drive a carriage 62 and a removal element 68. In examples of this disclosure, the preparation module 50 (see FIG. 5) is formed with features that releasably couple the carriage 62 and the removal element 68 to the drive train, while also releasably coupling the preparation module 50 to the base module 44. It is to be appreciated that the drive train generally describes all elements that power movement of the carriage 62 and the removal element 68 and include sub-assemblies referenced herein including a cam assembly and a gear train. In the example of the system 42 is illustrated in FIGS. 1-28 the cam assembly and the gear train are in the base module 44 to reduce the cost of the preparation module 50, which is designed to be disposable.

Referring now to FIGS. 3-7, the preparation module 50 includes a shell 52 comprising a base 54 having a support surface 56, and a lid 58. In FIG. 3, a top perspective view of the detached preparation module 50 is illustrated. In FIG. 4, a bottom perspective view of the preparation module 50 is illustrated. In FIG. 5, a cross-sectional view of the preparation module 50 of FIG. 3 is illustrated.

Still referring to the preparation module 50, the base 54 and the lid 58 collectively define a void space 60 therebetween (as is illustrated in FIG. 5). The carriage 62 is disposed at least partially within the void space 60 and moveable across the support surface 56. The carriage 62 comprises a wall 64, at least a portion 65 of which is resiliently deformable. The wall 64 cooperates with the base 54 to define a preparation chamber 66, and the removal element 68 is disposed at least partially in the preparation chamber 66. The resiliently deformable portion 65 of the wall 64 is configured to deform when a suitable amount of bone stock is positioned between the removal element 68 and the wall 64.

The carriage 62 is configured to receive power from the drive train to actuate movement of the carriage 62 across the support surface 56, and the removal element 68 is also configured to receive power from the drive train. This movement is described in detain below and illustrated in FIGS. 23-25.

FIG. 6 is a top perspective view of the preparation module 50 with its lid 58 removed. In FIG. 6, the removal element 68 disposed at least partially in the preparation chamber 66 is illustrated. The removal element 68 is selected from a rotating brush, a rotating grater, a rotating fluted screw 284, or combinations thereof. Further, other exemplary removal elements are illustrated and described in U.S. Pat. Nos. 8,672,942 and 9,687,361, the contents of which are hereby incorporated by reference, both of which are directed towards electrically operated bone preparation and milling systems.

In FIG. 6, the removal element 68 includes the fluted screw 284 rotationally mounted within the preparation chamber 66 and a shaving tube 290 disposed about the fluted screw 284 statically or dynamically mounted to the base 54. The removal element 68 is illustrated located at least partially within the preparation chamber 66. The removal element 68 is supported to rotate about an operational axis AO. The removal element 68 illustrated includes the fluted screw 284 with helical flutes 286 having cutting edges 288. During operation of the system 42, the fluted screw 284 rotates about the operational axis AO and the cutting edges 288 prepare bone stock in the preparation chamber by cutting soft tissue from the bone stock. As such, the removal element 68 can also be referred to as a cleaning element. In some examples, the fluted screw 284 rotates in a first rotational direction $R_1$ (clockwise as viewed from above).

The shaving tube 290 extends coaxially about the fluted screw 284, as illustrated in FIG. 6. The shaving tube 290 defines at least one cutter window 292 through which tissue attached to the bone stock is received for engagement by the fluted screw 284. The cutter window 292 is bounded by shaver edges 294. The shaver edges 294 are sharp to cut soft tissue caught between the cutting edges 288 of the helical flutes 286 and the shaver edges 294 of the cutter window 292 when the fluted screw 284 rotates relative to the shaving tube 290. The shaver edges 294 also act as impingement structures against which soft tissue abuts and is temporarily held to facilitate cutting by the fluted screw 284 of the removal element 68.

In some examples, the shaving tube 290 is configured to rotate about the operational axis AO. Because of the helical geometry of the flutes 286, as the fluted screw 284 rotates, soft tissue is cut and augured axially upwardly along fluted screw 284 between the fluted screw 284 and the shaving tube 290 and is expelled out of a top end of the shaving tube 290. In essence, the fluted screw 284 acts as a screw conveyor. The space between the fluted screw 284 and the shaving tube 290 is a debris passage through which the cut soft tissue is augured and ultimately expelled.

The lid 58, illustrated in FIG. 3, is disposed about the shaving tube 290 near the top end, Referring now to FIG. 5, the lid 58 defines a collecting surface 59 onto which the tissue that exits from the top end of the shaving tube 290 may fall and collect within a collection chamber 61, which is also defined within the lid 58. The collecting surface 559 is spaced slightly below the top end of the shaving tube 290 to act as a soft tissue catch.

Figure 7:
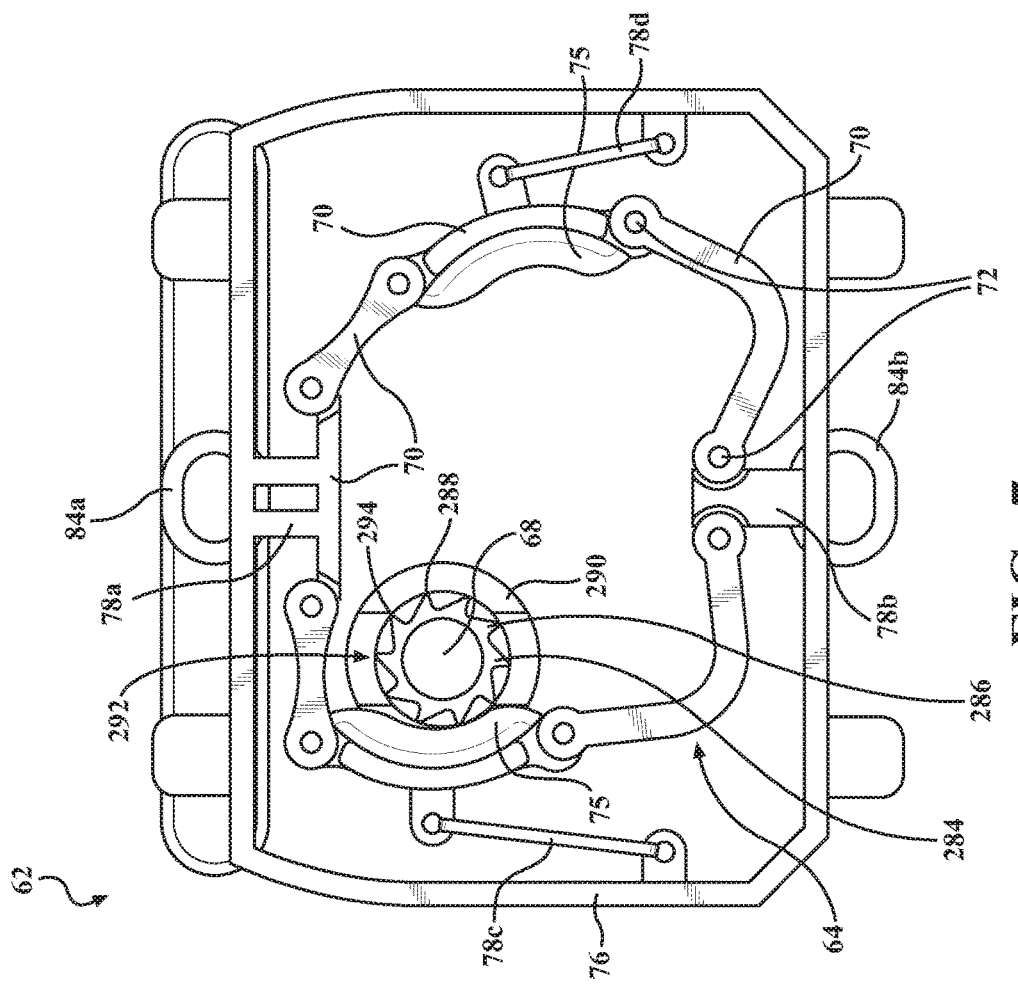
FIG. 7 is an isolated top view of the carriage of the system of FIG. 6.

The lid 58 is removed in FIG. 6. As such, the wall 64, which surrounds the removal element 68, is illustrated. The wall 64 of FIG. 6 includes a plurality of wall segments 70, which are connected. In the example set forth in FIG. 5, the plurality of wall segments 70 are moveably connected via a plurality of hinges 72. The wall segments 70 have an interior surface 74, which can be planer, curved, or profiled. In many examples, such as the example of FIG. 6, the wall 64 includes wall segments 70 with different profiles (e.g. some segments have flat, some have curved, and some have profiled inner surfaces 74. Two of the wall segments 70 have catch pads 75 disposed on their interior surface 74. As is best illustrated in FIG. 7, some of the wall segments 70 are fixed relative to the carriage housing 76 while some of the wall segments 70 are moveable relative to the carriage housing 76. The wall segments 70 of this example are configured to articulate and may be referred to as articulating wall segments 70. To this end, the wall 64 can be described as an articulating wall. Some of the wall segments 70 of this example, may also be referred to as resiliently deformable (the three wall segments 70 on each end of the wall 64). In other words, two portions of the wall 64 of this example are resiliently deformable. Various exemplary configurations of the wall 64 are set forth in FIGS. 6-11.

In FIG. 6, the carriage 62 includes a carriage housing 76 that is spaced outwardly of and coupled to the wall 64. The carriage housing 76 extends at least partially around an outer perimeter of the wall 64 and is moveable across the support surface 56 of the base 54. The carriage housing 76 typically has a fixed profile and is not deformable. The carriage housing 76 functions as a rigid frame to which the wall 64 that is resiliently deformable is coupled. As is illustrated in FIG. 7, the wall 64 may be coupled to the carriage housing 76 with one or more rigid anchors 78*a* and 78*b* and/or one or more resilient anchors 78*c* and 78*d*.

In various examples contemplated herein, the one or more resilient anchors comprise an elastomeric material, e.g. rubber, such that movement of the carriage housing 76 results in the subsequent movement of the wall 64 as bone stock is pinched between the wall 64 and the removal element 68 to allow additional movement of the wall 64. In turn, the local movement or deformation of the wall 64 effectively moves the bone stock within the preparation chamber to ensure optimum preparation, i.e., removal of ligaments and other soft tissue from the bone stock. In some examples, the resilient anchor comprises a spring. In other examples, the resilient anchor comprises an elastomeric or rubber member.

The carriage 62 comprises the wall 64, at least a portion 65 of which is resiliently deformable. The wall 64 cooperates with the base 54 to define the preparation chamber 66, and the removal element 68 is disposed at least partially in the preparation chamber 66. The resiliently deformable portion 65 of the wall 64 is configured to deform when a suitable amount of bone stock is positioned between the removal element 68 and the wall 64.

In examples where the wall 64 is described as resilient, the wall 64 may be defined as being configured to change or return to its original position or profile after being moved, bent, compressed, or stretched. The wall 64 is resilient by virtue of one of the segments 70 being biased (coupled to a resilient anchor, e.g. 78*c* and 78*d* or coupled with resilient joint element, e.g. 70*s* and 70*t*). In the example of FIGS. 6, 7, 8A-C, 9, and 10A-C the wall 64 can be described as resilient because of the resilient anchors 78*c* and 78*d*. In the Example of FIGS. 11A-C, the wall 64 can be described as resilient because of its elastomeric wall segments 70*s* and 70*t*.

In the example of the example of FIGS. 7 and 8A-C the wall 64 is described as articulating, the wall 64 may be described as being configured, e.g. including segments 70 coupled by joints 72, to change its original position or profile. As is illustrated in the example of FIGS. 7 and 8A-C the wall 64 may be described as resilient because of the resilient anchors 78*c*, 78*d* and the plurality of segments 70, which are coupled via hinges 72.

Of course, the wall 64 can be described as both articulating and resilient. Further, it should be appreciated that wall 64 can include or more segments 70 that are rigid (not elastomeric) that are hinged that can be described as resilient. In such embodiments, the wall 64, typically anchored to the carriage 62, can be described as resilient because the movement of the carriage 62 with the wall 64 being anchored thereto allows the wall 72 to able to deform and revert back into shape during use.

The wall 64 may comprise 2, 3, 4, 5, 6, 7, 8, or more segments 70, which may be hinged or, in some examples, the segments 70 are connected to one another with an elastomeric bridge. In some examples, one or more segments 70 are elastomeric, which eliminates the need for a movable coupling configuration, e.g. hinges, and allows for a fixed coupling configuration, e.g. mechanically connected, bonded or welded, of one segment to another. In some examples, the wall 64 includes at least six hinged wall segments 70 and is connected to the carriage housing 76 with at least static two anchors 78. In other examples, the wall 64 comprises a single elastomeric wall segment 70. It is to be appreciated each of the one or more wall segments 70 that form the wall 64 may comprise rigid (e.g. plastic or metal) or an elastomeric material (e.g. silicone rubber). Further, the one or more wall segments 70 may be connected via a plurality of fixed couplings (e.g. fixed mechanically or adhesively) or moveable couplings (e.g. hinges 72, joints, or elastomeric bridges).

Referring now to FIG. 7, an isolated top view of the carriage 62 of the system 42 for preparing bone stock is illustrated. The carriage 62 illustrated in FIG. 7 includes the carriage housing 76, which is positioned radially outward of the outer perimeter of the wall 64. The carriage housing 76 has a fixed inner profile (generally rectangular as illustrated) and is not deformable, while the wall 64 anchored thereto is resiliently deformable. In this example, the wall 64 includes two fixed wall segments 70a, 70b which are connected to the carriage housing 76 with fixed anchors 78. Wall segment 70a, which is a fixed wall segment, is rigidly connected to the carriage housing 76 with the anchor 78a including two pillars. Wall segment 70b, which is also a fixed wall segment, is also rigidly connected to the carriage housing 76 with the anchor 78b including a single pillar.

Of course, the wall 64 of FIG. 7 also includes six wall segments 70c-h that are not directly and rigidly anchored to the carriage housing 76. Two wall segments 70c, 70d may be straight, and present a flat inner surface. Two wall segments 70g, 70h are curved, and present a curved inner surface. Two wall segments 70e, 70f are profiled to "catch" the bone stock and facilitate contact with the removal element 68 within the preparation chamber 66. These two profiled wall segments 70e, 70f each include the catch pad 75 disposed on the interior surface 74. The catch pad 75 catches and pushes the bone stock into the removal element 68, cause deformation of the wall 64, and facilitate thorough preparation of the bone stock. These two profiled wall segments 70e, 70f are resiliently connected to the carriage housing 76 with the resilient anchors 78c, 78d that comprise an elastomeric material.

Figure 8A:
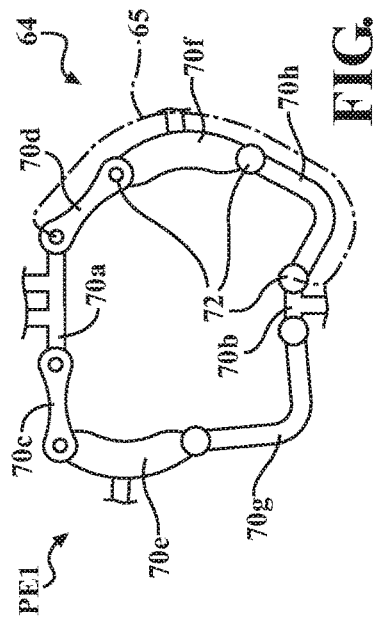
FIGS. 8A-C are isolated top views of an exemplary resiliently deformable wall arranged in three exemplary wall profiles $P_{E1}$, $P_{E2}$, and $P_{E3}$.
Figure 8B:
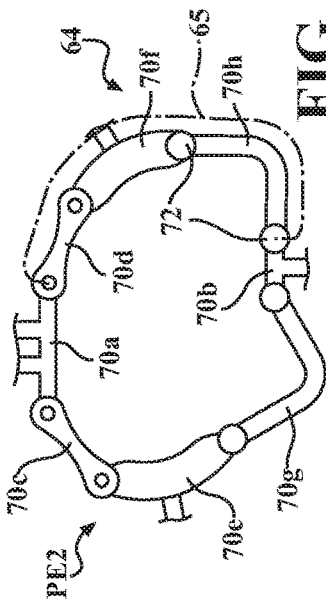
Figure 8C:
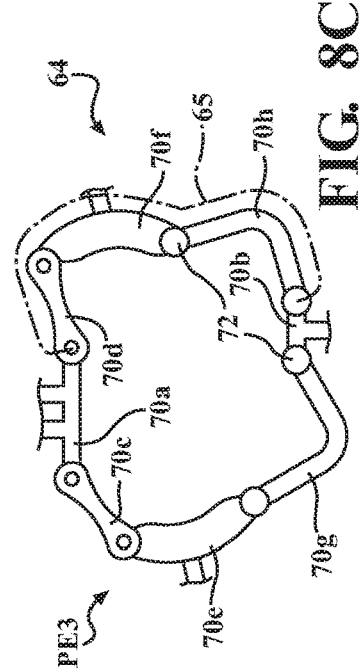

FIGS. 8A-C is are isolated top views of the wall 64 of FIG. 6. FIG. 8A-C illustrate the movement of the eight wall segments 70a-h, all of which are moveably connected to one another via hinges 72. As is illustrated in example wall profiles $P_{E1}$, $P_{E2}$, and $P_{E3}$ of FIGS. 8A-C, the wall 64 is designed to deform. That is, the inner profile of the wall (which partially defines the preparation chamber 66), may change as the carriage 62 moves across the support surface 56. The changing profile of the wall 64 is illustrated in the exemplary wall profiles of $P_{E1}$, $P_{E2}$, and $P_{E3}$. Of course, as the profile of the wall 64 changes, so does the profile of a volume of the preparation chamber 66. A changing inner profile of the wall 64 facilitates movement of the bone stock within the preparation chamber 66 and ensures and removal of ligaments and other soft tissue from the bone stock. It should be appreciated that an inner profile of the wall 64 changes because the wall 64 includes one or more articulating portions 65. In this example, the wall 64 includes two resilient, articulating wall portions 65, only one of which is numbered.

Figure 9:
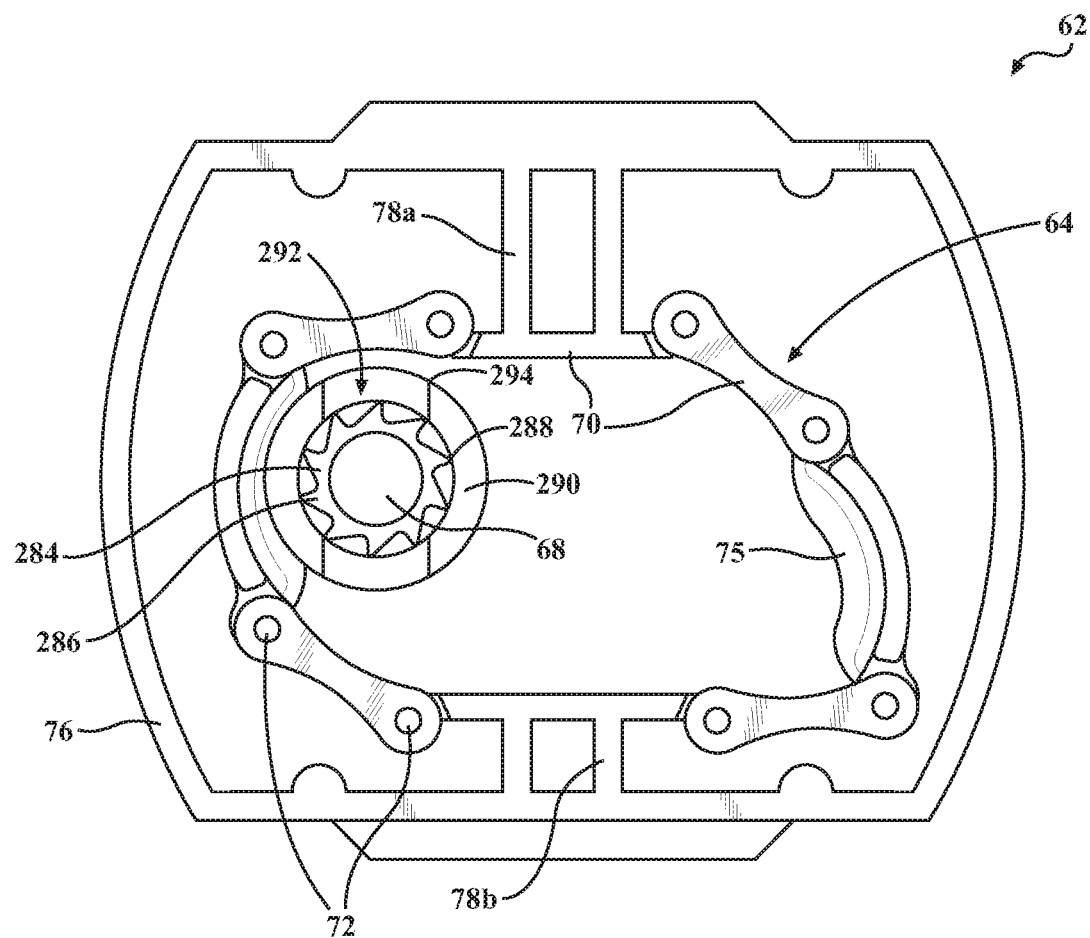
FIG. 9 is an isolated top view of an alternate carriage for the system of FIG. 1.

Referring now to FIG. 9, an isolated top view of another example of the carriage 62 of the system 42 for preparing bone stock is illustrated. The carriage 62 illustrated in FIG. 9 includes the carriage housing 76. The carriage housing 76 has a fixed inner profile (generally rectangular as illustrated) and is not deformable, while the wall 64 anchored thereto is resiliently deformable.

The resiliently deformable wall 64 of FIG. 9 includes eight wall segments 70i-n (shown in FIGS. 10A-C), all of which are moveably connected to one another via hinges 72. The resiliently deformable wall 64 of FIG. 9 includes two fixed wall segments 70i, 70j which are connected to the carriage housing 76 with anchors 78. These two wall segments 70i, 70j are connected to the carriage housing 76 with the anchor 78 including two pillars. This example also includes six wall segments 70k-p which are not directly anchored to the carriage housing 76. Four wall segments 70k, 70l, 70m, 70n are straight and present a flat inner surface. Two wall segments 70o, 70p are profiled to "catch" the bone stock and facilitate contact with the removal element 68 within the preparation chamber 66. These two profiled wall segments 70e, 70f each include the catch pad 75 disposed on the interior surface 74. The catch pads 75 catch and push the bone stock into the removal element 68, cause deformation of the wall 64, and facilitate movement of the bone stock within the preparation chamber 66 and ensures and removal of ligaments and other soft tissue from the bone stock.

FIGS. 10A-C are an isolated top view of the resiliently deformable wall 64 of FIG. 9. FIGS. 10A-C illustrate the movement of the eight wall segments 70a-h, all of which are moveably connected to one another via hinges 72. As is illustrated in example wall profiles $P_{E4}$, $P_{E5}$, and $P_{E6}$ of FIGS. 10A-C, the resiliently deformable wall 64 is designed to deform, e.g. articulate such that the inner profile of the wall 64 (which partially defines the preparation chamber 66), changes as the carriage 62 moves across the support surface 56 and engages bone. The changing profile of the wall 64 is illustrated in the exemplary wall profiles $P_{E4}$, $P_{E5}$, and $P_{E6}$. A changing inner profile of the wall 64 facilitates movement of the bone stock within the preparation chamber 66 and ensures and removal of ligaments and other soft tissue from the bone stock. It should be appreciated that an inner profile of the wall 64 changes because the wall 64 includes one or more articulating portions 65. In this example, the wall 64 includes two articulating wall portions 65, only one of which is numbered.

In FIGS. 11A-C, another wall 64 that is resiliently deformable, which may be used in the carriage 62 of FIG. 9, is illustrated. FIGS. 11A-C are isolated top views of the exemplary resiliently deformable wall 64, which includes two fixed wall segments 70q, 70r and two elastomeric wall segments 70s, 70t. The fixed wall segments 70q, 70r are connected to the carriage housing 76 with the anchors 78, each anchor 78 including two fixed pillars. The two elastomeric wall segments 70s 70t comprise an elastomeric material, e.g. silicone rubber, and are thus deformable. The two elastomeric wall segments 70s, 70t may or may not be directly anchored to the carriage housing 76. The four wall segments 70*q-t* are connected to one another via fixed couplings 73, e.g. adhered with adhesive, mechanically coupled, etc., or may be connected via movable couplings 72, e.g. hinges. As is illustrated in example wall profiles $P_{E7}$, $P_{E8}$, and $P_{E9}$ of FIGS. 11A-C, the inner profile of the wall (which partially defines the preparation chamber 66), changes, as the wall 64 deforms and stretches, as the carriage 62 moves across the support surface 56 and engages bone. The changing profile of the wall 64 is illustrated in the exemplary wall profiles $P_{E7}$, $P_{E8}$, and $P_{E9}$. A changing inner profile of the wall 64 facilitates movement of the bone stock within the preparation chamber 66 and ensures and removal of ligaments and other soft tissue from the bone stock. In the configurations of the FIGS. 11A-C, the bone material may contact the elastomeric wall segments directly. It should be appreciated that an inner profile of the wall 64 changes because the wall includes one or more resilient portions 65. In this example, the wall includes two resilient, articulating wall portions 65, only one of which is numbered.

As is set forth above and illustrated in FIGS. 5, and 23-25, the carriage 62 is moveably mounted in the void space 60 on the support surface 56 of the base 54. Referring now to FIGS. 2 and 4, the base 54 typically includes one or more slots 80*a*, 80*b* with one or more drive elements 82 movably disposed therein, the one or more drive elements 82*a*, 82*b* operatively connect the drive train and the carriage 62. In some examples, the drive elements 82*a*, 82*b* are operatively attached to the cam assembly, which is located in the base module 44 and releasably attached to the carriage 62 within the preparation module 50. Alternatively, in other examples such as those illustrated in FIGS. 30-42, the drive elements 82*a*, 82*b* are operatively attached to the cam assembly and the carriage 62, both of which are part of the preparation module 50.

Figure 12:
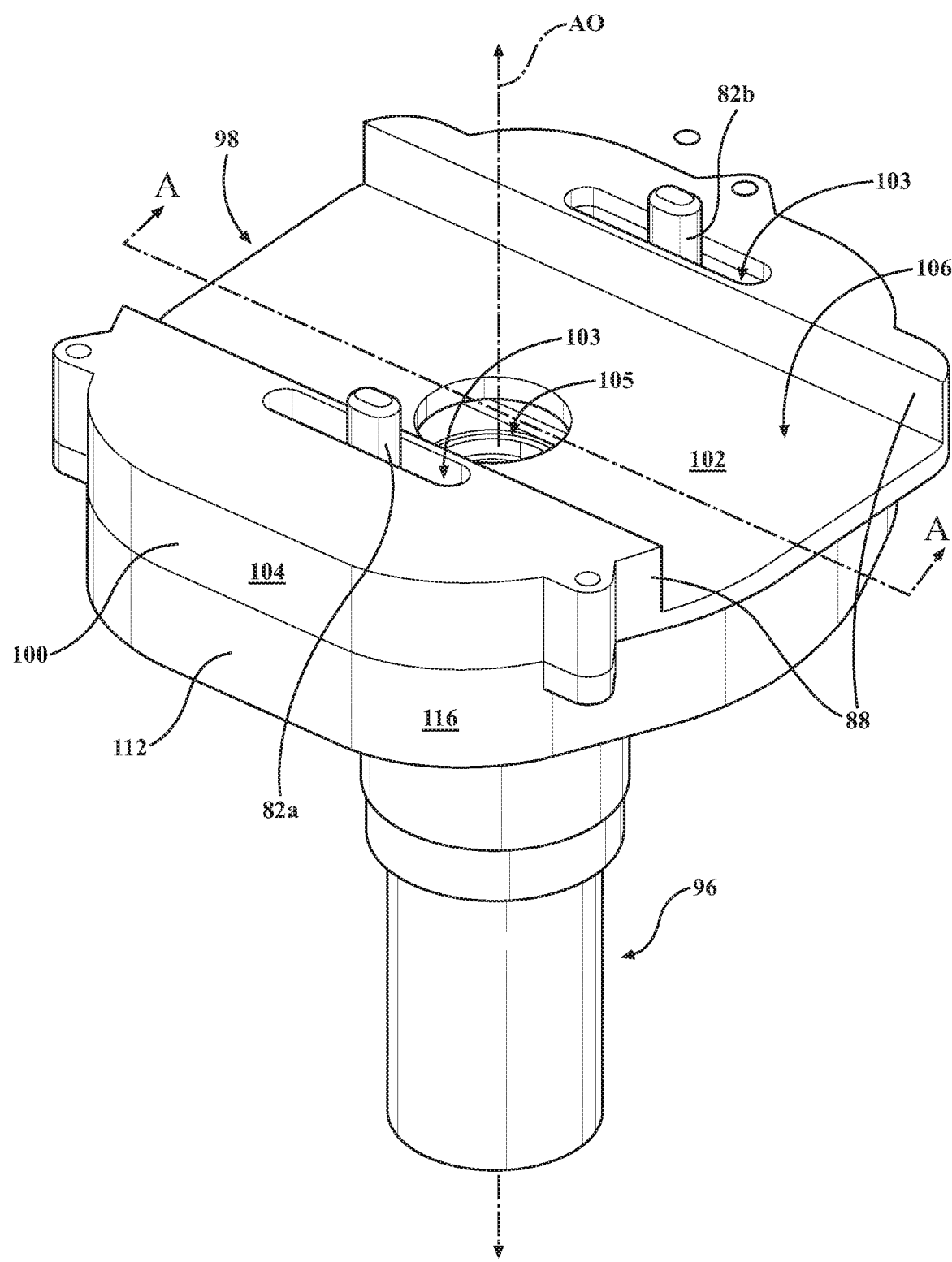
FIG. 12 is an isolated perspective view of a pedestal and a drive module of the base module of the system of FIG. 1.
Figure 13:
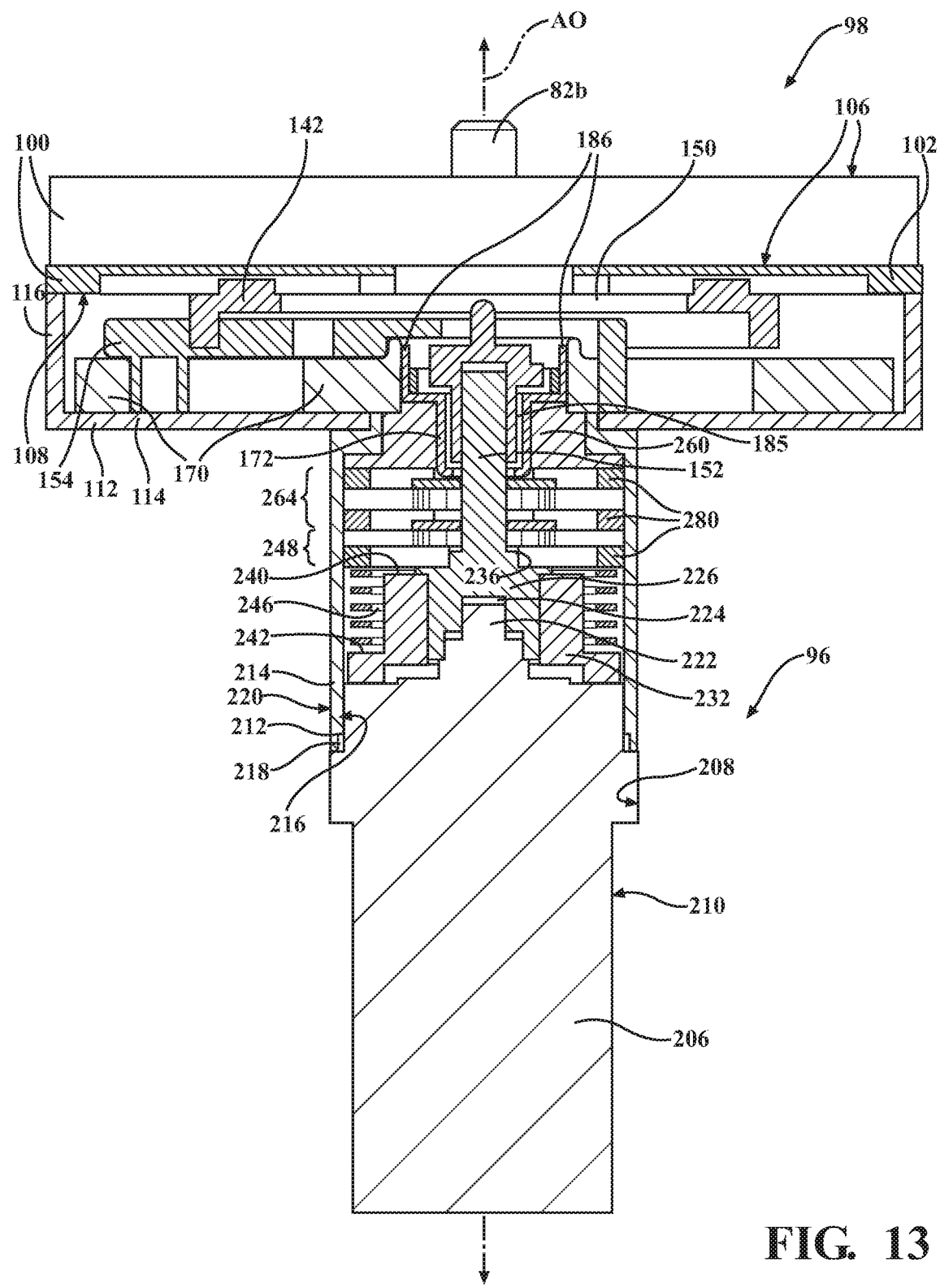
FIG. 13 is a cross-sectional view of the pedestal and the drive module of FIG. 12 taken along line A-A.

Typically, the drive elements 82 cooperate with a corresponding engagement element 84, e.g. sleeves 84*a*, 84*b*, on the carriage 62 to couple the drive train to the carriage 62. In the system 42 illustrated in FIGS. 1-28, the drive elements 82 cooperate with two elements, such as sleeves 84. These sleeves 84 may be disposed on an outer surface 86 of the carriage housing 76 of the carriage 62. In FIGS. 12 and 13, the base 54 includes a first slot 80*a* and a second slot 80*b*, wherein a first drive element 82*a* and a second drive element 82*b* are disposed in a first slot 80*a* and a second slot 80*b* respectively. The drive elements 82*a*, 82*b* are operatively attached the drive train and the carriage 62 via insertion into a first sleeve 84*a* and a second sleeve 84*b*. The drive elements 82*a*, 82*b* are configured to move from a first position to a second position within each of the first and second slots 80 of the sleeves 84 to move the carriage 62 laterally across the support surface 56 of the base 54. Movement of the carriage 62 across the support surface 56 is described further below and illustrated in the schematic drawings FIGS. 24-26. It should be appreciated that other ways of moving the carriage 62 across the support surface are contemplated, including means to pivot the carriage about the support surface, such as those described in U.S. Pat. No. 8,672,942, the contents of which are hereby incorporated by reference.

Still referring to FIG. 12, the preparation module 50 may include one or more guides 88 in the void space 60, which cooperate with the carriage 62 to guide linear movement of the carriage 62 across the support surface 56 of the base 54. In the examples illustrated, the one or more guides 88 in the void space 60 cooperate with an outer surface 86 of the carriage housing 76 of the carriage 62. However, various configurations of the one or more guides 88 are contemplated herein, including guides 88, which cooperate with an inner surface of the carriage housing 76 of the carriage 62. If included, the one or more guides 88 may be coupled to the support surface 56, or the support surface 56 may be modified or profiled to form the one or more guides 88. For example, in the support surface 56 illustrated in the example of FIG. 12, two guides 88 are formed into the support surface 56 of the base 54 in the void space 60 (i.e. the support surface 56 is profiled).

The drive train is operably coupled to the carriage 62 and configured to transfer rotary power from the motor 46 to cause linear movement of the carriage 62 across the support surface 56 of the base 54. The drive train is also operably coupled to the removal element 68 and is configured to cause rotational movement of the one or more removal elements 68 within the preparation chamber 66. In one configuration, upon actuation of the drive train, the carriage 62 moves laterally across the support surface 56 of the base 54 and the removal element(s) 68 move rotationally in the preparation chamber 66. It should be appreciated that the drive train including the cam assembly and a gear train, which are described further below, may be located in the preparation module 50, in both the preparation module 50 and the base module 44, or entirely in the base module 44. In the system 42 of FIGS. 1-28, the drive train is located in the base module 44 to reduce cost associated with the manufacturing of the preparation module 50 since the preparation module 50 is supplied as a disposable.

The drive train, which may be disposed in the base module 44, is configured to move the removal element 68 in a forward rotational direction (e.g. clockwise) and in a reverse rotational direction (e.g. counter-clockwise), opposite the rotational direction, and concurrently cause linear movement of the carriage 62 laterally across the support surface 56 of the base 54. It should be appreciated that the drive train advantageously allows forward and reverse rotational movement of the removal element 68 while also moving the carriage 62 across the support surface 56. Reversing direction of the removal element 68 provides additional movement and further removal of ligaments and other soft tissue from the bone stock within the preparation chamber 66, and also allows an operator to reverse the direction of the removal element 68 when material becomes "jammed" against the removal element in the preparation chamber 66 and the removal element 68 will not move, which often "unjams" the removal element 68.

Referring now to the base module 44, in particular FIGS. 1 and 2, the base module 44 may include a foot 90. From an actuation perspective, the push button 230 is located on the foot 90 and operably connected to a switch internal to the foot 90 (not illustrated). The push button 230 is biased with a spring (not illustrated) into its extended position, in which the switch is electrically open. Depression of the push button 230 against this spring-biased force electrically closes the switch and provides power to the motor 46. Power to the motor 46 is discontinued when the push button 230 is released and the switch electrically opens. The motor 46 powers the drive train. In turn, the drive train is operably coupled to the carriage 62 and configured to transfer rotary power from the motor 46 to the carriage 62 and the removal element 68.

The system 42 for preparing bone stock is electronically powered and controlled with an electronic control system, with various components being described immediately below. In some examples, a socket on the foot 90 of the base module 44 receives a cable from a control console. The socket includes terminals that are electrically connected to conductors within the cable. The cable is connected between the base module 44 and the control console. The cable contains conductors over which the energization signals, e.g. signals to actuate the motor 46, are supplied from the control console to the motor 46. Internal to the foot 90 is a circuit board (not illustrated) electrically in series between the socket and the motor 46. Mounted to the circuit board are electrical components that function as an electric motor controller. The function of the motor controller is to regulate power received at the socket for energizing the motor 46. The switch is placed electrically in series between the socket and the circuit board. Alternatively, the switch is placed electrically in series between the circuit board and motor 46. Power received from the control console through the cable and the socket is regulated by the motor controller and provided to the windings of the motor 46 when the switch is electrically closed.

The drive train is configured to rotate the removal element 68 in a forward direction (e.g. clockwise) and also in a reverse direction (e.g. counter-clockwise), opposite the forward direction, and concurrently causes linear movement of the carriage 62 laterally across the support surface 56 of the base 54. As such, the electronic control system allows an operator to actuate the motor 46 to provide rotational power in a forward direction (e.g. clockwise), or in a reverse forward direction (e.g. counter-clockwise).

Power may be supplied to the base module 44 via wire or battery. In some configurations, a battery powered control unit is utilized. In such configurations, the battery powered control unit supplies electrical energization signals to the motor 46 to actuate the motor 46. Of course, the battery powered control unit may be integrated into the base module 44.

As described above, power received from the control console through the cable and the socket (or from the battery powered control unit) is regulated by the motor 46 controller and provided to the windings of the motor 46 when the switch is electrically closed. Power to the motor 46 may be provided continuously when the push button 230 is actuated, and then discontinued when the push button 230 is actuated a second time, or power may be provided for a predetermined period of time such as 2 minutes after actuation of the push button 230, Alternatively, the push button 230 may be a rocker switch having on and off positions.

The specific structure and configuration of the electronic control system and its electrical components described above are of any suitable type well known to those of ordinary skill in the motor control-related arts and are thus not illustrated. Further, various structures and configurations of the electronic control system and its electrical components described above are described in U.S. Pat. Nos. 8,672,942 and 9,687,361, the contents of which are hereby incorporated by reference, both of which are directed towards electrically operated bone preparation and milling systems.

A leg 92 extends upwardly from the foot 90. The leg 92 comprises one or more segments 94, which support a drive module 96 having a pedestal 98 thereon. In the system 42 of FIGS. 1-28, the base module 44 includes a lower leg component 118 and an upper leg component 120 which are configured to engage one another. The upper and lower leg components 120, 118 may be configured to slideably engage with one another so that the length of the leg 92 may be adjusted as desired by a user. As such, a user may adjust the height of the preparation module 50 when mounted on the base module 44 for ergonomic and other reasons.

Figure 26B:
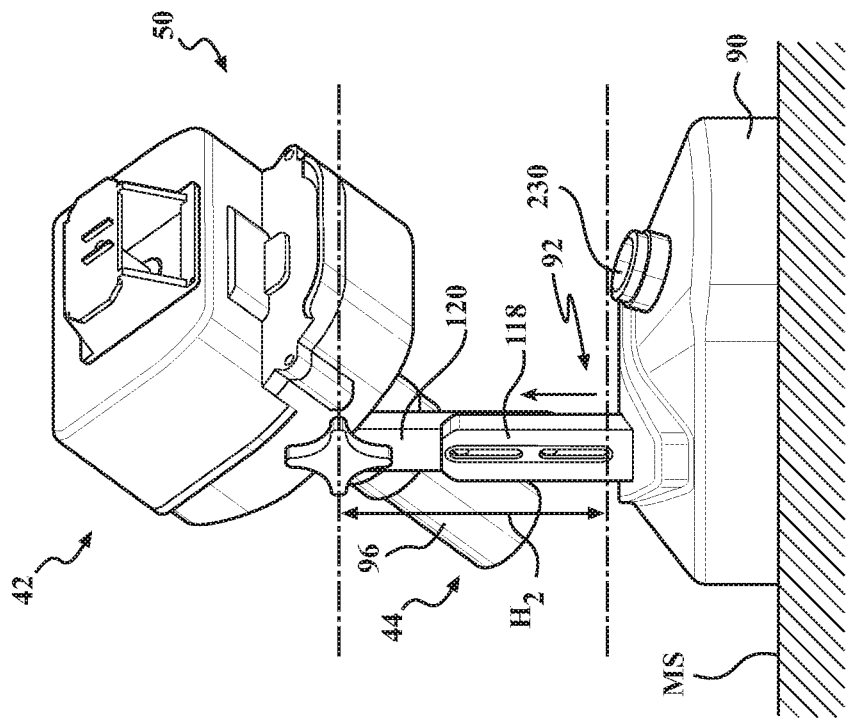
FIGS. 26A and 26B are top perspective views of the system of FIG. 1 illustrating the preparation module mounted at different heights relative to a mounting surface.
Figure 26A:
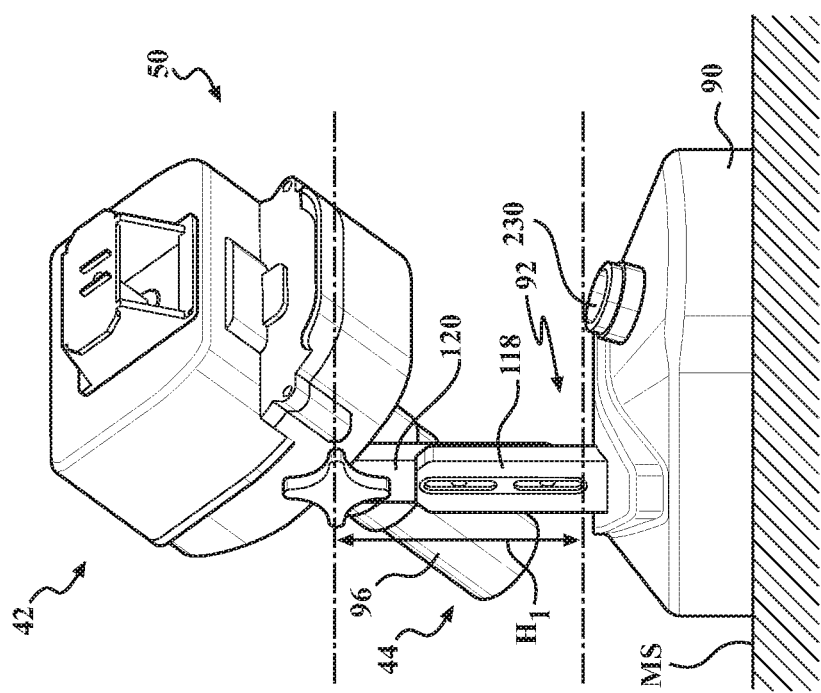

Referring now to the "Height Adjustment" schematic set forth in FIGS. 26A and 26B, the upper and lower leg components 120, 118 are shaped to engage one another. In the example illustrated, corresponding slots in the upper and lower leg components 120, 118 are shaped to engage a coupling system (not illustrated) which may be loosened so that the height of the preparation module 50 relative to the mounting surface $M_s$ may be adjusted and tightened to secure the preparation module 50 at a desired height. In FIGS. 26A and 26B, the preparation module 50 is illustrated at a first height $H_1$ off of the mounting surface $M_s$ and a second height $H_2$, which is greater than the first height $H_1$, off of the mounting surface $M_s$.

Figure 27A:
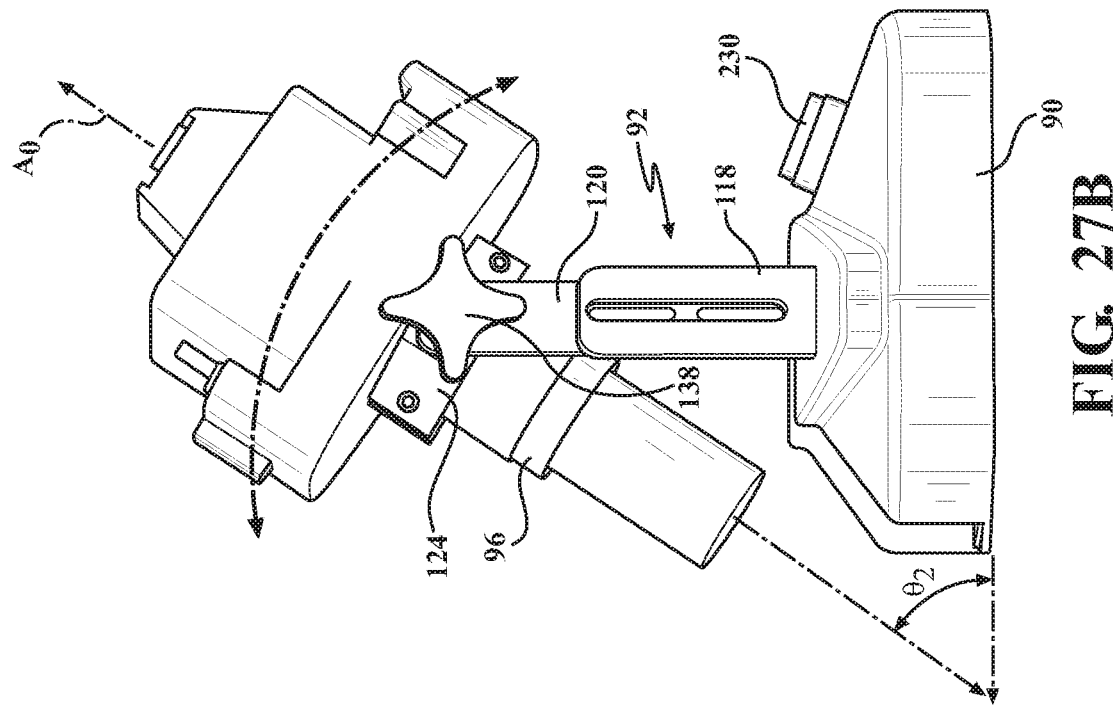
FIGS. 27A and 27B are top perspective views of the system of FIG. 1 illustrating the preparation module mounted at different angles relative to a mounting surface.
Figure 27B:
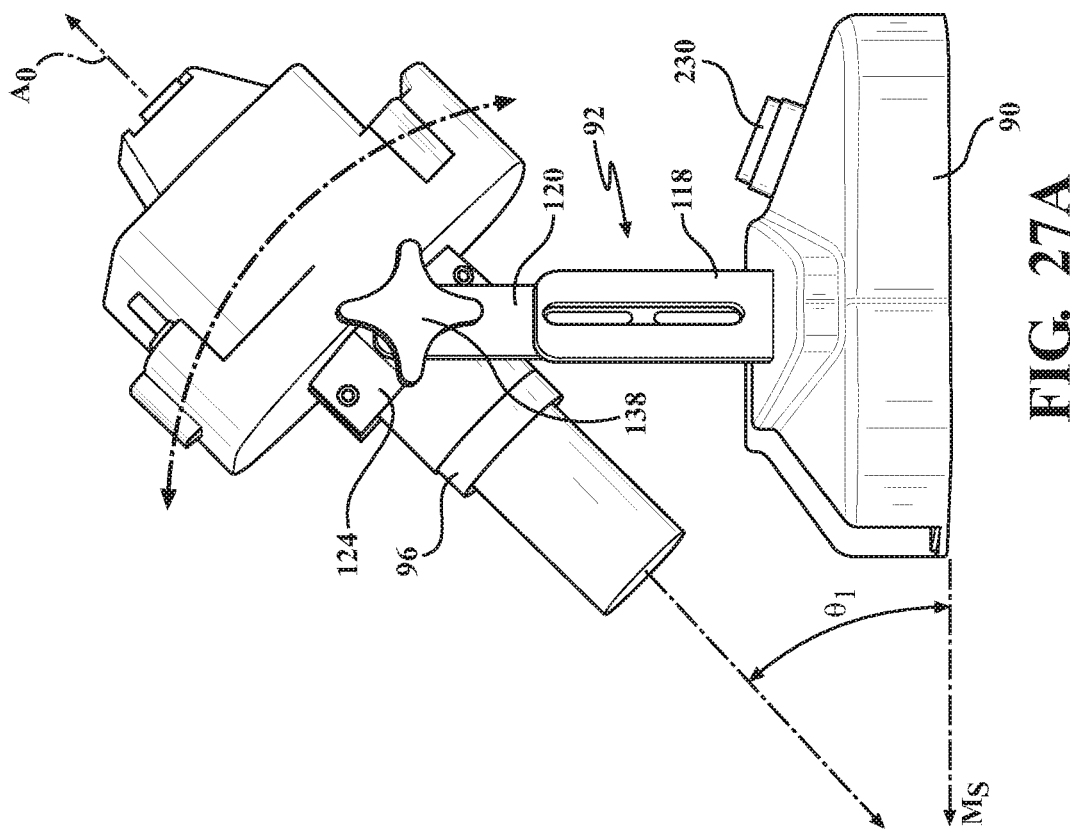
Figure 28:
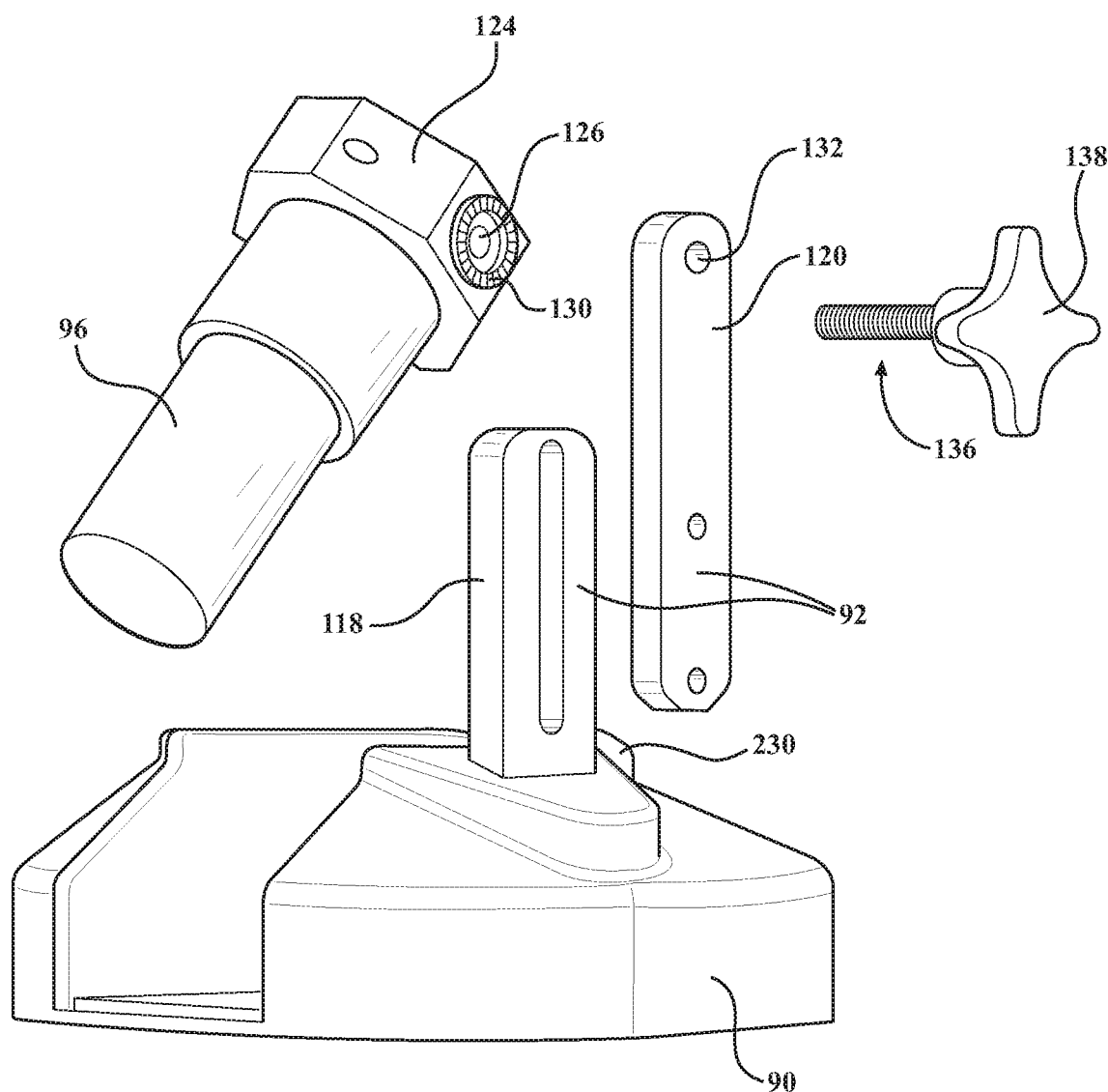
FIG. 28 is an exploded view of the foot, leg, and drive module of the system of FIG. 1.

Referring now to the "Angle Adjustment" schematic set forth in FIG. 27, an exterior collar 124 is releasably attached to, and disposed radially about the drive module 96. The exterior collar 124 has a threaded engagement hole 126 in its exterior surface 128 and a circular engagement profile 130 having peaks and valleys disposed radially about the outer perimeter of the threaded engagement hole 126. The upper leg component 120 includes a threaded through hole 132 and a circular engagement profile 130 having peaks and valleys disposed radially about a perimeter of the threaded through hole 132 on an interior surface 131 of the upper leg component 120. A threaded pin 136 with a knob 138 is disposed in the threaded through hole 132 and into the threaded engagement hole 126. The knob 138 may be turned to tighten the threaded pin 136 into the through hole 132 of the upper leg component 120 and the engagement hole 126 of the exterior collar 124 to force the corresponding engagement profile 134 on the interior surface 131 of the upper leg component 120 into the circular engagement profile 130 on the exterior surface 128 of the exterior collar 124 to secure the drive module 96 and the pedestal 98 at a desired angle Θ. The preparation module 50 mounted on the pedestal 98, which is mounted on the drive module 96. As such, the preparation module 50-pedestal 98-drive module 96, which extend along an operational axis AO, may be incrementally moved and tightened into position for use at a desired angle relative to the mounting surface $M_s$. Typically, the operational axis OA is centrally disposed and extends along the drive module 96 and is centrally located and perpendicular to the mounting surface 106 of the pedestal 98 and and/or support surface 56 of the base 54. The knob 138 is loosened prior to moving or adjusting an angle at which the preparation module 50 is mounted on the foot 90 and the leg 92 of the base module 44. The angle may then be adjusted, and the knob 138 may be tightened to secure the preparation module 50 at the desired angle relative to the horizontal surface upon which the foot 90 of the base module 44 stands. As such, a user may adjust the angle Θ at which the preparation module 50 is mounted on the base module 44 for optimal performance and/or user ergonomics.

In some examples, the operational axis OA is inclined or set-off from the horizontal by from about 80° to about 15°, or about 60° to about 25°. In other words, the preparation module 50 is mounted on the pedestal 98 at an angle within the ranges set forth above. Such an angled mounting position advantageously utilizes gravity to facilitate movement of bone stock within the preparation chamber 66 when preparing bone stock with the system 42. Because the support surface 56 is inclined, gravity funnels bone stock in the preparation chamber 66 towards a location that facilitates contact with the removal element 68. This angled mounting position of the preparation module 50 in tandem with the wall 64, facilitates movement of the bone stock within the preparation chamber 66 and ensures and removal of ligaments and other soft tissue from the bone stock.

It should be appreciated that the movement of the wall 64 relative to the removal element 68 may be adjusted so that preparation chamber 66 moves diagonally relative to the removal element 68 to result a first position of the removal element 68 being the lowest corner of the preparation chamber 66 to facilitate contact with the bone stock fed by gravity. It is to be appreciated that the concept of positioning the removal element 68 in the lowest corner of the preparation chamber 66 to facilitate gravity fed contact between the bone stock and the removal element 68 in a first position may be accomplished a number of ways including angling the base 54 and support surface 56, altering the path of the preparation chamber 66 of the support surface 56, and/or changing the profile and properties of the wall 64, all of which have been contemplated herein.

In FIG. 12, an isolated perspective view of the pedestal 98 on the drive module 96 is illustrated. FIG. 13 is a cross-sectional view of the pedestal 98 and the drive module 96 of FIG. 12 taken along line A-A, FIGS. 14-17 are perspective, isolated, exploded and/or cross-sectional views of various components of the drive train including the cam assembly and the gear train. It is to be appreciated that the drive train includes a plurality of components, which cooperate to drive the carriage 62 and removal element 68.

Referring now to FIGS. 12 and 13, the pedestal 98 includes a first portion 100 having a mounting wall 102 and a sidewall 104. The mounting wall 102 has a mounting surface 106 and an inner surface 108. The mounting surface 106 is configured to receive an outer surface 110 of the base 54 of the preparation module 50. As such, the mounting wall 102 also has one or more slots 103 which correspond to the one or more slots 80 on the base 54 with the one or more drive elements 82a, 82b moveably disposed therein (when the preparation module 50 is mounted on the base module 44). Further, the mounting wall 102 also includes a central opening 105, configured to receive a mounting key 194 on the preparation module 50, through which a drive shaft 152 and other elements of the drive train are disposed. The pedestal 98 includes a second portion 112 comprising a lower floor 114 and a sidewall 116. The first and second portions 100, 112 of the pedestal 98 are configured to be attached to one another and cooperate to form a housing in which some components of the drive train are housed.

Referring now to FIGS. 14-17, the pedestal 98 houses drive train components including the cam assembly, which drives the carriage 62. The cam assembly includes a cam follower 142, a cam 154, and a cam carrier 170. The cam follower 142 has an upper surface 144 and a lower surface 146 having a track 148 thereon with an oblong profile. The upper surface 144 of the cam follower 142 includes the one or more drive elements 82 coupled thereto which extend upwardly along the operational axis AO (towards the preparation module 50) and are moveably disposed in the one or more slots 103 in the mounting wall 102 (see FIG. 12). The cam follower 142 also includes a drive slot 150 with a drive shaft 152 moveably disposed therein. The upper surface 144 of the cam follower 142 is proximate to, but set off from, the inner surface 108 of the mounting wall 102. As such, the upper surface 144 of the cam follower 142 is opposite the outer surface 110 of the base 54 with the mounting wall 102 disposed therebetween.

Figure 14:
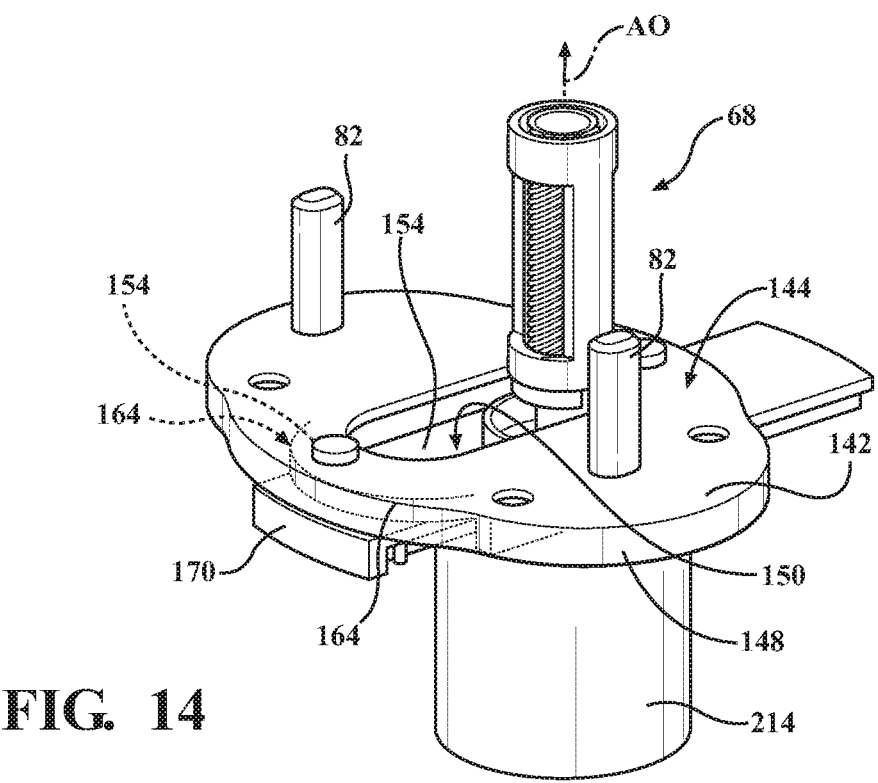
FIG. 14 is an isolated top perspective view of a cam assembly of a drive train of the system of FIG. 1.
Figure 15:
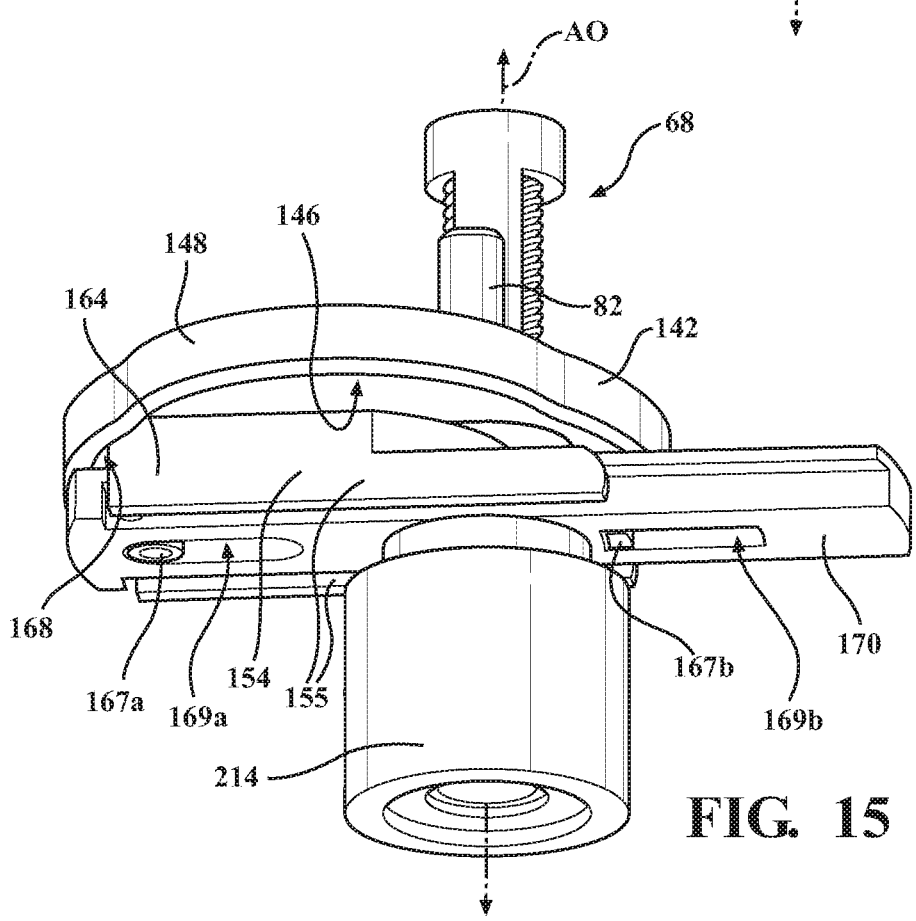
FIG. 15 is an isolated side perspective view of the cam assembly of the drive train of the system of FIG. 1.
Figure 16:
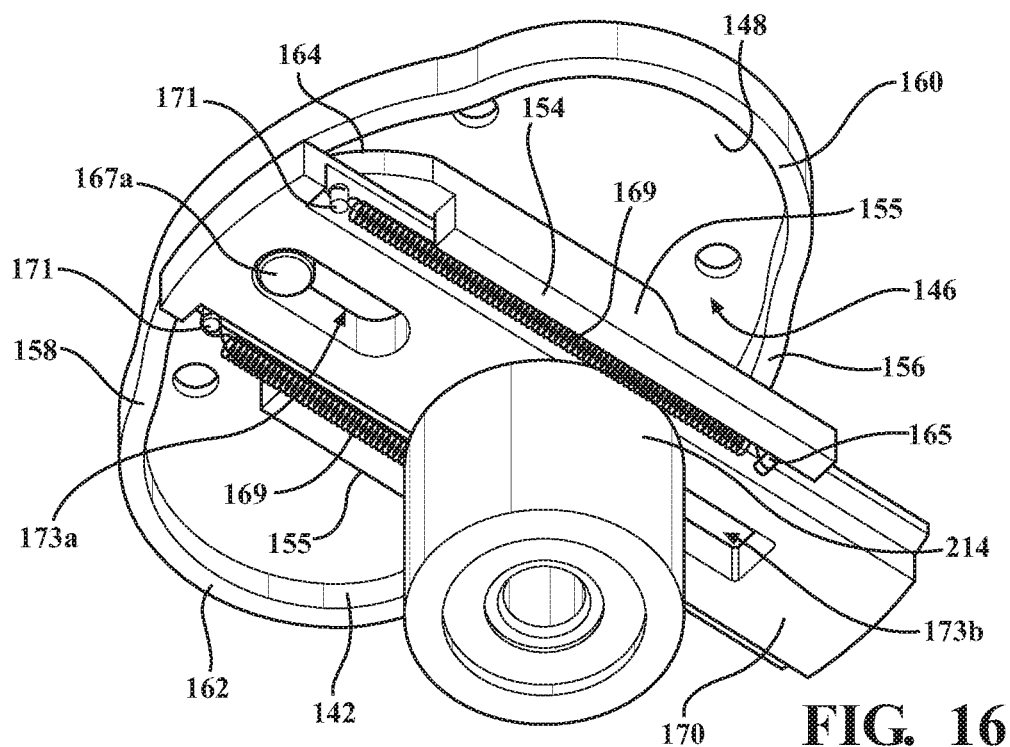
FIG. 16 is an isolated bottom perspective view of the cam assembly of the drive train of the system of FIG. 1.

The exemplary cam assembly illustrated in FIGS. 14-17 drives the carriage 62, includes the cam follower 142, the cam 154, and the cam carrier 170. The cam 154 is coupled to the drive shaft 152 and disposed adjacent the lower surface 146 of the cam follower 142 on the oblong track 148. Referring specifically to FIG. 16, the oblong track 148 has two elongated segments 156, 158 opposite one another and two arcuate segments 160, 162 opposite one another. That is, the elongated segments 156, 158 and arcuate segments 160, 162 of the oblong track 148 alternate. The cam 154 is configured to cooperate with the oblong track 148 to transfer rotary power from the drive train to cause linear movement of the cam follower 142 and cause the corresponding linear movement of the carriage 62 across the support surface 56 of the base 54 via the movement of the drive elements 82 which are disposed in the sleeves 84 of the carriage 62.

Figure 17:
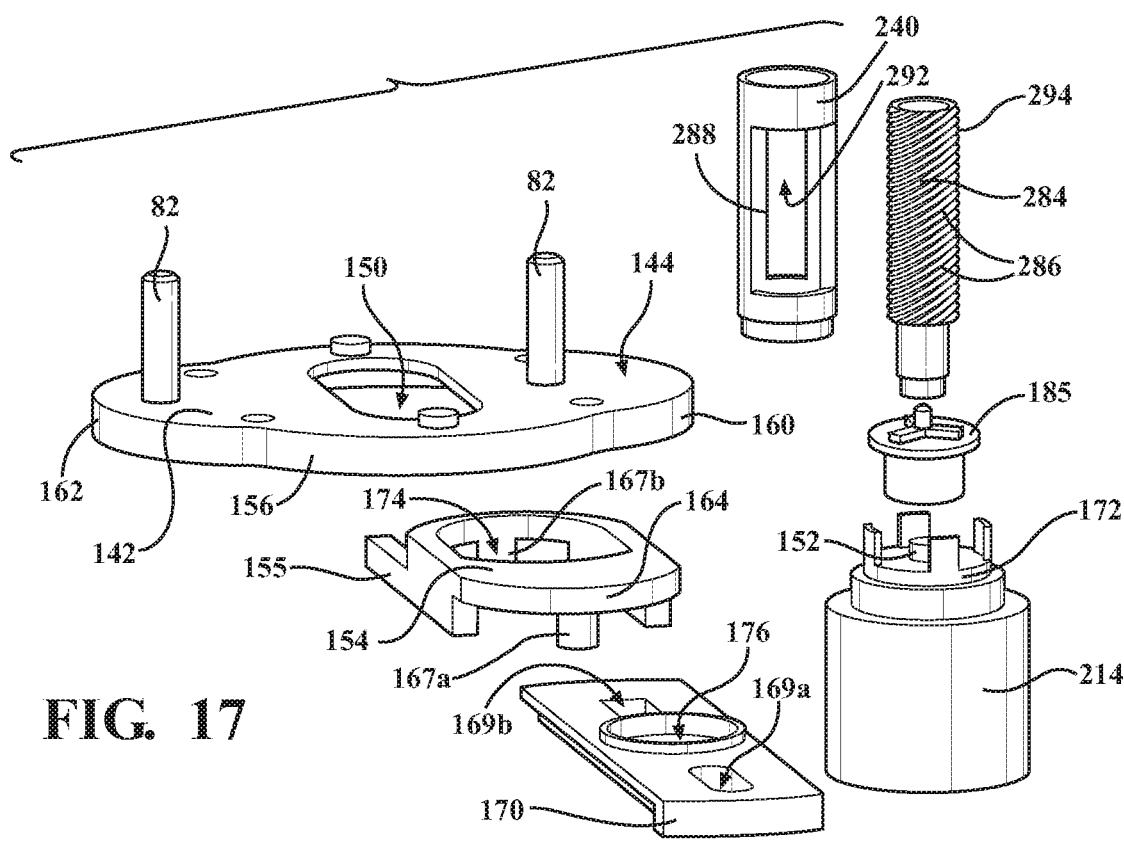
FIG. 17 is an isolated exploded view of the cam assembly of the drive train of the system of FIG. 1.

Referring now to FIGS. 15 and 16, the cam 154, which is coupled to the drive shaft 152, turns like an arm on a clock along the track 148 of the cam follower 142. In some examples, movement of the cam 154 along the oblong track 148 is facilitated by its end tip 164, which engages with or abuts an inner surface 149 (the inner surface 149 is shown in FIG. 17) of the oblong track 148. In some examples, the end tip 164 may be spring-loaded with springs 169 to press against the inner surface 149 of the track 148 and also provide some give (not shown). In other examples, the end tip 164 of the cam 154 has a track notch 168 having a cross-sectional profile that corresponds to a cross-sectional profile of the track 148 (not shown).

FIGS. 14-16 are isolated, perspective views of the cam follower 142, cam 154, removal element 68 and portions of the drive train. FIG. 17 is an exploded view of the components illustrated in FIGS. 14-16. Referring now to FIGS. 14-17, the end tip 164 of the cam 154 is engaged with the track 148, i.e., the track 148 is disposed in the track notch 168. In FIGS. 14-16, the cam 154 is coupled to the cam carrier 170, which is in turn coupled to a cam collar 172 disposed about, but isolated from, the drive shaft 152. The cam carrier 170 is operatively attached to the underside of the cam 154. The cam 154 has a central drive opening 174, and the cam carrier 170 also a central drive opening 176 in which components of the drive train, including the drive shaft 152, are at least partially disposed. The cam carrier 170 rotates with the cam collar 172 about the operational axis OA and carries the cam 154, which in-turn moves the cam follower 142, which in-turn actuates movement of the carriage 62 across the support surface 56.

As is illustrated in FIG. 13, just below the inner surface 108 of the mounting wall 102 is the cam follower 142, which is moveably mounted on the cam 154 and includes a drive slot 150 in which elements of the drive train are moveably disposed around the operational axis AO. The upper-surface of the cam follower 142 is offset (not disposed on the inner surface 108 of the mounting wall 102). The cam 154 is slideably mounted on the cam carrier 170, which is mounted on the cam collar 172. The cam collar 172 moves rotationally about the operational axis AO and transfers power from a gear assembly, which is operably attached to the drive shaft 152, to the cam 154 which cooperates with the cam follower 142 to transfer rotational movement of the drive shaft 152 into linear movement of the drive elements 82.

Figure 18:
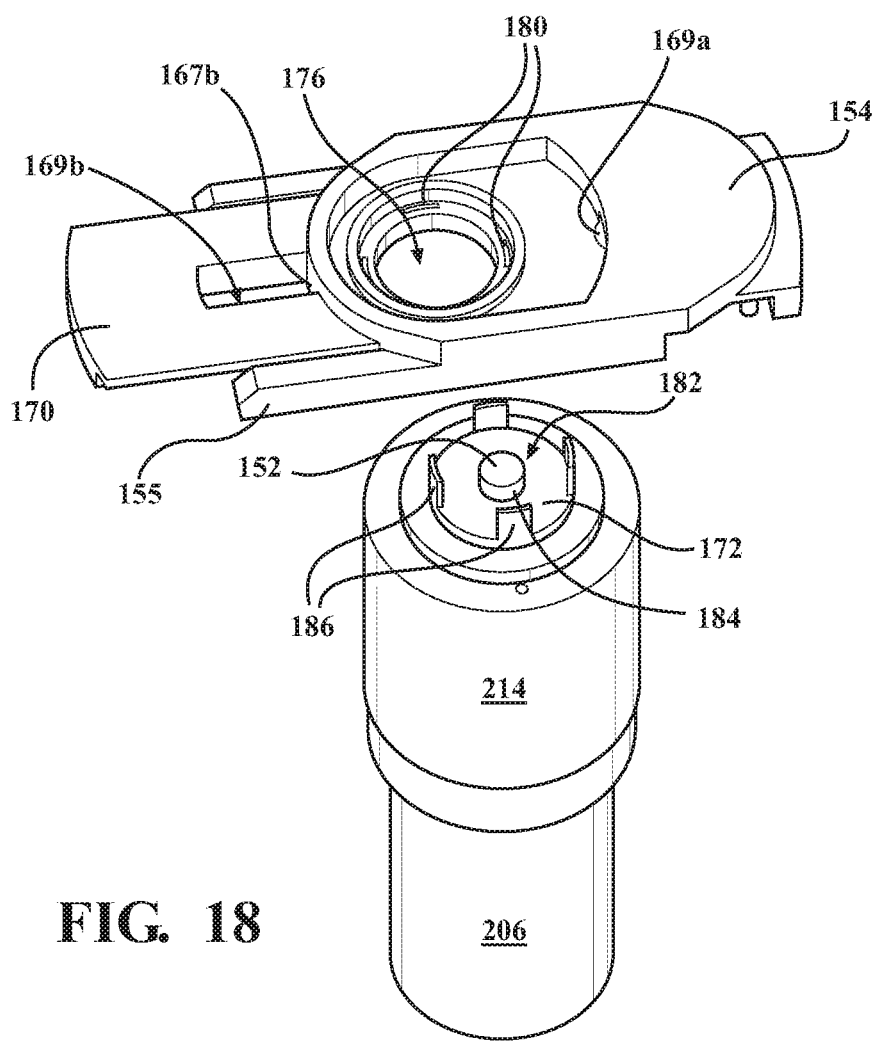
FIG. 18 is an exploded perspective view of a drive module and a cam carrier with features that releasably couple a cam assembly to a drive train.

Referring to FIG. 18, the cam collar 172 includes an upper surface 182 having a centrally located drive shaft opening 184 and a plurality of drive teeth 186 that are circumferentially and equiangularly spaced apart. The plurality of drive teeth 186 on the cam collar 172 engage a plurality of slots 180 in a bottom surface 178 of the cam carrier 170. The plurality of slots 180 are also circumferentially and equiangularly spaced apart around the central drive opening 176 of the cam carrier 170 to correspond with the location of the plurality of drive teeth 186. The plurality of slots 180 mate with the plurality of drive teeth 186. The walls of each slot 180 may be parallel to the respectively interfacing surfaces of each drive tooth 186 and slideably received therein. The cam collar 172 may be spring-loaded and thus define clutch for transferring torque from the drive shaft 152 to the cam assembly when the plurality of drive teeth 186 on the cam collar 172 are received in the plurality of slots 180 on the cam carrier 170.

Still referring to FIG. 18, the cam collar 172 is disposed in the drive module 96, with the upper surface 182 visible and centrally located to define an upper exterior surface of the drive module 96. The upper surface 182 of the cam collar 172 has the four circumferentially and equiangularly spaced apart drive teeth 186 thereon and the centrally located drive shaft opening 184 with the drive shaft 152 visible therein. Further, the cam carrier 170 (illustrated with the cam 154 attached) has the four corresponding slots 180 circumferentially and equiangularly spaced apart around the central drive opening 176. The plurality of drive teeth 186 on the upper surface 182 of the cam collar 172 engage the corresponding slots 180 to transfer power from the drive shaft 152 and actuate cam assembly, which in turn actuates the carriage 62. Of course, it should be appreciated that other teeth arrangements and slot arrangements may be suitable.

Figure 25A:
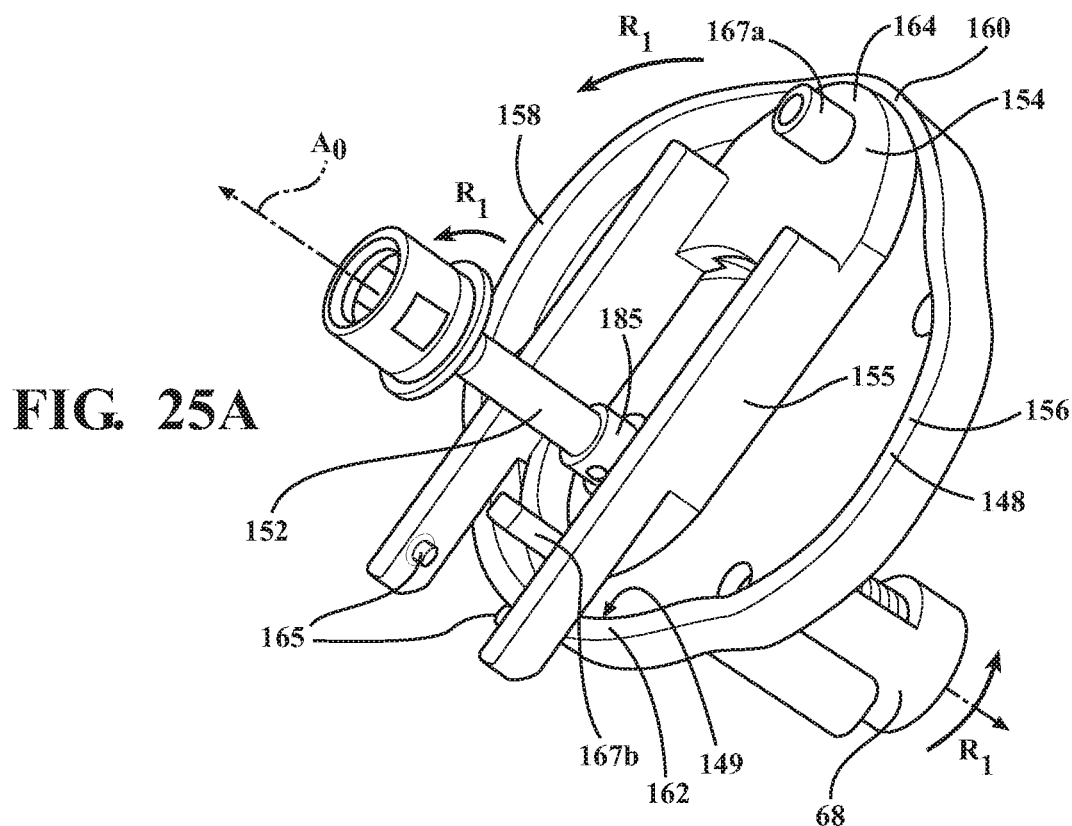
FIGS. 25A and 25B are an isolated perspective bottom view of the cam assembly corresponding to the preparation module of FIGS. 23A and 23B.
Figure 25B:
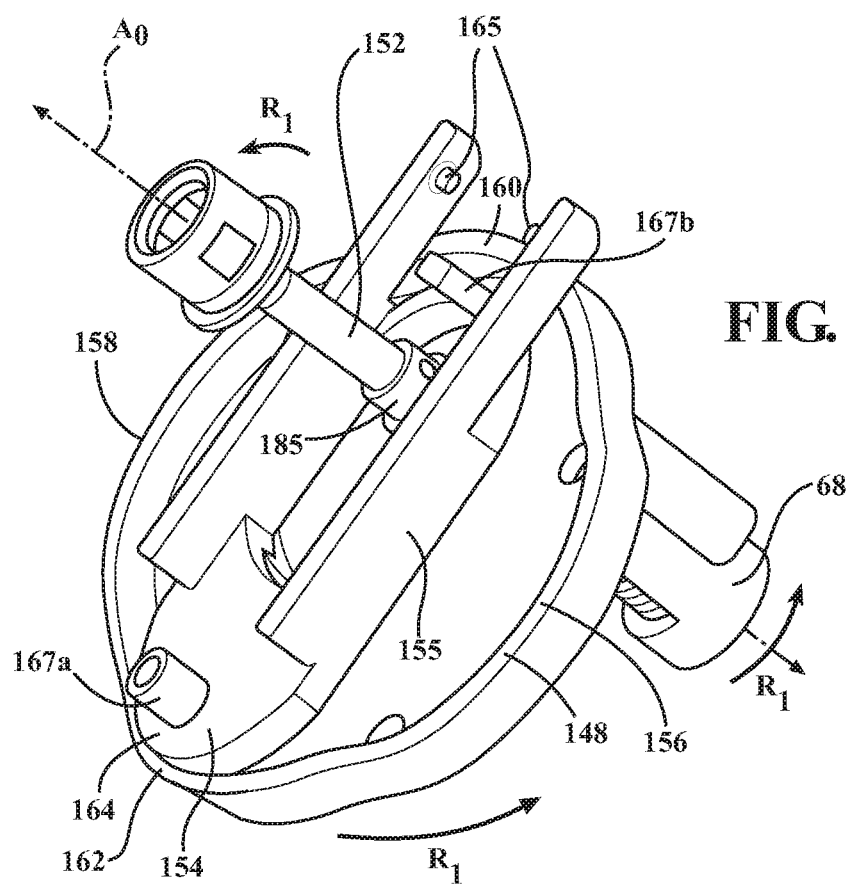

Referring back to FIGS. 15 and 16, the cam 154 is mounted on and slideably engaged with the cam carrier 170. Further, the engagement between the cam 154 and the cam carrier 170 is spring loaded. As such, the cam 154 which is connected to the gear train via the cam carrier 170 is spring-loaded via the springs 169 on the track 148 of the cam follower 142. Referring specifically to FIG. 16, the cam carrier 170 includes two cam carrier spring posts 171, and the walls of a cam 154 include two cam spring posts 165. Two springs 169 connect the two cam carrier spring posts 171 to the respective two cam spring posts 165. The cam 154 comprising two sidewalls 155 straddles the cam carrier 170 and the cam carrier 170 slides between the two sidewalls. The cam sidewalls 155 create a path for the cam 154 and can be referred to as a cam slide. Two pegs 167*a*, and 167*b* (only 167*a* is shown in FIG. 16, but both are shown in FIGS. 25A and 25B) on the cam 154 cooperate with two slots 173*a* and 173*b* on the cam carrier 170 to guide movement of the cam 154 on the cam carrier 170. As such, when the carriage 62 stops moving, e.g. due to jammed bone stock, the cam 154 slides back on the cam carrier 170 guided by its cam slide 155 and then springs back into place when the jammed bone stock within the preparation chamber 66 of the carriage 62 breaks up due to the articulating wall 70. This allows for the carriage 62 to stop moving when bone stock jams between the removal element 68 and wall 64 within the preparation chamber 66 while the drive train and cam assembly continue to operate. As such, jamming of the assembly 40 is prevented.

Figure 23A:
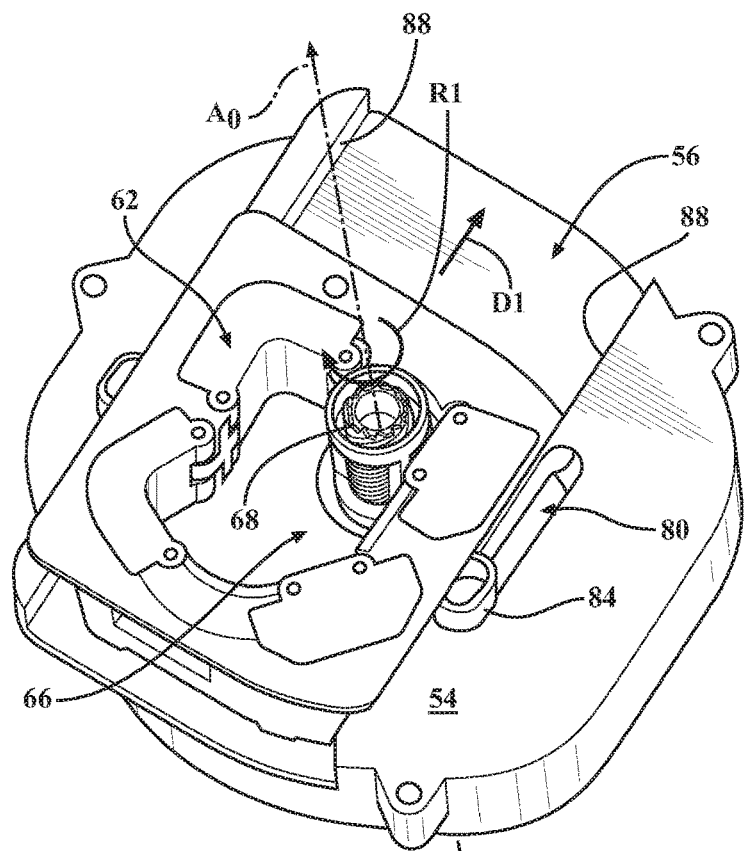
FIGS. 23A and 23B are isolated perspective top views of the carriage moveably disposed in the preparation module, with the carriage illustrated moving linearly in a first direction $D_1$ and a second direction $D_2$ across a support surface of a base of the preparation module.
Figure 23B:
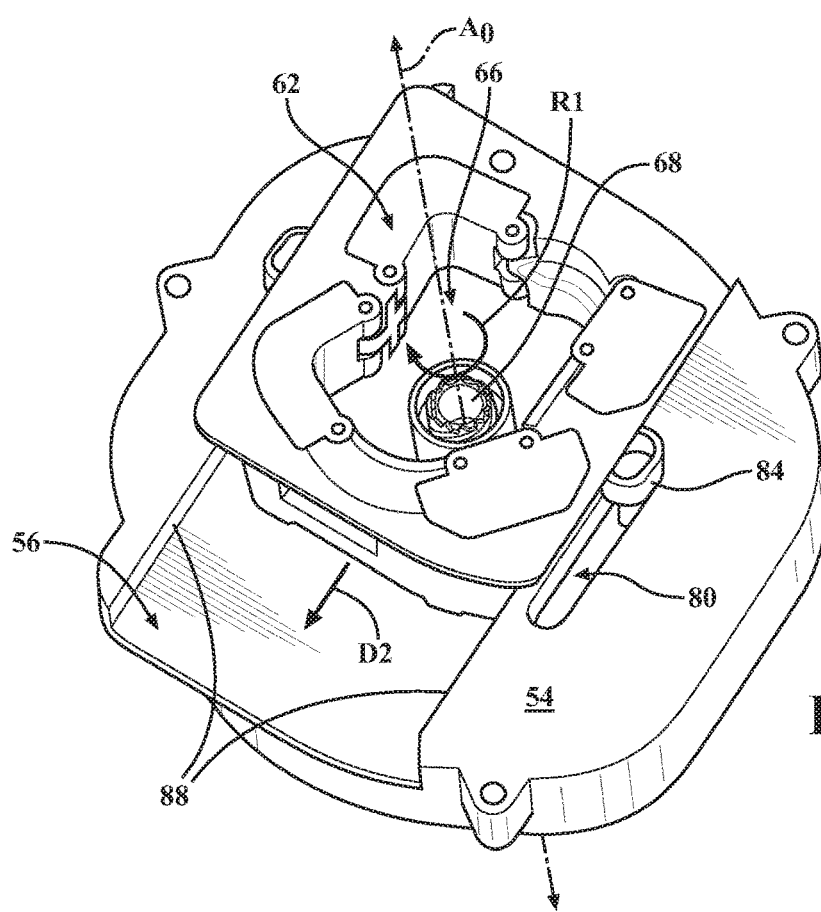
Figure 24A:
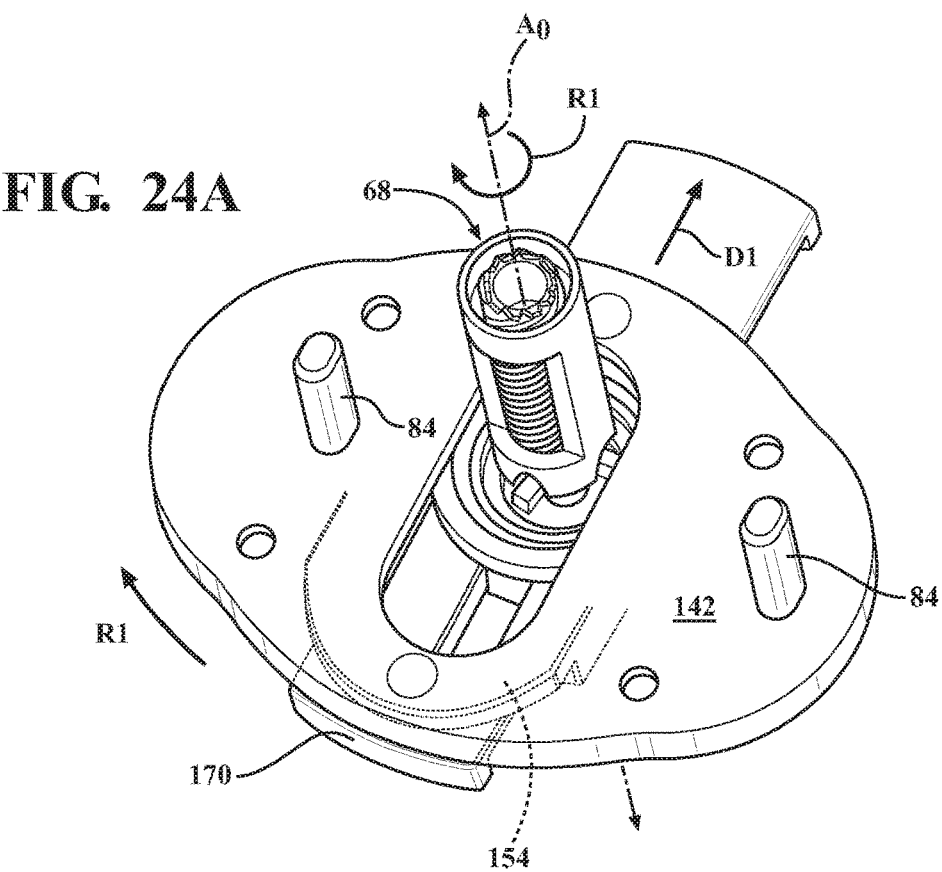
FIGS. 24A and 24B are an isolated perspective top view of a cam assembly corresponding to the preparation module of FIGS. 23A and 23B.
Figure 24B:
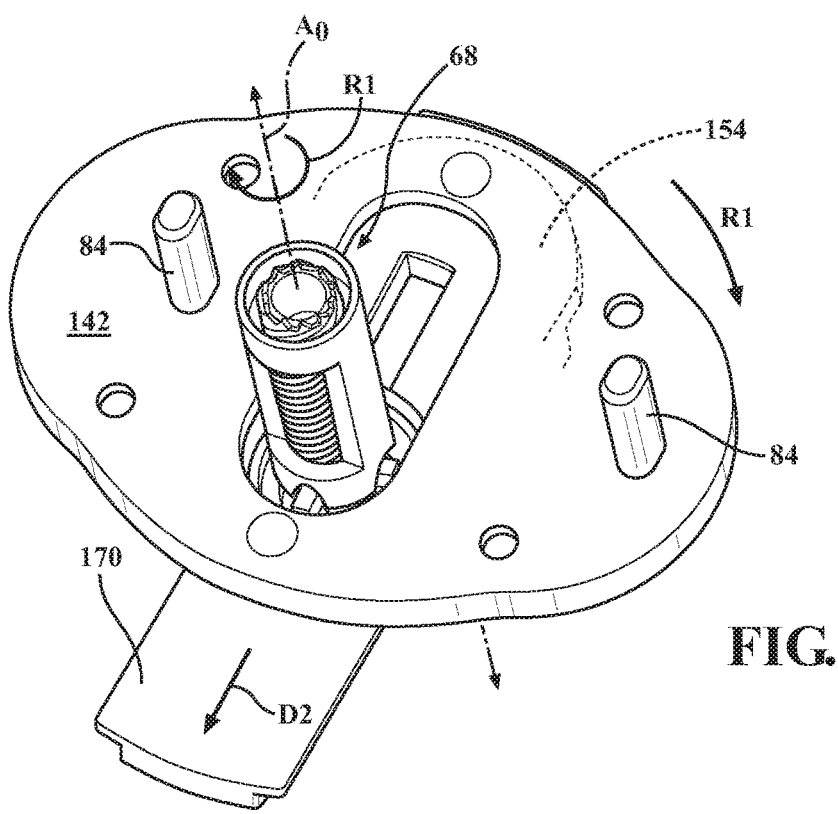

Referring now to FIGS. 23A and 23B, as the cam assembly is actuated, the cam follower 142 and the drive elements 82 mounted on the upper surface 144 thereof move from a first position to a second position linearly in a first direction $D_1$ in the one or more slots 103 in the mounting wall 102 and the corresponding one or more slots 80 in the base 54 of the preparation module 50 and move the carriage 62 linearly in a second direction $D_2$ (opposite D1) across the support surface 56 of the base 54 from a first position to a second position.

Referring now to FIGS. 24A, 24B, 25A, and 25B, during actuation of the cam assembly, the end tip 164 of the cam 154 moves along the first elongated segment 156 of the track 148. Once a side tip 166 and/or the end tip 164 of the cam 154 moves through the ensuing arcuate segment 160 and contacts the second elongated segment 158, the cam follower 142 is driven relative to the inner surface 108 of the mounting wall 102 and the cam follower 142 moves in the first direction $D_1$ from a first position to a second position relative to the inner surface 108 of the mounting wall 102. However, the cam follower 142 is set apart from and does not move across the inner surface 108 of the mounting wall 102. As is shown in FIGS. 24A, 24B, 25A, and 25B, as the cam 154 drives the cam follower 142 back and forth relative to the inner surface 108 of the mounting wall 102, the location of the drive shaft 152 within the drive slot 150 moves from a first end of the drive slot 150 to a second end of the drive slot 150. Notably, the drive shaft 152 is not moving laterally (just rotationally), rather the entire cam follower 142 is moving relative to the drive shaft 152, removal element 68, and the inner surface 108 of the mounting wall 102 and thus a position of the drive shaft 152 within the drive slot 150 changes. Likewise, as the cam follower 142 is driven in the first direction $D_1$, the one or more drive elements 82 mounted on the upper surface 144 of the cam follower 142 move in the first direction $D_1$ from a first position to a second position in the one or more slots 103 in the mounting wall 102 and the corresponding one or more slots 80 in the base 54 of the preparation module 50 and move the carriage 62 in the first direction $D_1$ linearly across the support surface 56 of the base 54 from a first position to a second position.

With further reference to FIGS. 23A and B, 24A and B, and 25A and B, the cam 154 continues to turn, like an arm on a clock, in the oblong track 148, along the second elongated segment 158. Once the side tip 166 and/or the end tip 164 of the cam 154 moves across the second elongated segment 158 and through the ensuing second arcuate segment 162, the cam follower 142 is driven relative to the inner surface 108 of the mounting wall 102 in the second direction $D_2$ from the second position back to the first position on the inner surface 108 of the mounting wall 102. As the cam 154 drives the cam follower 142 in the second direction $D_2$, a location of the drive shaft 152 within the drive slot 150 moves from the second end of the drive slot 150 back to the first end of the drive slot 150. Notably, the drive shaft 152 is not moving laterally (just rotationally), rather the cam follower 142 is moving linearly adjacent the inner surface 108 of the mounting wall 102 and thus a position of the drive shaft 152 within the drive slot 150 changes. Likewise, as the cam follower 142 is driven linearly, the one or more drive elements 82 mounted on the upper surface 144 of the cam follower 142 move in the second direction $D_2$ from the second position back to the first position in the one or more slots 103 in the mounting wall 102 and the corresponding one or more slots 80 in the base 54 of the preparation module 50, and move the carriage 62 linearly in the second direction $D_2$ across the support surface 56 of the base 54 from the second position back to the first position. Accordingly, when the system 42 is actuated, the carriage 62 within the preparation module 50 moves linearly, back and forth, across the support surface 56 of the base 54 within the preparation module 50.

Referring back to FIG. 6 as well as the schematics of FIGS. 23A and B, as is set forth above, the carriage 62 is moveably mounted in the void space 60 on the support surface 56 of the base 54. The base 54 typically includes one or more slots 80 with one or more drive elements 82 movably disposed therein, the one or more drive elements 82 being operatively attached to the drive train of the base 54. The drive elements 82 cooperate with a corresponding attachment element on the carriage 62. In the example carriage 62 of FIGS. 1-28, two drive element sleeves 84 are disposed on an outer surface 86 of the carriage housing 76 of the carriage 62. More specifically, the base 54 includes a first slot 80*a* and a second slot 80*b* parallel to the first slot 80*a*, wherein a first drive element 82*a* and a second drive element 82*b* are disposed in a first slot 80*a* and a second slot 80*b*. The drive elements 82*a*, 82*b* are operatively attached the drive train and the carriage 62, via insertion into a first drive element sleeve 84*a* and a second drive element sleeve 84*b* thereon. The drive elements 82*a*, 82*b* are configured to move from a first position to a second position within each of the first and second slots 80*a*, 80*b* to move the carriage 62 linearly across the support surface 56 of the base 54. Movement of the carriage 62 across the support surface 56 is further illustrated with the schematic diagrams of FIG. 23.

The drive train actuates both the carriage 62 (via the cam assembly described above) and the removal element 68. The drive shaft 152, which is disposed in the drive shaft opening 184 in the cam collar 172, includes a head 188 having an outer peripheral surface 192. The head 188 of the drive shaft 152 is configured or shaped to engage a foundation 198 of the removal element 68.

When the preparation module 50 is mounted on the mounting surface 106 of the pedestal 98, a mounting key 194 on the outer surface 110 of the base 54 extends into the central opening 105 in the mounting wall 102 of the pedestal 98. The drive shaft head 188 (or a spindle 185 attached thereto) is configured to engage the removal element 68.

In some examples, an alignment pin or a plurality of teeth on either the head 188 of the drive shaft 152 or a spindle 185 attached thereto) or foundation 198 of the removal element 68 engage a plurality of slots on either the head 188 of the drive shaft 152 or on the foundation 198 of the removal element 68.

The mounting key of the preparation module 50 is illustrated in FIG. 4. The mounting key 194 on the outer surface 110 of the base 54 engages the central opening 105 on the mounting surface 106 of the pedestal 98. When the preparation module is engaged with the pedestal 98 of the base module 44, the drive shaft 152 is releasably coupled to the removal element 568.

Figure 19:
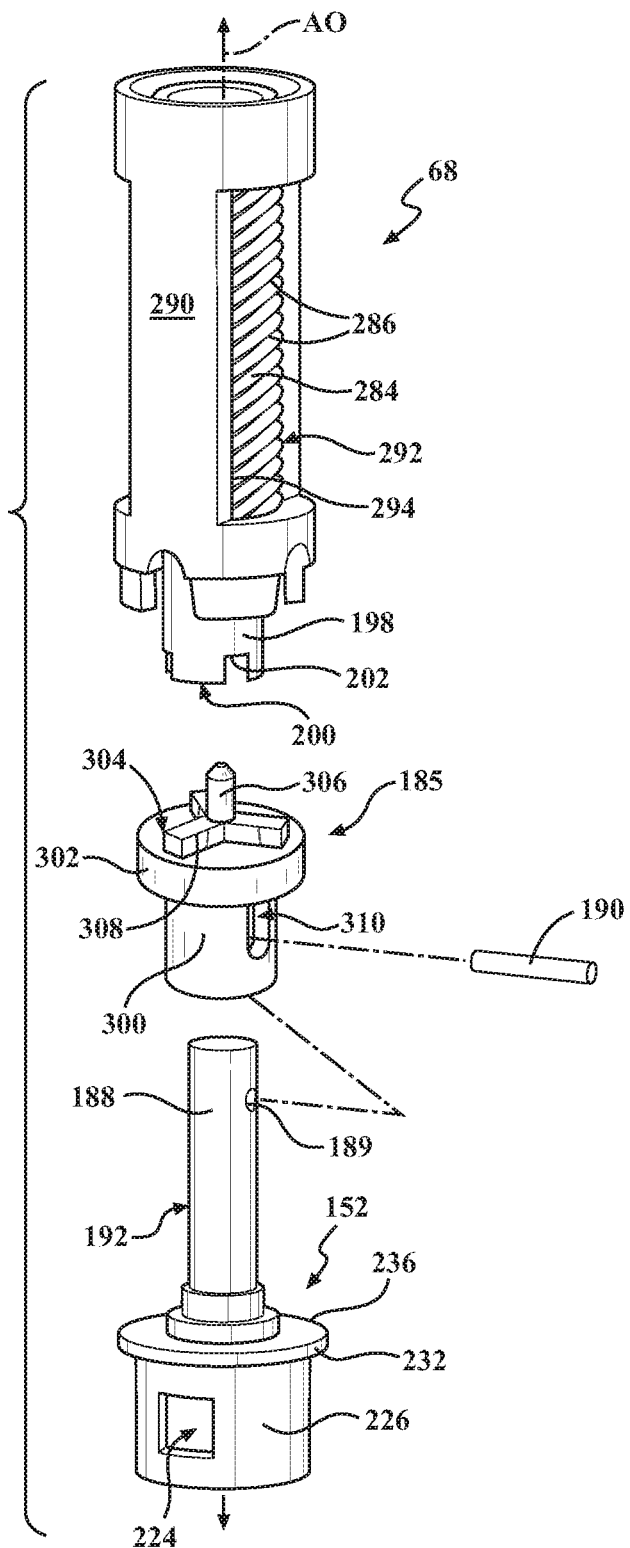
FIG. 19 is an exploded perspective view of the removal element and a drive shaft and features that releasably couple the removal element to the drive train.

Referring now to FIG. 19, the removal element 68 (e.g. fluted screw 284) includes a foundation 198 defining a centrally located opening 200 and a plurality of circumferentially and equiangularly spaced apart notches 202 distributed about the perimeter of the foundation 198.

The spindle 185 is coupled to and driven by the drive shaft 152. As is illustrated in FIG. 19, the spindle 185 includes a stem 300 that is cylindrical and a head 302 that is disc shaped and concentric with the stem. The spindle head 302 is circular and may be affixed to the stem 300, Alternatively, the spindle head 302 may be integrally formed with the stem 300.

Still referring to FIG. 19, a number of features extend upwardly from the planar top surface 304 of the spindle head 302. One of these features is an alignment pin 306. The alignment pin 306 is coaxial with the operational axis AO of the spindle 185 and projects upwardly from the center of the spindle head 302. The alignment pin 306 is cylindrical and extends past the planar top surface 304 of the spindle head 302. The terminal end of the alignment pin 306 is frustoconical and provided with a flattened tip. These features of the alignment pin 306 are not separately numbered.

In FIG. 19, a plurality of ridges 308 (three) extend radially from the alignment pin 306 on the planar top surface 304 of the spindle head 302 to the perimeter of the spindle head 302 and are three equiangularly spaced apart from one another. The plurality of ridges 308 do not extend as far as the alignment pin 306 does from the planar top surface 304 of spindle head 302.

When the preparation module 50 is mounted on the mounting surface 106 of the pedestal 98 of the base module 44, as is shown generally in FIG. 1, the alignment pin 306 on the spindle head 302 slideably engages the centrally located opening 200 on the foundation of the removal element 68 (e.g. fluted screw 284), and the plurality of ridges 308 (three) on the spindle head 302 engage a plurality of notches 202 (three) are equiangularly spaced apart and distributed about the perimeter of the foundation 198 and correspond with the plurality of ridges 308.

Referring now to FIG. 19, the spindle 185 is operably attached to the drive shaft 152. As just one example, the spindle 185 may be dimensioned and positioned so that the stem 300 is slideably received on the head 188 of the drive shaft 152. A drive pin 190, cylindrical in shape, is fitted into a cross bore 310 extending radially through the stem 300, and also through a cross bore 189 on the head of the drive shaft 188. The opposed ends of the drive pin 190 extend from the outer cylindrical surface of stem 300 and are disposed in the cross bore 189 on the head 188 of the drive shaft 152. As such, there is little or no relative angular movement between the drive shaft 152 and the stem 300 that is coaxial therewith. Rotation of the drive shaft 152, induced by the motor 46 is imparted to the stem 300 via abutting engagement between drive pin 190 and the sides of the bores). The operative attachment of the spindle 185 with the drive shaft 152 (in this example the engagement between cross bores 189, 310 and drive pin 190) retains the spindle 185 to the drive shaft 152 and transfers torque therebetween. As such, the spindle 185 rotates in unison with the drive shaft 152 to power the removal element 68.

When the preparation module 50 is mounted on the mounting surface 106 of the pedestal 98, as is shown generally in FIG. 1, the mounting key 194 on the outer surface 110 of the base 54 extends into the central opening 105 in the mounting wall 102 through the drive slot 150 on the cam follower 142, through the central drive opening 174 of the cam 154, through the central drive opening 176 on the cam carrier 170 to engage the spindle 185.

As set forth above, the drive train actuates both the carriage 62 (via the cam assembly described above) and the removal element 68 (via the spindle 185). These elements are described throughout FIGS. 1-28. However, an isolated view of the connection between the drive train (including the cam assembly) and the carriage is not specifically illustrated in FIG. 19.

Figure 20:
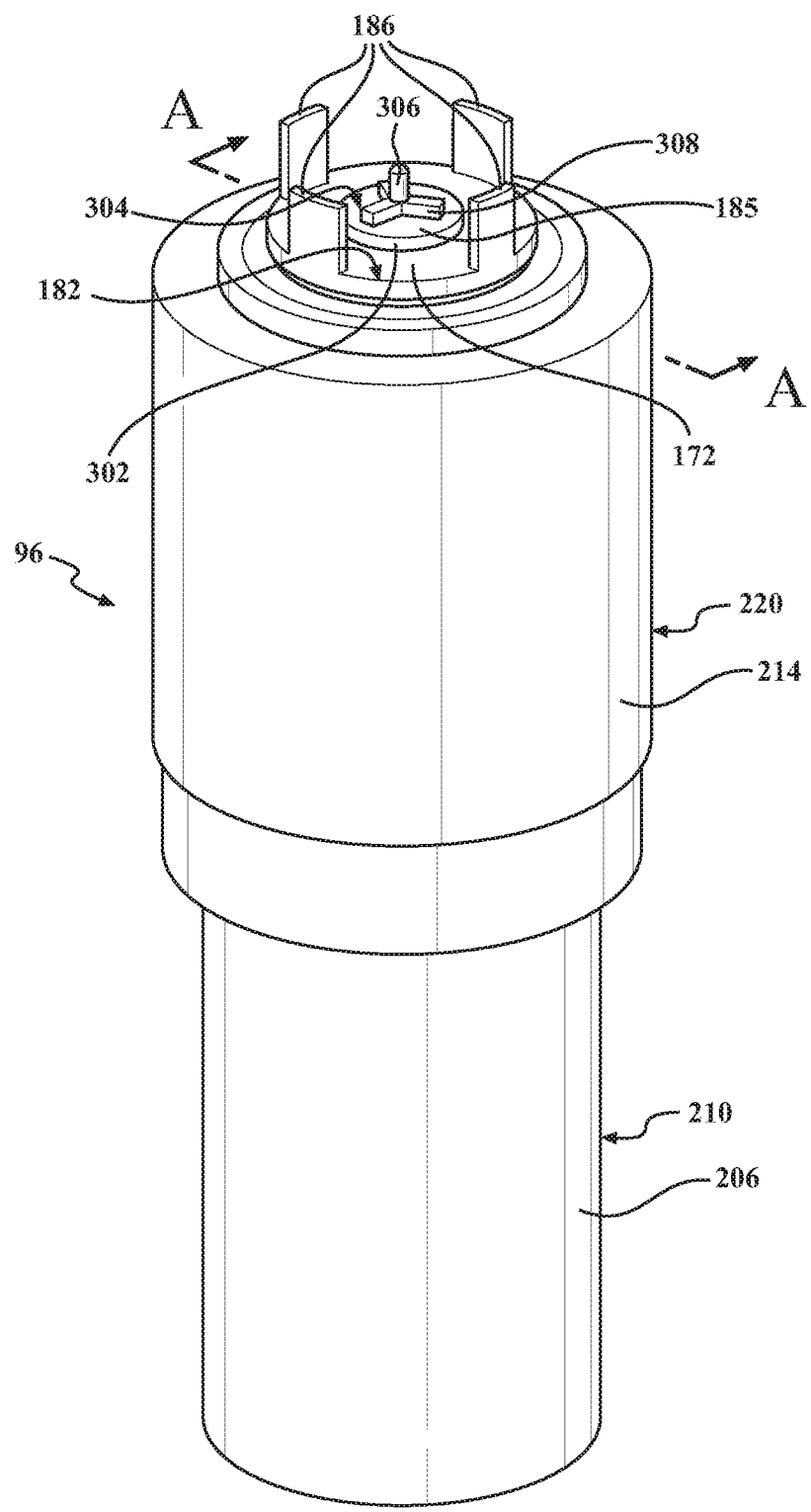
FIG. 20 is an isolated perspective view of the drive module of the base module of the system of FIG. 1.
Figure 21:
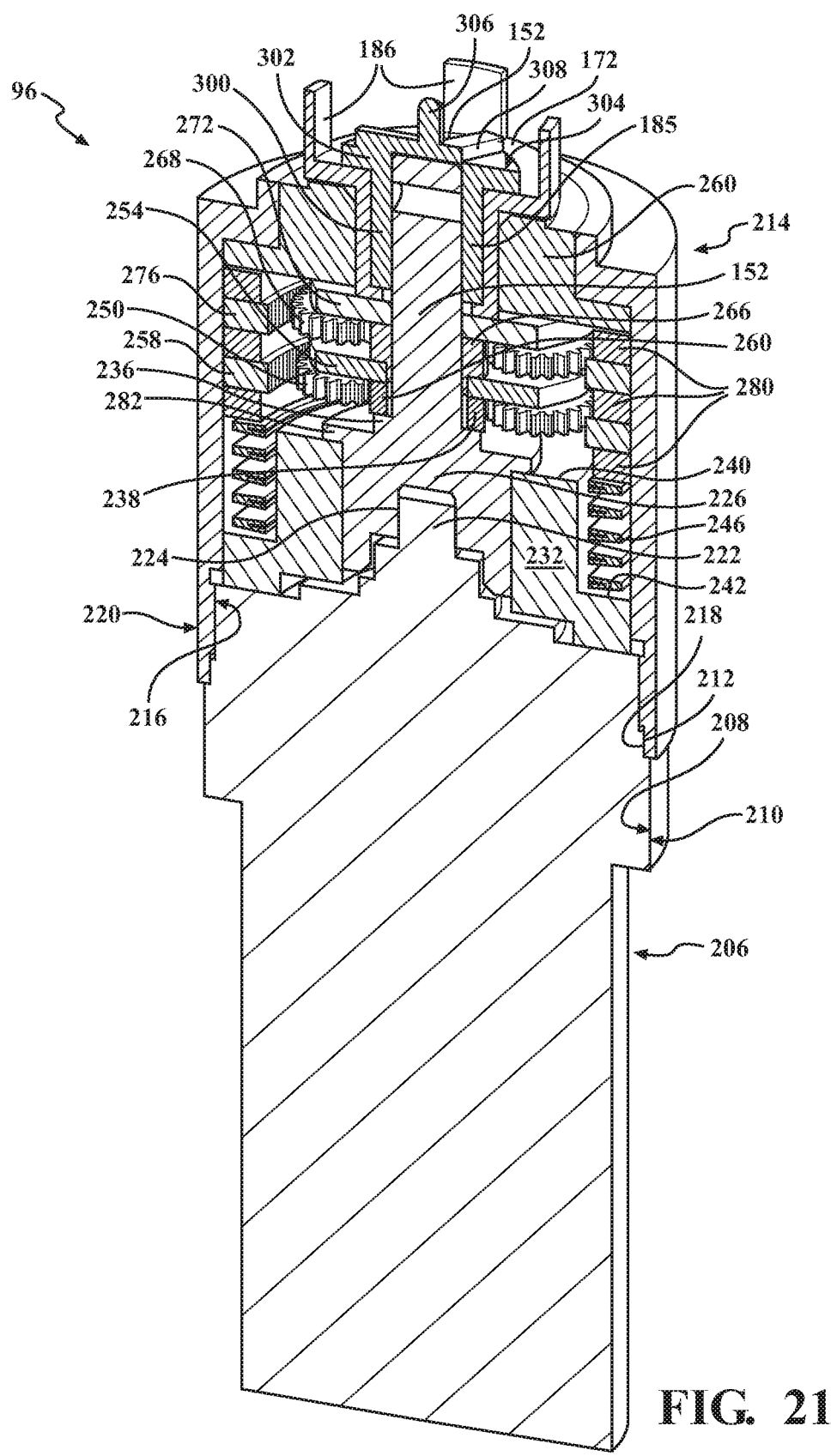
FIG. 21 is a cross-sectional view of the drive module of FIG. 20 along A-A.
Figure 22:
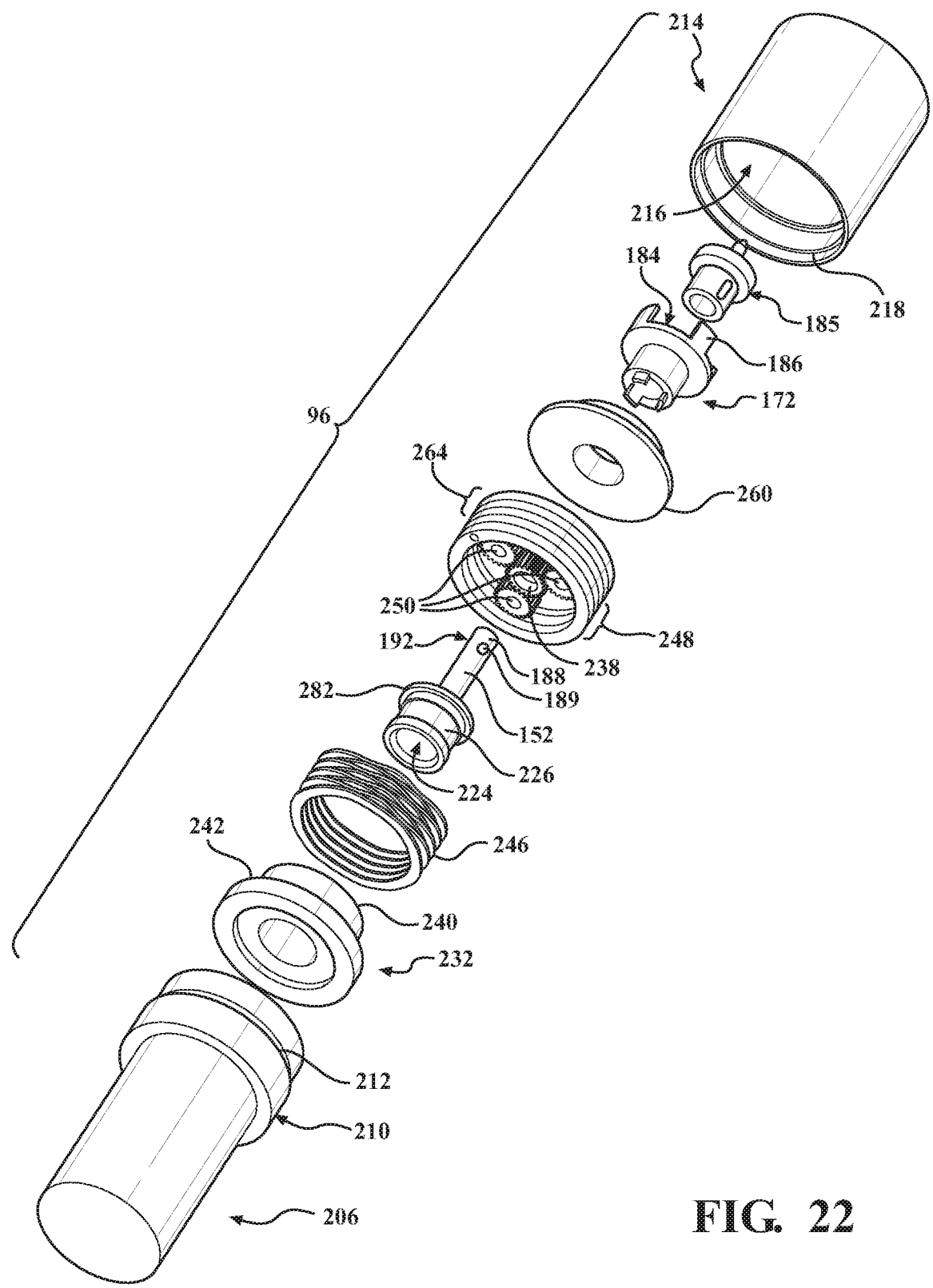
FIG. 22 is an exploded perspective view of the drive module of FIG. 13.

An isolated perspective view of the drive module 96 is set forth in FIG. 20, a cross-sectional view of the drive module 96 of FIG. 20 along A-A is set forth in FIG. 21, and an exploded view of the drive module 96 of FIG. 20 is set forth in FIG. 22. Referring now to FIGS. 20-22, the drive shaft 152 transfers rotational energy directly to the removal element 68 at a first speed (e.g. in RPM's), and the cam collar 172 transfers rotational energy to the cam assembly (via the cam carrier 170) at a second speed which is slower than the first speed. Of course, the cam assembly ultimately drives the drive module 96 which is disposed in the preparation chamber 66 linearly across the support surface 56 of the base 54 which provides synergistic interaction between the plurality of articulating wall segments 70 and the removal element 68 to optimize preparing of bone stock in the preparation chamber 66.

Referring now to FIGS. 20-22 or back to FIGS. 12 and 13, a lower housing 206 on the drive module 96 houses the motor. The lower housing 206 has an inner surface 208 and an outer surface 210. The drive module 96 also has an upper housing 214 having an inner surface 216 and an outer surface 220. Notably, drive shaft 152, the spindle 185, the cam collar 172, a spacer 260, and the upper housing 214 are visible in FIGS. 20 and 21 as an upper surface of the cam the module 96. The cam collar 172, which drives the cam assembly, moves separately from the drive shaft 152, which drives the removal element 68, with the spindle 185 (FIG. 18 illustrates the connection between the cam collar 172 and the cam assembly (the cam carrier 170)). In FIG. 21, the spacer 260 is disposed between the cam collar 172 and the inner surface 216 of the upper housing 214 to separate moving elements, e.g. the cam collar 172, and non-moving elements, e.g., the upper housing 214. The cam collar 172, the spindle 185, and the spacer 260 are typically formed from a low friction or low surface energy polymer such as polyethers, (e.g. polyoxyethylene), polyolefins (e.g. polyethylene (HDPE, LDPE, UBMWPE, etc.), polyamides, polyaryletherketones (e.g. PEEK), silicones, or polyesters (e.g. PET). As such, these elements, 172, 185, 260 function as a low friction interface.

Referring now to FIG. 22, the lower housing 206 may be configured to be releasably coupled to an upper housing 214. In the example illustrated a protrusion 218 on the inner surface 216 of the upper housing 4 snap fits into a groove 212 on the outer surface 210 of the lower housing 206.

Referring now to FIG. 22, an upper surface of the lower housing 206 includes a drive key 222, which engages a corresponding key hole 224 in a base 226 of the drive shaft 152, which is disposed in the upper housing 214. In the example illustrated, the drive key 222 has a rectangular profile and the key hole 224 defines a rectangular void. As such, when the drive key 222 engages in the key hole 224, the configuration allows the transfer of rotational energy from the motor 46 to the drive shaft 152. To this end, when the upper and lower housing 214, 206 are coupled, the drive key 222 is engaged in the key hole 224 in the base 226 of the drive shaft 152 which is disposed in the upper housing 214, the motor 46 turns the drive shaft 152. The motor 46 produces torque and rotation and the engaged drive shaft 152 is configured to connect other components of the drive train that may not be connected directly to the motor 46 because of the need for rotational energy at different speeds and in different directions, the need to convert rotational movement into linear movement, the need to convey the rotation over a distance, etc.

Referring now to FIG. 21, a base collar 232 is radially disposed about an outer peripheral surface of the base 234 of the drive shaft 152. The drive shaft 152 includes an upper shelf 236, upon which a first sun gear 238 sits, and a collar 282. The base collar 232 has an inner shelf 240 upon which the collar 282 of drive shaft 152 sits, and an outer shelf 242 upon which a spring 246 sits. The spring 246 acts as a tensioner to provide give and help prevent the binding-up of a gear train, which ultimately powers the cam assembly and moves the carriage 62.

The gear train includes a first reduction 248 including the first sun gear 238 which is disposed radially about the drive shaft 152 and sits on the upper shelf 236, first planetary gears 250 (three) which cooperate with the first sun gear 238, a first carrier 254 which carriers the first planetary gears 250, and a first ring gear 258 which cooperates with the first planetary gears 250. The first sun gear 238 is operably attached to the drive shaft 152. A spacer 260 separates drive shaft 152 from the gear train. Accordingly, the first carrier 254 is disposed radially about the spacer 260. Although not shown, the first carrier 254 has a triangular shape and includes three first pin slots located on its three apexes. Three first pins are inserted into each of the three first pin slots and extend through the first carrier 254 distally along the operational axis AO and into each of three first central pin slots on the three first planetary gears 250. As rotational energy is passed along the gear train and through the first reduction 248, rotational speed is reduced relative to the speed of the drive shaft 152.

The gear train includes a second reduction 264 including a second sun gear 266 which is disposed radially about the spacer 260, three second planetary gears 268 which cooperate with the second sun gear 266, a second carrier 272 which carries the second planetary gears 268, and a second ring gear 276 which cooperates with the second planetary gears 268. Although not shown, the second carrier 272 has a triangular shape and includes three second pin slots located on its three apexes. Three second pins are inserted into each of the three second pin slots and extend through the second carrier distally along the operational axis AO and into each of three second central pin slots on the three second planetary gears 268. As rotational energy is passed along the gear train and through the second reduction 264, rotational speed is further reduced. As such, the collar 172, which provides rotational energy to the cam assembly, is rotating at a lower rotational speed than the drive shaft 152, which provides rotational energy to the removal element 68.

The first and second ring gears 258, 276 are radially disposed in alternate with three spacers 280 about an exterior of the drive assembly. The first and second ring gears 258, 276 and spacers 280 are disposed on an inner surface 216 of the upper housing 214 of the drive module 96. The spring 246, which is sandwiched between the outer shelf 242 on the base collar 232 and a lower of the three spacers 280 act as a tensioner to provide greater tolerance, allow slight movement, and prevent seizing of the gear train. It is to be appreciated that various other and gear trains and configurations can be utilized in the drive train of the subject disclosure.

The lower housing 206 having the motor 46 therein includes components, which are configured to engage the motor 46 and the drive shaft 152. In a typical example, an upper surface of the lower housing 206 includes a drive key 222, which engages a corresponding key hole 224 in a base of the drive shaft 152. When the drive key 222 is engaged in the key hole 224 in the base 226 of the drive shaft 152, the motor 46 turns the drive shaft 152. The collar 282 is circumferentially disposed about the base 226 of the drive shaft 152. The drive key 222 is engaged in the key hole 224 in the base 226 of the drive shaft 152, the motor 46 turns the drive shaft 152 when the base 226 of the drive shaft 152 is engaged with the drive key 222 of the lower housing 206.

In some examples, the motor 46 and the drive train are collectively provided so that the drive shaft 152 rotates at speeds between 100 and 500 RPM. These speeds are the under-load speeds at which the drive shaft 152 rotates during operation of the system 42 when bone stock is disposed and being prepared in the carriage 62.

In FIGS. 23-25, three schematics describe exemplary movement of the carriage 62 and the removal element 68 which are driven by the motor 46 and the drive train as described above. FIG. 23 is an isolated perspective top view of the carriage 62 moveably disposed on the support surface 56 of the base 54, with the removal element 68 disposed in the preparation chamber 66. In FIG. 23, the carriage 62 is illustrated moving linearly in the first direction $D_1$ and the second direction $D_2$ across the support surface 56 of the base 54. As is explained above, rotational energy from the drive shaft 152 is reduced in the gear assembly and then converted into linear motion with the cam assembly, which powers the carriage 62. In FIG. 23, the removal element 68 includes the fluted screw 284 rotatably disposed in the preparation chamber 66 and moving in a first rotational direction $R_1$ (clockwise) and also a windowed shaving tube 290 disposed about the fluted screw 284. The windowed shaving tube 290 is mounted to the base 54 and is fixed, i.e., does not move rotationally in this example. The carriage 62 and the fluted screw 284 of the removal element 68 move concurrently.

Referring now to FIG. 24, the movement of the cam follower 142 having the two drive elements 84, which drive the carriage 62, is illustrated. As explained previously, the carriage 62 moves with the cam follower 142 because it is operably attached to the drive elements 84 of the cam follower 142. FIG. 24 is an isolated perspective top view of the cam follower 142, the cam 154, and the cam carrier 170. As the cam 154 and the cam carrier 170 move in a first rotational direction $R_1$ (clockwise), the cam follower 142 moves linearly, back and forth, in directions $D_1$ and $D_2$. The movements illustrated in FIG. 24 correspond to those in FIG. 23 such that FIG. 24 shows the cam assembly of FIG. 23 without the carriage 62 and the base 54 visible. To this end, FIG. 24 illustrates the movement of the cam assembly as it relates to the position of the carriage 62 on the support surface 56 of the base 54 illustrated in FIG. 23. In FIG. 24, as the cam 154 drives the cam follower 142 linearly, the location of the drive shaft 152 within the drive slot 150 of the cam follower 142 moves from a first end of the drive slot 150 to a second end of the drive slot 150 (the cam follower 142 is moving and not the drive shaft 152). Concurrently to the linear movement of the cam follower 142 and the carriage 62, the fluted screw 284 is also illustrated moving in a first rotational direction $R_1$ (clockwise).

Referring now to FIG. 25, the movement of the cam 154 around the track 148, which causes the linear movement of the cam follower 142 and drive elements 82 thereon to drive the carriage 62, is illustrated. As explained previously, the carriage 62 moves with the cam follower 142 because it is operably attached to the drive elements 82 of the cam follower 142. FIG. 25 is an isolated perspective bottom view of the cam follower 142 and the cam 154. As the cam 154 moves in a first rotational direction $R_1$ (clockwise) around the track 148, the cam follower 142 moves linearly, back and forth, in directions $D_1$ and $D_2$. The movements illustrated in FIG. 25 correspond to those in FIGS. 23 and 24 such that FIG. 25 shows the cam assembly of FIG. 23 and FIG. 24 from a bottom view. To this end, FIG. 25 illustrates the movement of the cam 154 on the track 148 of the cam follower 142 as it relates to the position of the carriage 62 on the support surface 56 of the base 54 illustrated in FIGS. 23 and 24. In FIG. 25, the fluted screw 284 is also illustrated concurrently moving in a first rotational direction $R_1$ (counter-clockwise because of the bottom view).

In FIG. 26, a schematic diagram is set forth which describes the movement of the upper and lower leg components 120, 118 to adjust the height relative to the mounting surface $M_s$, of the preparation module 50 by a user. FIG. 19 describes the incremental movement of the preparation module 50 for use at a desired angle $\Theta$ along the operational axis AO and relative to the mounting surface $M_s$.

A further feature of this disclosure is that a detection component may be attached to the preparation module 50. If included, a complementary sensor in the pedestal 98 of the base module 44 detects the presence/absence of the detection component. If the presence of the detection component is not detected, the electronic control system interprets the system 42 as being in a non-operation state and will not allow the preparation module 50 to be actuated.

The system 42 may also be configured to operate with a milling module (not illustrated), which may be utilized to mill the prepared bone stock into bone fragments which are used as bone graft. Like the preparation module 50, the milling module may be removably attached to the base module 44.

In advance of additional description regarding components of the system 42, it is to be appreciated that all of the different and exemplary components set forth throughout this disclosure may be used interchangeable and full support and consideration for such interchangeable use is included herein. For example, any particular example of the wall 64 (e.g. a resilient and/or articulating wall 64 including various segment 70 amounts, shape, and material combinations) is contemplated for use with any example of the removal element 68 (brush, fluted screw 284 and shaving tube 290, etc.), both of which are contemplated with any configuration of preparation module 50 (including the cam assembly internally, or not including the cam assembly because it is located in the base module 44).

The main difference between the system 42 illustrated in FIGS. 1-28 and the system 542 illustrated in FIGS. 29-41 is that the cam assembly of the drive train 548 is located in a preparation module 550 as opposed to being located in a pedestal 598 of a base module 544.

Figure 29:
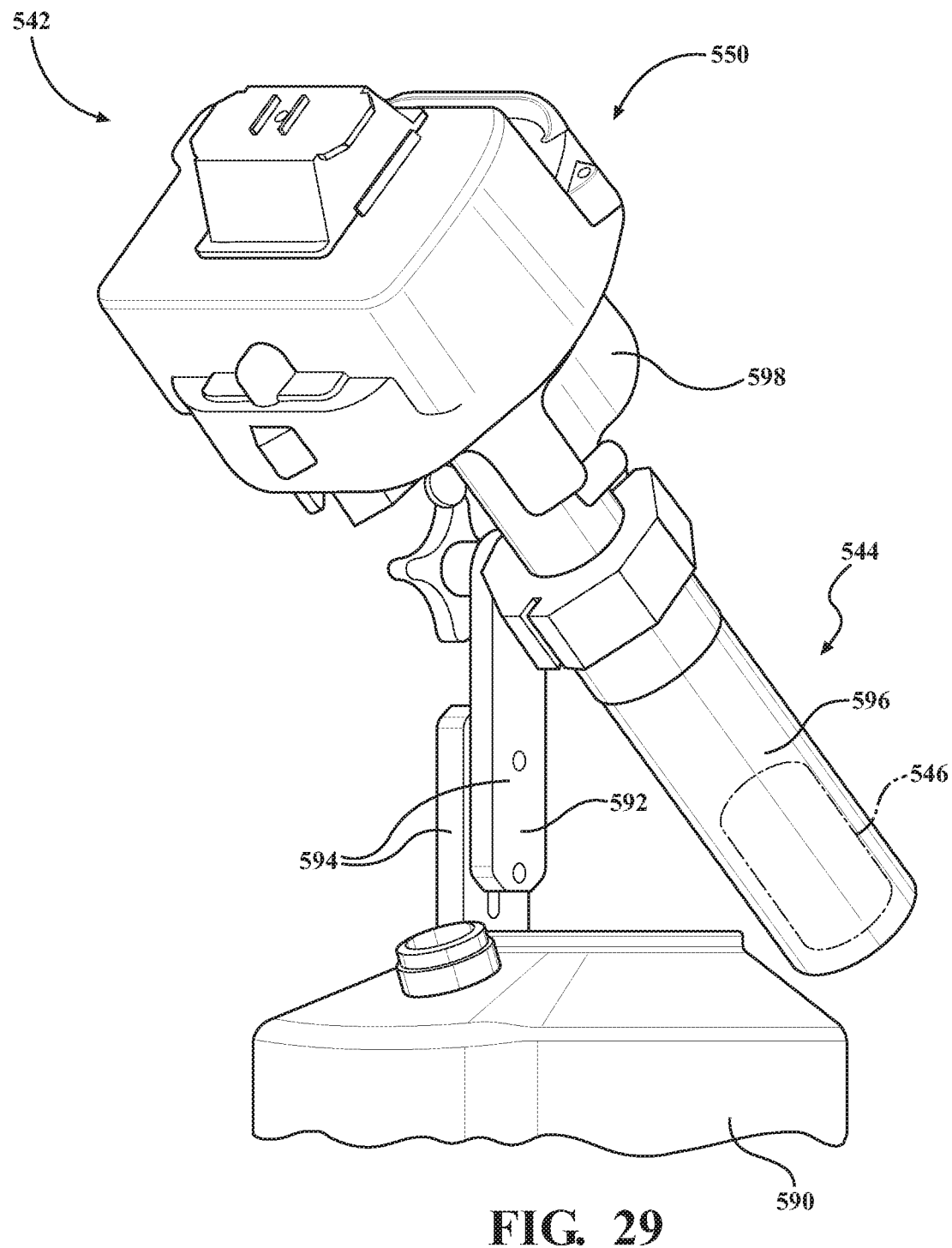
FIG. 29 is a perspective view of another modular system for preparing bone stock with a preparation module attached to a base module.
Figure 30:
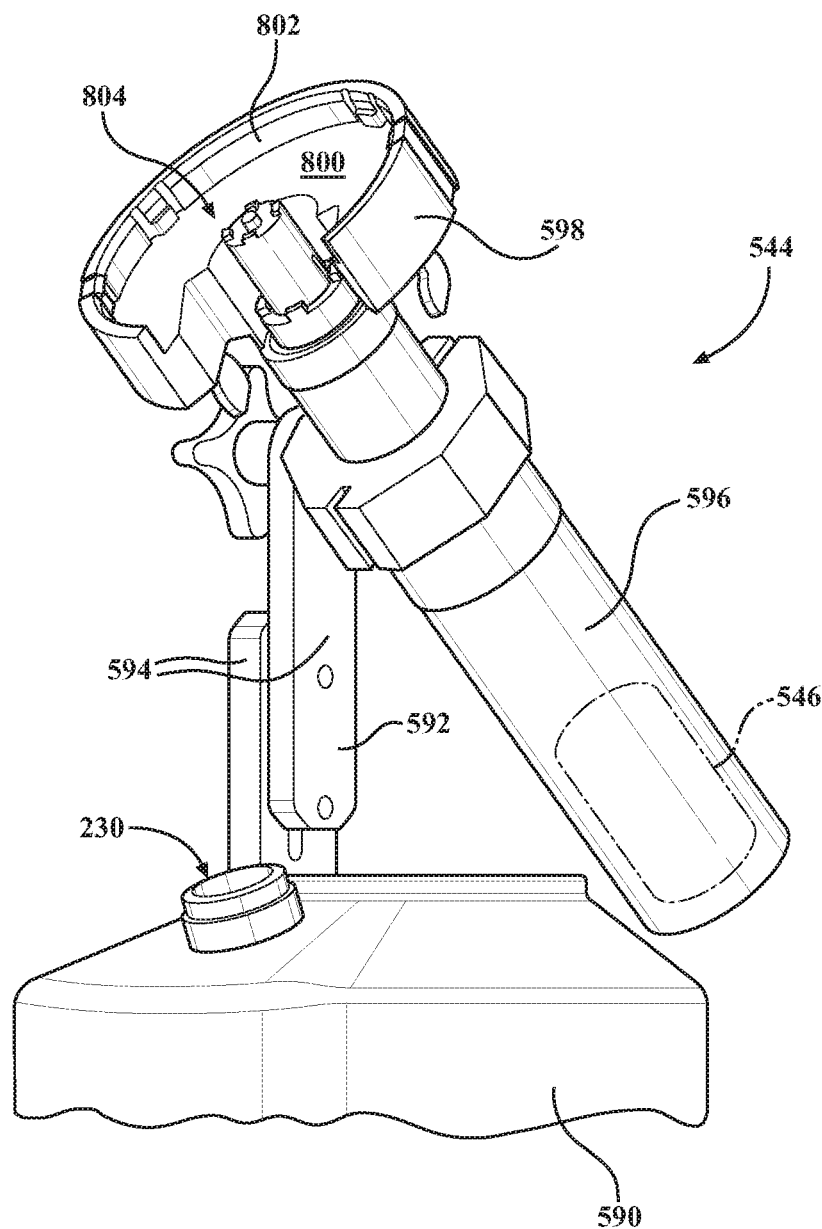
FIG. 30 is a perspective view of the base module of the system of FIG. 29 with the preparation module detached.

FIG. 29 is a perspective view of the base module 544 of the system 542 with the preparation module 550 attached to the base module 544. FIG. 30 is a perspective view of the base module 544 of the system 542 of FIG. 29 with the preparation module 550 detached, while FIG. 31 is an isolated perspective view of the pedestal 598 and the drive module 596 of the base module 544 and FIG. 32 is a cross-sectional view of the pedestal 598 and the drive module 596 along line A-A.

Figure 31:
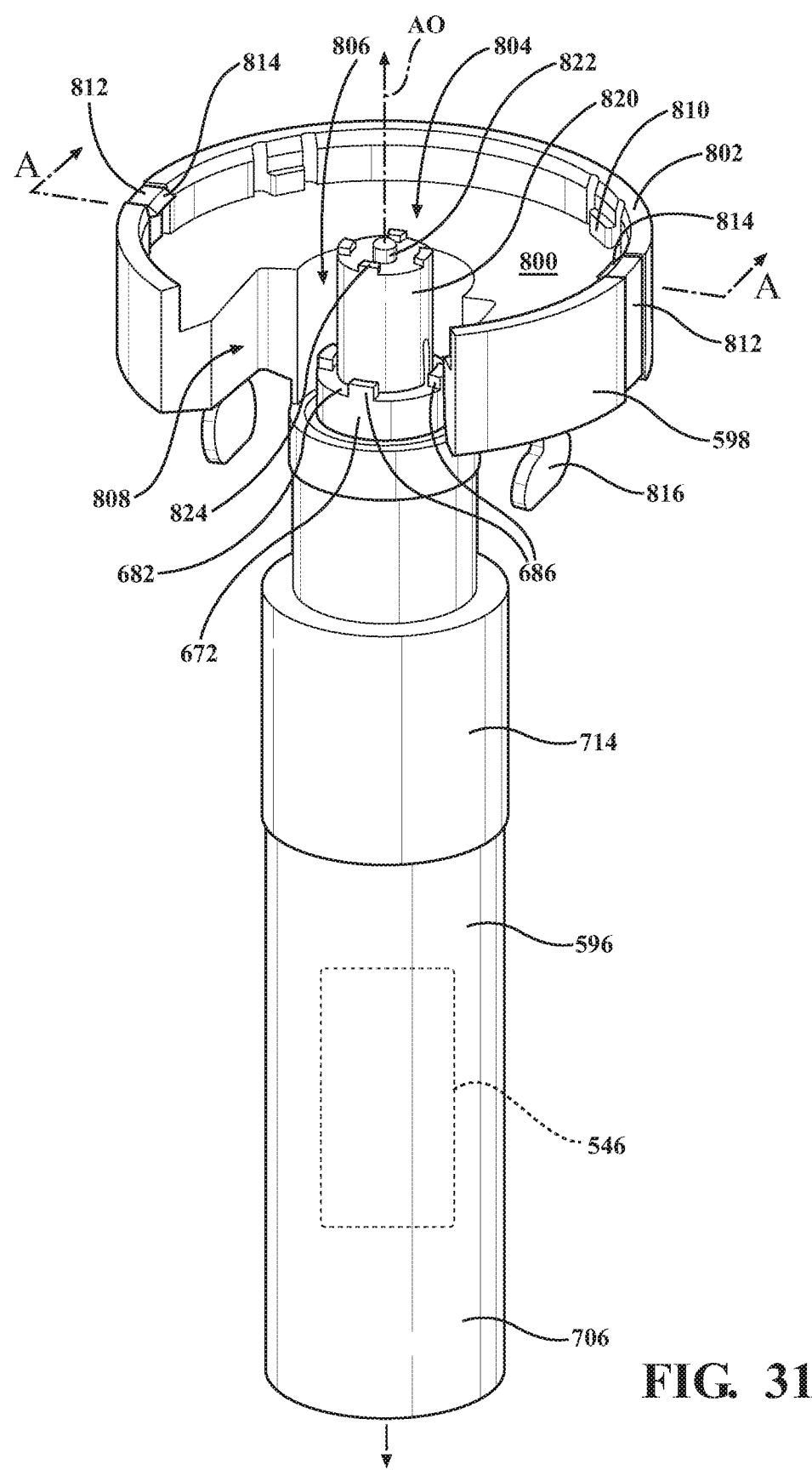
FIG. 31 is an isolated perspective view of the pedestal and the drive module of the base module of the system of FIG. 29.
Figure 32:
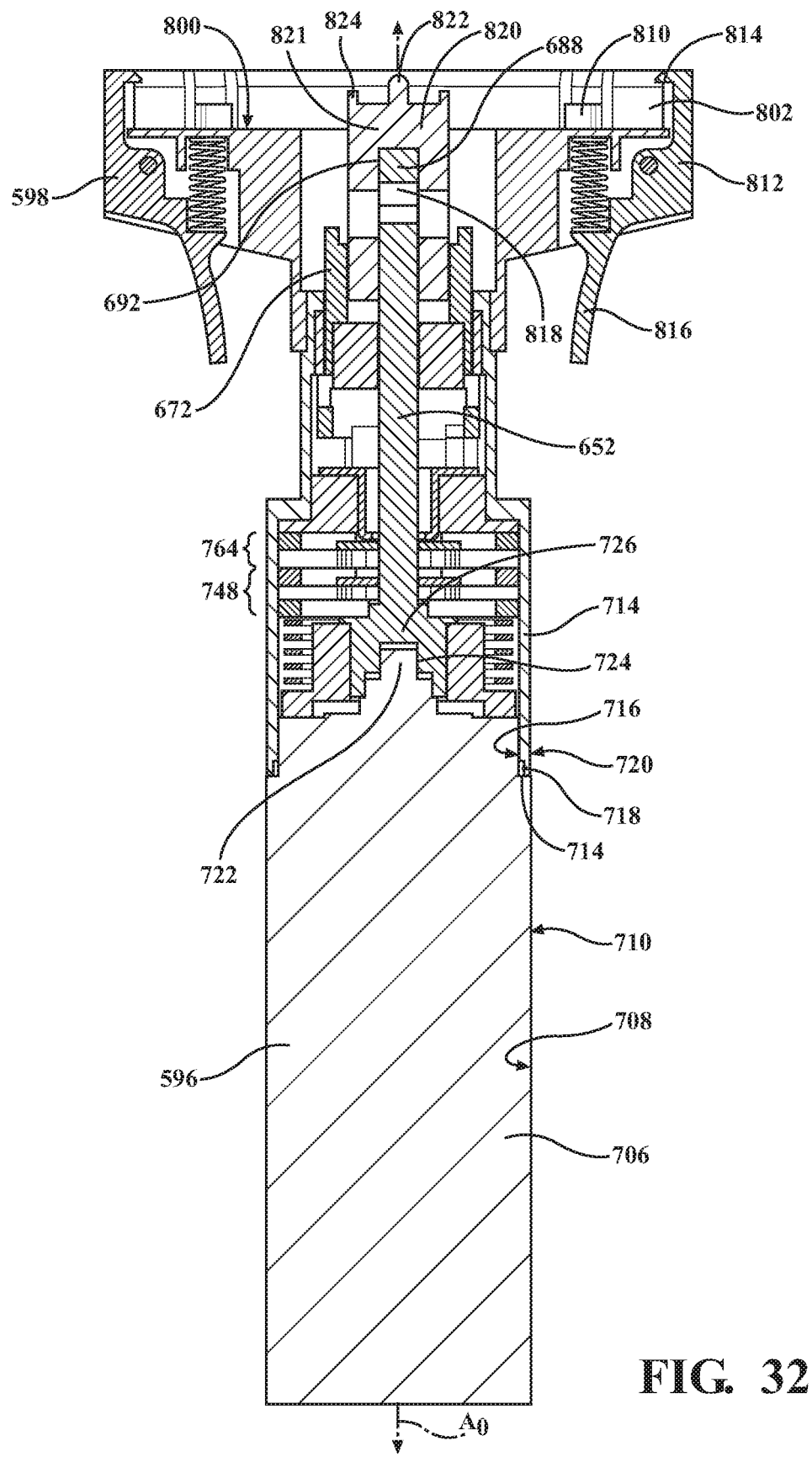
FIG. 32 is a cross-sectional view of the pedestal and the drive module of FIG. 31 along line A-A.

Referring now to FIGS. 30 and 31, the system 542 includes the base module 544. Internal to the base module 544 is a motor 546 and the drive train 548. The preparation module 550 is removably attachable to the base module 544. In the example illustrated in FIG. 29, the base module 544 is reusable, and the preparation module 550 is disposable or reusable (configured to be cleaned and to be autoclaved).

Referring now to FIG. 30, the base module 544 includes a foot 590. A leg 592 extends upwardly from the foot 590. The leg 592 supports a drive module 596 having a pedestal 598 thereon. The leg 592 includes two segments 594 with connection features, which allow a user to adjust the height of the preparation module 550 relative to a working surface.

Still referring to FIGS. 30 and 31, the pedestal 598 has a mounting surface 800 that is circular. The pedestal 598 is further formed to have a lip 802 that extends upwardly and extends about a perimeter of the mounting surface 800. The mounting surface 800 and the radially inner surface of lip 802 define the mounting surface 800 within the pedestal 598. A mounting space 804 is open at the top of the pedestal 598. The outer circumference of the lip 802, which is the outer circumference of the pedestal 598, is smaller than a circumference of the foot 590. The pedestal 598 is further formed to have a center opening 806 in the center of the mounting surface 800.

Referring to FIG. 31, a notch 808 extends radially inwardly from the outer circumference of pedestal 598. The notch 808 thus forms a break in the lip 802. In the illustrated example, the notch 808 extends radially inwardly to the center opening 806. The pedestal 598 further includes a number of circumferentially and equiangularly spaced apart teeth 810 (only two teeth illustrated in FIG. 31). Each tooth 810 extends upwardly from the mounting surface 800 adjacent the lip 802.

Referring still to FIGS. 31 and 32, two retention arms 812 are pivotally mounted to the pedestal 598. The retention arms 812 are diametrically opposed and mounted to the pedestal 598 in cutouts formed in the lip 802 (cutouts not separately numbered). Each retention arm 812 has a finger 814 that, when the arm 812 is at rest, extends over a portion of the perimeter of the mounting surface 800. When the retention arms 812 are so positioned, the arms 812 are in the "locked" state.

As is illustrated in FIG. 32, each retention arm 812 has a lever 816 located below the pedestal 598. By moving the lever 816 radially inwardly, towards the underside of the pedestal 598, the associated retention arm 812 is pivoted relative to the pedestal 598 to move the corresponding finger 814 away from its position over the mounting surface 800 and out of its locked state. When the retention arms 812 are so positioned, the arms 812 are in the "released" state.

A biasing device such as a spring (not illustrated) is disposed between an inner surface of the pedestal 598 and each arm 812. The spring biases its respective retention arm 812 towards its locked state. Each retention arm 812 may be biased into its locked state by a dedicated spring. Alternatively, both retention arms 812 may be biased into their locked states by a common, shared spring.

Referring still to FIG. 32, the drive train 548 is disposed partially in the drive module 596, the pedestal 598, and the preparation module 550. The drive train 548 actuates both a carriage 562 (via a cam assembly included in the preparation module 550 in this example) and a removal element 568. The preparation module 550 is described below and illustrated in FIGS. 33-40. Still referring to FIG. 32, the drive shaft 652, which is disposed in the central opening in the collar 672, includes a drive shaft head 688 having an outer peripheral surface 692. The drive shaft head 688 of the drive shaft 652 is configured or shaped to engage a spindle head 820, which is configured to engage the removal element 568. Regarding engagement, the drive shaft head 688 is disposed in the drive shaft opening in the collar 672 and extends therethrough while the spindle head 820, which is on the drive shaft head 688, extends into a center opening 806 of the pedestal 598.

Referring to FIGS. 31 and 32, the drive shaft 652 transfers rotational energy directly to the removal element 568 at a first speed (e.g. in RPM's), and the collar 672 transfers rotational energy to the cam assembly at a second speed which is slower than the first speed.

Referring still to FIGS. 31 and 32, a lower housing 706 on the drive module 596 houses the motor 546. The lower housing 706 has an inner surface 708 and an outer surface 710. The drive module also has an upper housing 714 having an inner surface 716 and an outer surface 720. Notably, the collar 672 is visible in the notch 808.

Referring to FIG. 32, the lower housing 706 is configured to be releasably coupled to the upper housing 714. In the example illustrated a protrusion 718 on the inner surface 716 of the upper housing 714 snap fits into a groove 712 on the outer surface 710 of the lower housing 706.

Still referring to FIG. 32, an upper surface of the lower housing 706 includes a drive key 722, which engages a corresponding key hole 724 in a base 726 of the drive shaft 652, which is disposed in the upper housing 714. In the example illustrated, the drive key 722 has a rectangular profile and the key hole 724 defines a rectangular void. As such, when the drive key 722 engages in the key hole 724, the configuration allows the transfer of rotational energy from the motor 546 to the drive shaft 652. To this end, when the upper and lower housing 714, 706 are coupled, the drive key 722 is engaged in the key hole 724 in the base 226 of the drive shaft 652 which is disposed in the upper housing 714, the motor 546 turns the drive shaft 652. The motor 546 produces torque and rotation and the engaged drive shaft 652, is configured to connect other components of the drive train 548 that may not be connected directly to the motor 546 because of the need for rotational energy at different speeds and in different directions, the need to convert rotational movement into linear movement, the need to convey the rotation over a distance, etc.

Still referring to FIG. 32, the drive module 596 comprises a gear train including a first and a second reduction 748, 764 similar to the gear train described above and familiar to those skilled in the art of gearing. For the sake of brevity, a description of a functional gear train may be found above or in the disclosure of U.S. Pat. No. 9,687,361, the disclosure of which is included herein by reference.

As is set forth above, the motor 546 and the gear train are collectively provided so that the drive shaft 652 rotates at speeds between 100 and 500 RPM. These speeds are the under-load speeds at which the drive shaft 652 rotates during operation of the system 542 when bone stock is disposed in the carriage 562.

The drive spindle 820 is coupled to and driven by the drive shaft 652. In FIG. 32, the drive spindle 820 includes a stem 818 that is cylindrical and a concentric, disc shaped head 821. The spindle head 820 is circular and may be affixed to the stem 818. Alternatively, the spindle head 820 may be integrally formed with the stem 818.

Still referring to FIGS. 31 and 32, a number of features extend upwardly from the planar top surface of the spindle head 820. One of these features is an alignment pin 822. The alignment pin 822 is coaxial with the operational axis AO of the spindle 820 and projects upwardly from the center of the spindle head 820. The alignment pin 822 is cylindrical and extends past the planar top surface of the spindle head 820. The alignment pin 822 may be formed on the axial end of the stem 818 and project through the center of the spindle head 820. Alternatively, the alignment pin 822 and spindle head 820 may both be integrally formed with the stem 818. Alternatively, the alignment pin 822 and the spindle head 820 may be integrally formed and affixed to the axial end of the stem 818. The terminal end of the alignment pin 822 is frustoconical and provided with a flattened tip. These features of the alignment pin 822 are not separately numbered.

In FIG. 32, four circumferentially and equiangularly spaced apart drive teeth 824 also extend upwardly from the planar top surface of the spindle head 820. The drive teeth 824 are distributed about the perimeter of the spindle head 820. The drive teeth 824 have arcuate, radially outer surfaces that are flush with the radially outer circular edge of the spindle head 820. The drive teeth 824 also have arcuate, radial inner surfaces. Extending between the radially outer and inner surfaces of each drive tooth 824 is a pair of circumferentially opposite, inwardly tapered side surfaces; these surfaces of drive teeth 824 are planar and perpendicular to the planar top surface of the spindle head 820 and are not separately numbered. Drive teeth 824 do not extend as far as the alignment pin 822 does from the planar top surface of spindle head 820.

The spindle head 820 is operably attached to the drive shaft 652. As just one example, the spindle head 820 may be dimensioned and positioned so that the stem 818 is slideably received in the coaxial, longitudinal bore of the drive shaft 652. A cylindrical drive pin is fitted into a cross bore (not separately numbered) extending radially through the stem 818. The opposed ends of the drive pin extend from the cylindrical surface of stem 818 and are disposed in the diametrically opposed slots formed in the drive shaft 652. Near its opposite ends, the drive pin abuts and slideably engages the circumferentially interfacing elongate sides of the slots. As such, there is little or no relative angular movement between the drive shaft 652 and the coaxial stem. Rotation of the drive shaft 652, induced by the motor 546 is imparted to the stem via abutting engagement between drive pin and the sides of slots). The operative attachment of the spindle 820 with the drive shaft 652 (in this example the engagement between slots and drive pin) retains the spindle 820 to the drive shaft 652 and transfers torque therebetween. As such, the spindle 820 rotates in unison with the drive shaft 652 to power the removal element 568.

Figure 33:
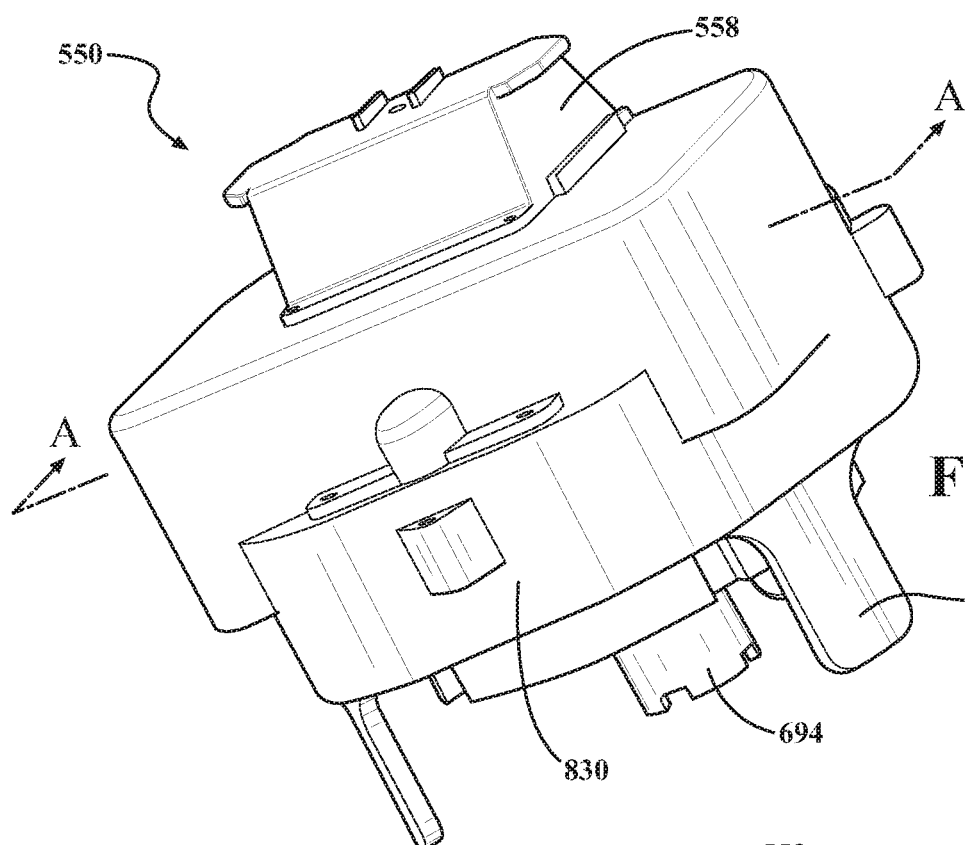
FIG. 33 is a top perspective view of the detached preparation module of the system of FIG. 31.
Figure 34:
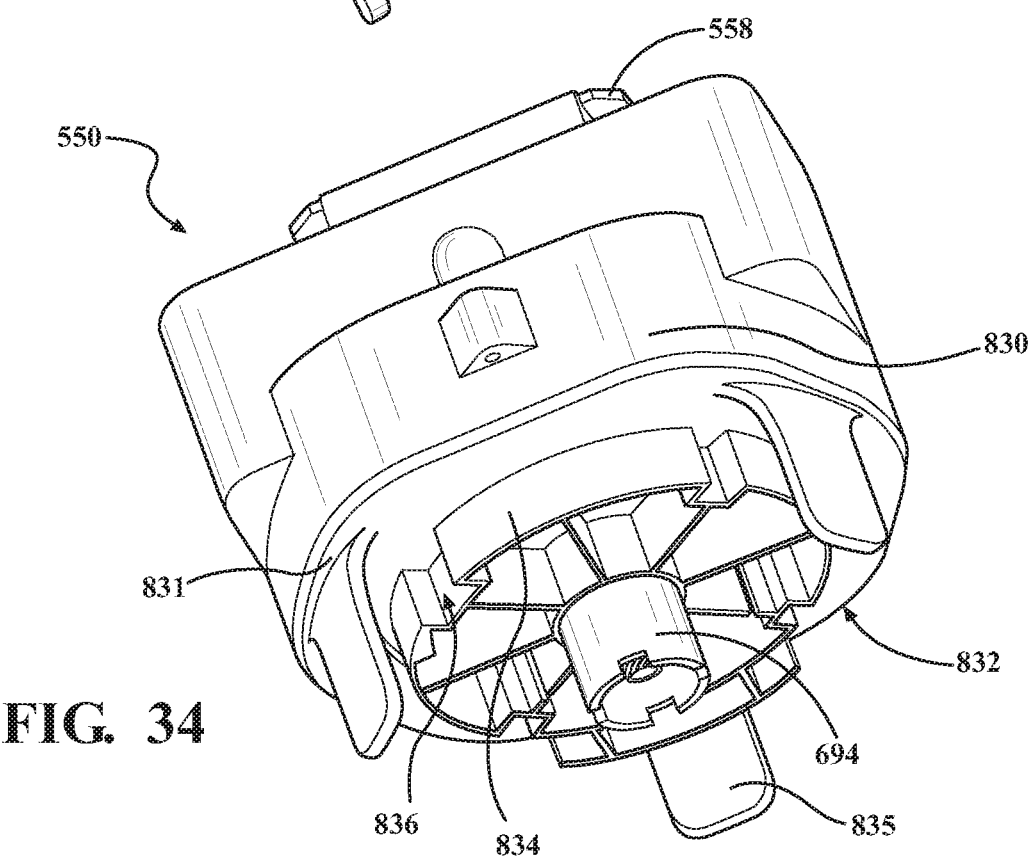
FIG. 34 is a bottom perspective view of the preparation module of FIG. 31.
Figure 35:
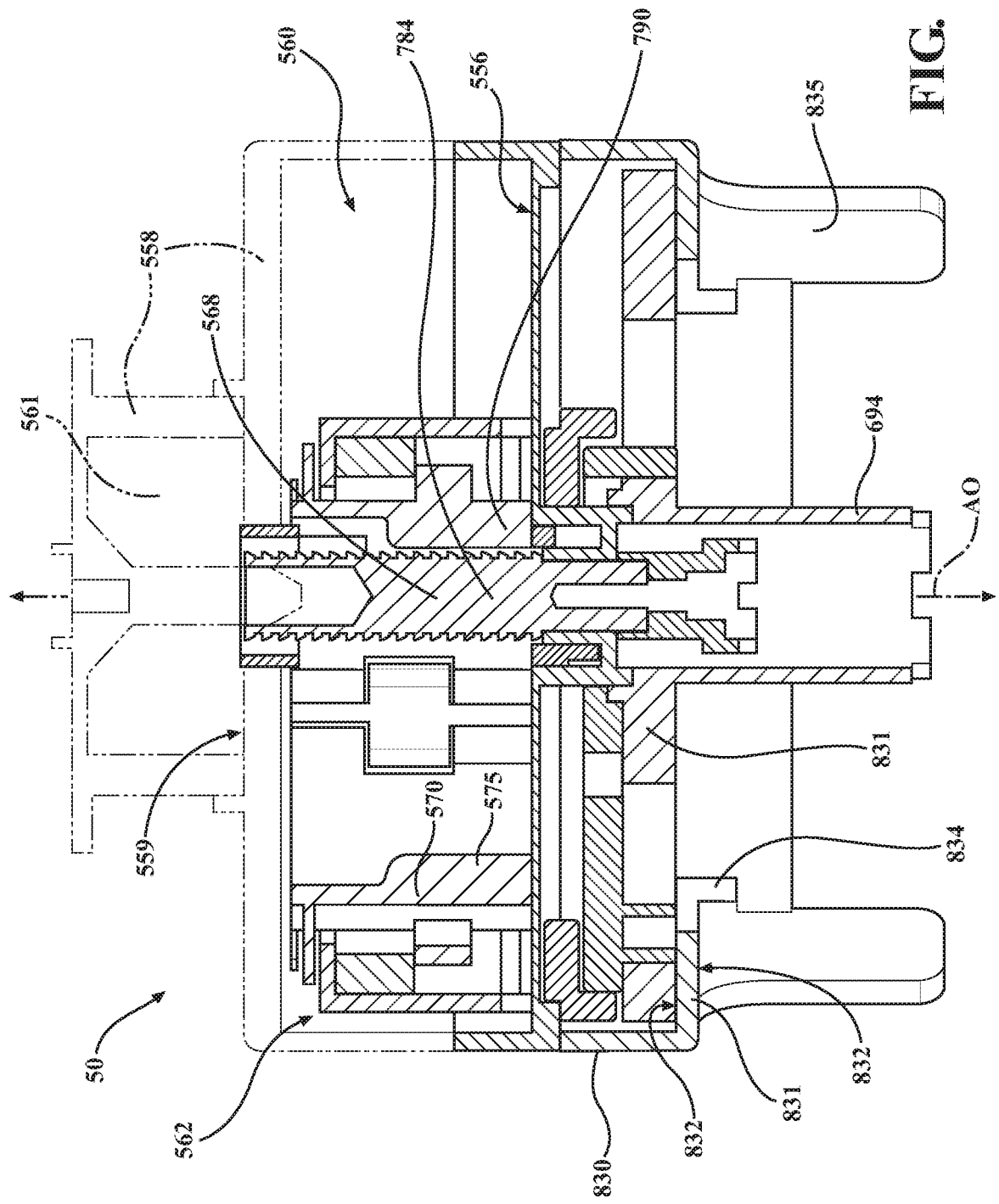
FIG. 35 is a cross-sectional view of the preparation module of FIG. 33 taken along line A-A.

The preparation module 550 of this example is illustrated in FIGS. 33-37. In FIG. 33, a top perspective view of the detached preparation module 550 is illustrated. In FIG. 34, a bottom perspective view of the preparation module 50 is illustrated. In FIG. 35, a cross-sectional view of the preparation module 50 of FIG. 33 taken along line A-A is illustrated.

Referring now to FIGS. 33-35, the preparation module 550 of this example includes a lower shell 830 which is configured to attach to the pedestal 598 and which houses the cam assembly. The lower shell 830 is dimensioned to fit to the base module 544 so that the motor 546, when actuated, drives the cam assembly linearly across a support surface 556. Referring to 34 and 35, the lower shell 830 has a foundation plate 831 with a bottom surface 832 and an outer wall 834. The bottom surface 832 of the foundation plate 831 has three legs 835, which allow the preparation module 550 of this example to be set on a flat surface when detached from the base module 544. The outer wall 834 has an outer periphery that allows the shell 830 to be slip fitted into the mounting space 804 above the mounting surface 800 and within the lip 802.

Referring now to FIG. 34, four circumferentially and equiangularly spaced apart notches 836 extend radially inward in and axially upward from, a downwardly directed face of the outer wall 834. The notches 836 are dimensioned so that when the preparation module 550 is fitted to the base module 544, the pedestal teeth 810 are seated in the notches 836. The engagement of the teeth 810 and notches 836 prevent unwanted rotation of the shell 830 relative to the base module 544 during operation.

The outer wall 834 is further provided with two additional side notches (not shown) that are diametrically opposed from each other. The side notches (not shown in the Figs.) extend radially inwardly from an outer cylindrical surface of the outer wall 834 at a location above a bottom of the outer wall 834. More particularly, the lower shell 830 is formed so that when the lower shell 830 is seated in the mounting space 804 and the pedestal teeth 810 are seated in notches, the side notches are positioned to receive the radially inwardly directed fingers 814 of retention arms 812.

Referring now to FIG. 32, the fingers 814 are biased radially inwardly to seat against cooperating surfaces of the side notches to selectively lock the preparation module 550 via the lower shell 830 to the base module 544. The upper surfaces of fingers 814 may be downwardly angled radially inwardly. This allows the shell 830 to slideably engage and move the fingers 814 radially outward against the biasing force acting on retention arms 812. Thus, the lower shell 830 may be pushed downwardly past the fingers 814 and received in the mounting space 804 without levers 816 being manually actuated.

Referring to FIGS. 33 and 34, the outer wall 834 of the lower shell 830 further includes a foundation plate 831. The foundation plate 831 is fixed to the outer wall 834 by fasteners, ultrasonic welding, or adhesive. The foundation plate 831 is integral with the outer wall 834. The outer wall 834 extends upwardly from the foundation plate 831 and, with a base 554, defines a cavity 844 in which the cam assembly and other portions of the drive train are housed. The foundation also includes a mounting key 694 (also shown in FIG. 35) which houses the collar 672, which is configured to releasably connect to the cam carrier 670 to power the cam assembly and ultimately move the carriage 562 across the support surface 556 of the base 554, and also houses the spindle head 820 which is configured to releasably connect to the base of the removal element 568 and ultimately move the removal element 568 rotationally.

Figure 36:
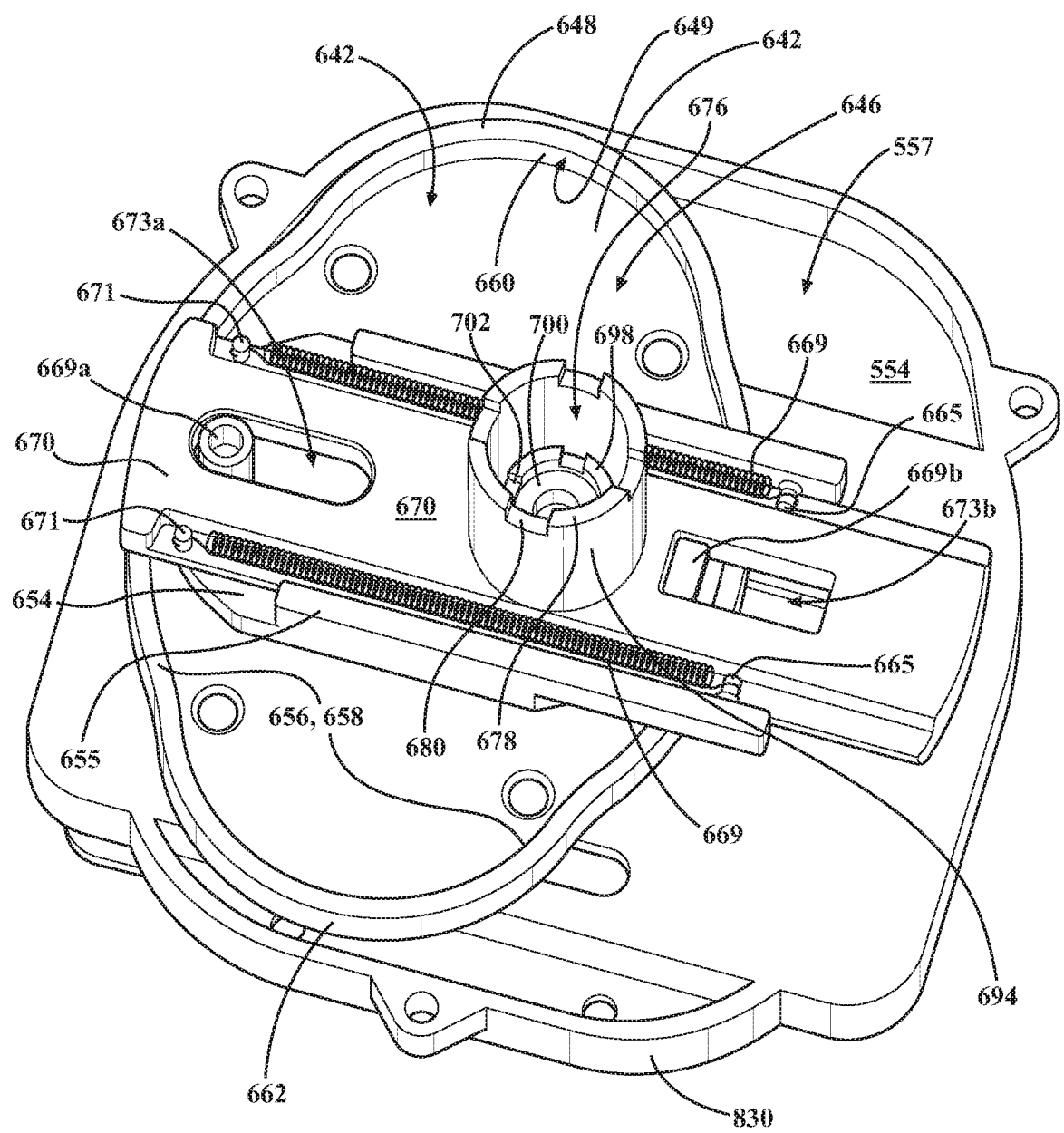
FIG. 36 is an isolated perspective bottom view of the cam assembly of the preparation module of the system of FIG. 31.

Referring now to FIG. 36, just below an outer surface 557 of the base 554 is the cam follower 642, which is moveably mounted on the cam 654 and includes a drive slot 650 in which elements of the drive train 548 are moveably disposed around the operational axis AO. The upper-surface of the cam follower 642 is offset (not disposed on the outer surface 557 of the base 554). In FIG. 36, the cam carrier 670 includes two cam carrier spring posts 671, and the walls of a cam slide 655 include two cam spring posts 665. Two springs 669 connect the two cam carrier spring posts 671 to the respective two cam spring posts 665. The cam slide 655 comprising two sidewalls straddles and slides along the cam carrier 670. Two pegs 667a, and 667b on the cam 654 cooperate with two slots 669a and 669b on the cam carrier 670 to guide movement of the cam 654 on the cam carrier 670. As such, when the carriage 562 stops moving, e.g. due to jammed bone stock, the cam 654 slides back on the cam carrier 670 guided by its cam slide 655 and then springs back into place when the jammed bone stock within the preparation chamber 566 of the carriage 562 breaks up due to the articulating wall 570. This allows for the carriage 562 to stop moving when bone stock jams between the removal element 568 and the wall 564 within the preparation chamber 566 while the drive train 548 and cam assembly continue to operate. As such, jamming of the assembly 540 is prevented.

The cam assembly of this example, which is just as described previously in FIGS. 1-28, is illustrated in an isolated perspective bottom view in FIG. 36. Of course, the cam assembly ultimately drives the drive module 596 linearly across a support surface 556 of the base 554, which provides synergistic interaction between a plurality of articulating wall segments 570 and the removal element 568 to optimize preparing of bone stock in the preparation chamber 566.

Referring to FIGS. 35 and 36, the cam assembly drives the carriage 562 and includes the cam follower 642, the cam 654, and the cam carrier 670. The cam 654 is coupled to the cam carrier 670, which is coupled to the collar 672. The cam 654 is also disposed adjacent the lower surface 646 of the cam follower 642 on the oblong track 648. The oblong track 648 comprises two elongated segments 656, 658 opposite one another and two circular segments 660, 662 opposite one another and also defines an inner surface 649. That is, the elongated 656, 658 and rounded segments 660, 662 of the oblong track 648 alternate. The cam 654 is configured to cooperate with the inner surface 649 of the oblong track 648 to transfer rotary power from the drive train 548 to cause linear movement of the cam follower 642 and cause the corresponding linear movement of the carriage 562 across the support surface 556 of the base 554 via the movement of the drive elements 582 which are disposed in sleeves 584 of the carriage 562.

Referring still to FIGS. 31, 35, and 36, a collar 672 moves rotationally about the operational axis AO and transfers power from the gear assembly, which is operably attached to the drive shaft 652, cooperates with the cam follower 642 to transfer rotational movement of the drive shaft 652 into liner movement of the drive elements 582 via the cam assembly. The collar 672 includes an upper surface 682 having a centrally located drive shaft opening and a plurality of circumferentially and equiangularly spaced apart drive teeth 686. The plurality of drive teeth 686 on the collar 672 engage a plurality of slots 680 in a bottom surface 678 of the cam carrier 670. The plurality of slots 680 are circumferentially and equiangularly spaced apart around the central drive opening 676 of the cam carrier 670. The plurality of slots 680 mate with the plurality of drive teeth 686. The walls of each drive tooth slot 680 are parallel to the respectively interfacing surfaces of each drive tooth 686 and slideably received therein. The collar 672 may be spring-loaded and thus define clutch for transferring torque from the drive shaft 652 to the cam assembly when the plurality of teeth 686 on the collar 672 are received in the plurality of slots 680 on the cam carrier 670.

For the sake of brevity, the description of the movement of the cam assembly is not repeated and additional details regarding the movement of the cam assembly may be found in the description above and FIGS. 1-28.

Figure 37:
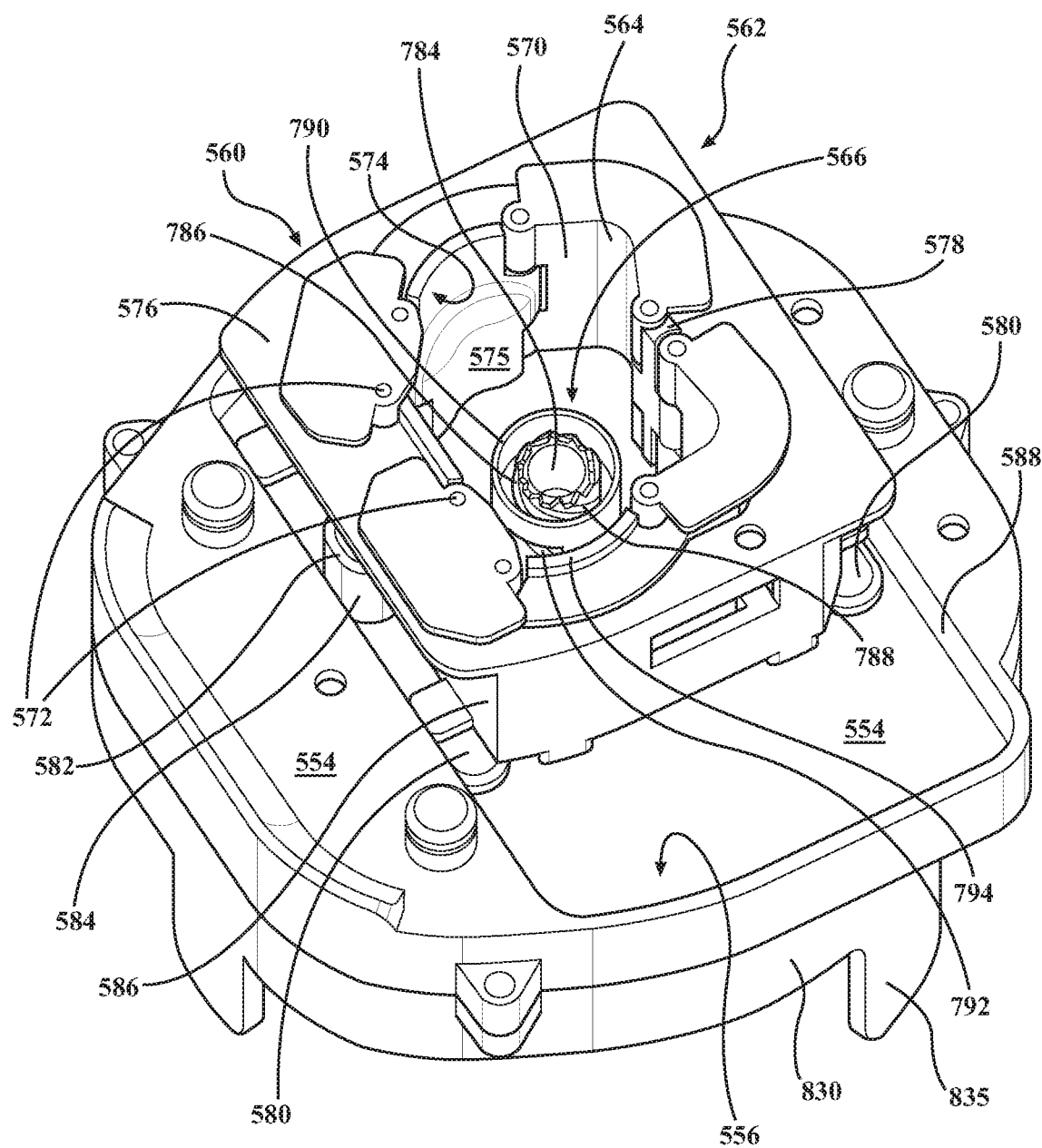
FIG. 37 is a top perspective view of the preparation module of FIG. 33 with a lid removed.

FIG. 37 is a top perspective view of the preparation module 550 with the lid 558 removed. In FIG. 37, the wall 564 surrounds the removal element 568. The wall 564 of FIG. 37 includes a plurality of wall segments 570, which are connected. Many of the wall segments 570 are configured to articulate and may be referred to as articulating wall segments 570. In the example set forth in FIG. 37, the plurality of wall segments 570 are moveably connected via a plurality of hinges 572. Some of the wall segments 570 have a curved interior surface or a profiled interior surface. Two of the wall segments 570 have catch pads 575 disposed on their interior surface 574.

Referring still to FIG. 37, the removal element 568 includes a fluted screw 784 rotationally mounted within the preparation chamber 566 and a shaving tube 790 statically disposed about fluted screw 784 mounted to the base 554. The removal element 568 is illustrated located within the preparation chamber 566. The removal element 568 is supported to rotate about an operational axis AO. The removal element 568 illustrated includes the fluted screw 784 with helical flutes 786 having cutting edges 788. During operation of the system 542, the fluted screw 784 rotates about the operational axis AO and the cutting edges 788 clean bone stock in the preparation chamber 566 by cutting soft tissue from the bone stock. More specifically, the shaving tube 790 defines at least one cutter window 792 through which tissue attached to the bone stock is received for engagement by fluted screw 784. The cutter window 792 is bounded by shaver edges 794. The shaver edges 794 are sharp to cut soft tissue caught between the cutting edges 788 of the helical flutes 786 and the shaver edges 794 of the cutter window 792 when the fluted screw 784 rotates relative to the shaving tube 790. The shaver edges 794 also act as impingement structures against which soft tissue abuts and is temporarily held to facilitate cutting by the fluted screw 784 of the removal element 568.

Referring back to FIG. 36, the fluted screw 784 includes a foundation 698 having a lower surface defining a centrally located opening 700 and a plurality of circumferentially and equiangularly spaced apart notches 702 distributed about the perimeter of the foundation 698. The opening 700 engages the alignment pin 822 of the spindle head 820 coaxially along the operational axis AO while the four circumferentially and equiangularly spaced apart drive teeth 824 that extend upwardly from the planar top surface of the spindle head 820 engage the notches 702 on the foundation 698 of the fluted screw 784. As such, the spindle head 820 transfers rotational energy from the drive shaft 652 to the removal element 568.

Because of the helical geometry of the flutes 786, as the fluted screw 784 rotates, soft tissue is cut, augured axially upwardly along the fluted screw 784 between the fluted screw 784 and the shaving tube 790, and is expelled out of a top end of the shaving tube 790. In essence, the fluted screw 784 acts as a screw conveyor. The space between the fluted screw 784 and the shaving tube 790 is a debris passage through which the cut soft tissue is augured and ultimately expelled.

The lid 558 (removed in FIG. 37, but illustrated in FIGS. 33, 34, and 35) is disposed about the shaving tube 790 near the top end. Referring back to FIG. 35, the lid 558 defines a collecting surface 559 onto which the tissue that exits from the top end of the shaving tube 790 may fall and collect within a collection chamber 561, which is also defined within the lid 558. The collecting surface 559 is spaced slightly below the top end of the shaving tube 790 to act as a soft tissue catch.

Referring to FIG. 37, the carriage 562 typically includes a carriage housing 576 that is spaced outwardly of and coupled to the wall 564, which is resiliently deformable or articulating. The carriage housing 576 extends at least partially around an outer perimeter of the wall 564 and is moveable across the support surface 556 of the base 554. The carriage housing 576 typically has a fixed profile and is not deformable. The wall 564 is coupled to the carriage housing 576. As a coupling example, the wall 564 is be coupled to the carriage housing 576 with two anchors 578.

The carriage housing 576, is just as described above with respect to the first example. Referring to FIG. 37, the carriage housing 576 extends completely around an outer perimeter of the wall 564 and has a fixed inner profile (generally rectangular as illustrated) and is not deformable, while the wall 564 anchored thereto is resiliently deformable.

The carriage 562 is moveably mounted on the support surface 556 of the base 554 in in the void space 560 that the base 554 and the lid 558 collectively define (as is best illustrated in FIG. 35). Referring to FIG. 37, the base 554 typically includes one or more slots 580 with one or more drive elements 582 movably disposed therein, the one or more drive elements 582 being operatively attached to the drive train via the cam assembly.

Still referring to FIG. 37, the two drive elements 582 cooperate with the two sleeves 584 disposed on an outer surface 586 of the carriage housing 576 of the carriage 562. To this end, the base 554 includes the first and second slots 580 which are parallel, first and second drive elements 580 are respectively disposed in the first and second slots 580. In FIG. 37, only one of the drive elements 582 and one of the sleeves 584 is visible. The drive elements 582 are operatively attached the carriage 562 via insertion into the sleeves 584 thereon. The drive elements 582 are configured to move from a first position to a second position within each of the first and second slots 580 to move the carriage 562 laterally across the support surface 556 of the base 554. Additional explanation regarding movement of the carriage 562 across the support surface 556 is illustrated in the schematic drawings FIGS. 23A-25B.

Still referring to FIG. 37, the preparation module 550 may include two guides 588 in the void space 560, which cooperate with the carriage 562 to guide linear movement of the carriage 562 across the support surface 556 of the base 554. In this example, two guides 588a, 588b are formed into the support surface 556 of the base 554 in the void space (i.e. the support surface 556 is profiled).

Figure 38:
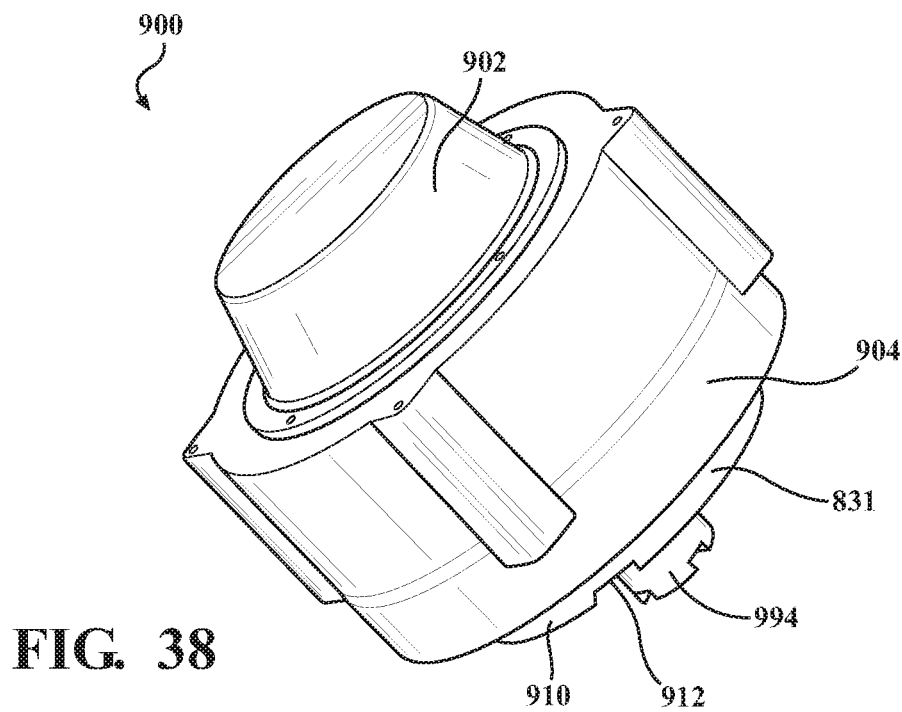
FIG. 38 is a top perspective view of an exemplary alternative detached preparation module for use with the system of FIG. 31.
Figure 39:
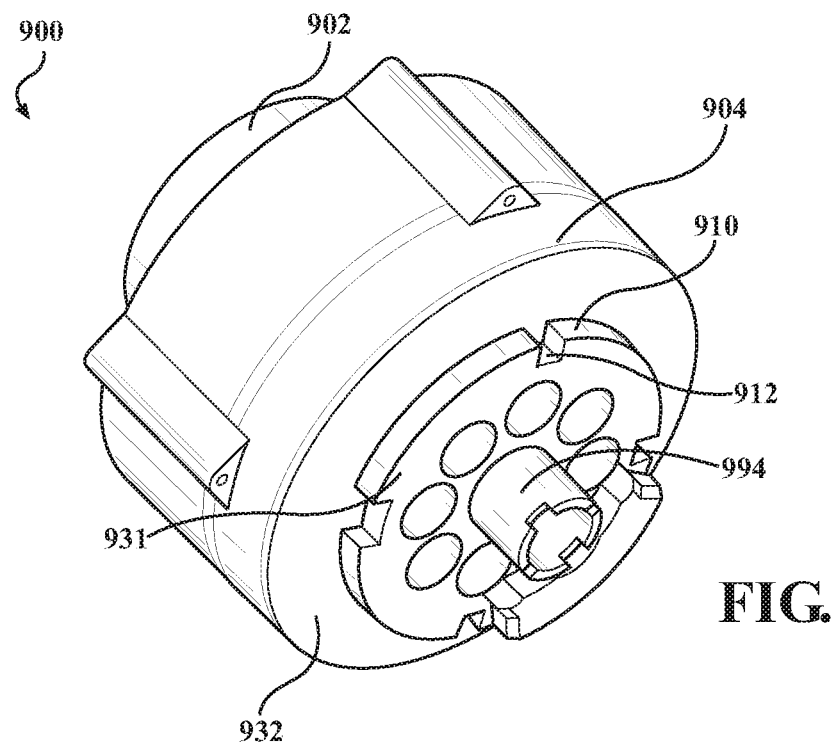
FIG. 39 is a bottom perspective view of the preparation module of FIG. 38.

Referring now to FIGS. 38-41, an alternative example of the preparation module 900 is illustrated. The preparation module 900 includes an alternative example of a cam assembly with a cam 918 having a spring-loaded tip 934 as is described below. The preparation module 900 of FIGS. 38-41 may be used with the base module 544 described in FIGS. 30-32. In FIG. 38, a top perspective view of the detached preparation module 900 is illustrated. In FIG. 39, a bottom perspective view of the preparation module 50 is illustrated.

The preparation module 900 of this example includes the lid 902 and a lower shell 904 which is configured to attach to the pedestal 598 and which houses the cam assembly. The lower shell 904 is dimensioned to fit to the base module 544 so that a motor 546, when actuated, drives the cam assembly linearly across a support surface 556.

Referring now to FIGS. 38 and 39, the lower shell 904 has a foundation plate 931 with the top and the bottom surface 932 and an outer wall 910. The foundation plate 931 also includes a mounting key 994. The outer wall 910 has an outer periphery that allows the shell 904 to be slip fitted into the mounting space 804 above the mounting surface 800 and within the lip 802.

Referring to FIG. 39, four circumferentially and equiangularly spaced apart notches 912 extend radially inward in and axially upward from, a downwardly directed face of the outer wall 910. The notches 912 are dimensioned so that when the shell 904 is fitted to base module 544, the pedestal teeth 810 are seated in the notches 912. The engagement of the teeth 810 and notches 912 prevent unwanted rotation of the shell 904 relative to the base module 544 during operation.

Figure 40:
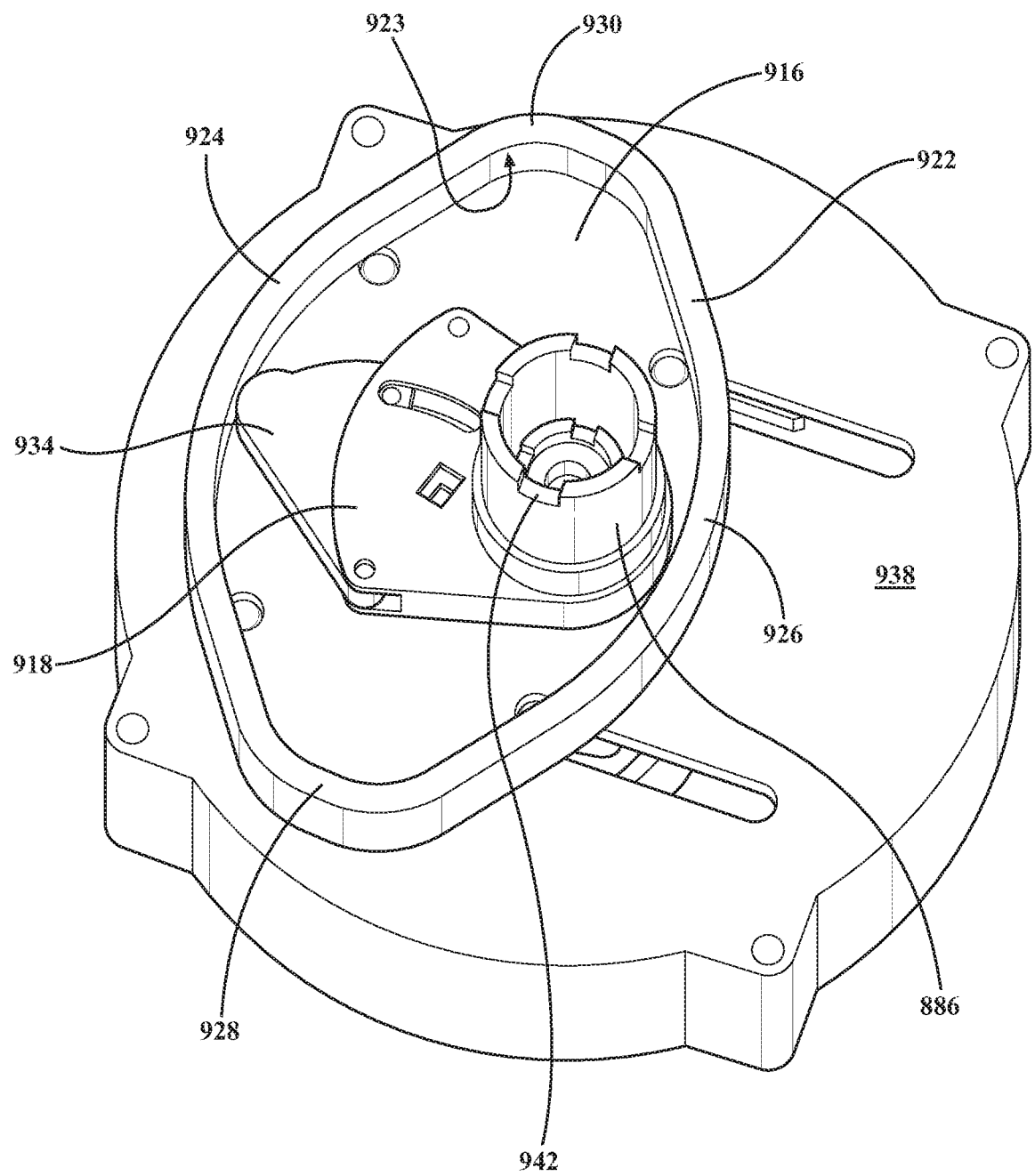
FIG. 40 is an isolated perspective bottom view of the cam assembly of the preparation module of the system of FIG. 38.

The cam assembly of this example is illustrated in an isolated perspective bottom view in FIG. 40. The cam assembly drives the carriage 914 (shown in FIG. 41 but not in FIG. 40) and includes the cam follower 916 and the cam 918. The cam 918 is coupled to the collar 672 of the base module 544. The cam 918 is also disposed adjacent the lower surface of the cam follower 916 in the oblong track 922. The oblong track 922 has two elongated segments 924, 926 opposite one another and two circular segments 928, 930 opposite one another. That is, the elongated 924, 926 and rounded segments 928, 930 of the oblong track 922 alternate. The cam 918 has the spring loaded tip 934 and is configured to cooperate with a surface 923 of the oblong track 922 to transfer rotary power from the drive train 548 to cause linear movement of the cam follower 916 and cause the corresponding linear movement of the carriage 914 across the support surface 936 of the base 938 via the movement of the drive elements which are operatively attached to the carriage 914.

Still referring to FIG. 40, a collar 672 (not shown) moves rotationally about the operational axis AO and transfers power from the gear assembly, which is operably attached to the drive shaft 652 (not shown), cooperates with the cam 918 to transfer rotational movement of the drive shaft 652 into linear movement of the drive elements 582 via the cam assembly. The collar 672 includes an upper surface 682 having a centrally located drive shaft opening 684 and a plurality of circumferentially and equiangularly spaced apart drive teeth 686. The plurality of drive teeth 686 on the collar 672 engage a plurality of slots 942 on the cam 918. The plurality of slots 942 are circumferentially and equiangularly spaced apart around a central drive opening in the cam 918. The plurality of slots 942 mate with the plurality of drive teeth 686.

Figure 41:
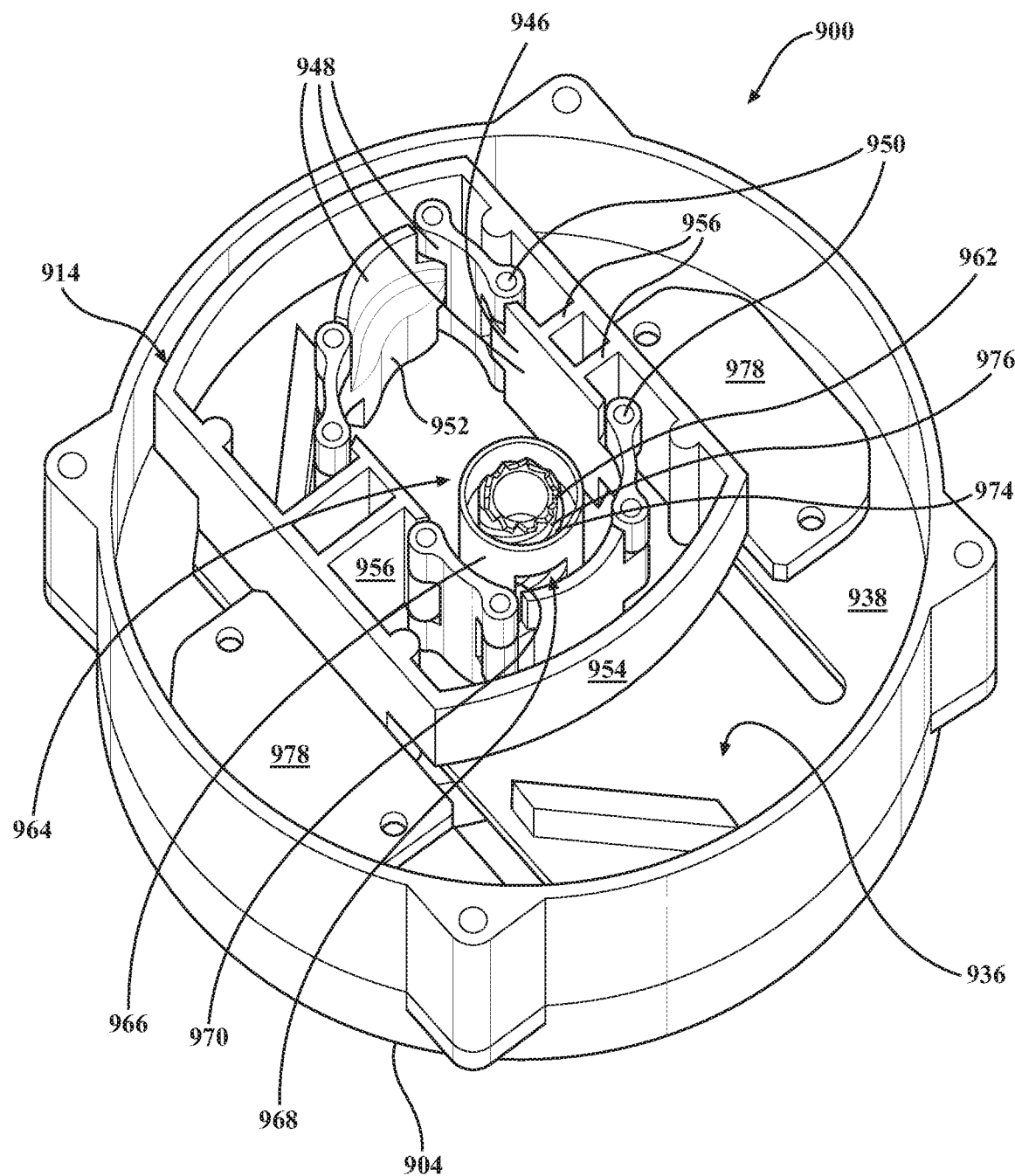
FIG. 41 is a top perspective view of the preparation module of FIG. 38 with a lid removed.

FIG. 41 is a top perspective view of the preparation module 900 with the lid 902 removed. In FIG. 41, the wall 946 surrounds the removal element 960. The wall 946 of FIG. 41 includes a plurality of wall segments 948, which are connected. The wall segments 948 are configured to articulate.

The carriage 914 illustrated in FIG. 41 includes the carriage housing 954, which is positioned radially outward of the outer perimeter of the wall 946. The carriage housing 954 has a fixed inner profile (generally rectangular as illustrated) and is not deformable, while the wall 946 anchored thereto is resiliently deformable. In FIG. 41, two guides 978, which cooperate with the carriage 914 to guide linear movement of the carriage 914 across the support surface 936 of the base 938.

In the example set forth in FIG. 41, the plurality of wall segments 948 are moveably connected via a plurality of hinges 950. Two of the wall segments 948 have catch pads 952 disposed on their interior surface. Further, the wall 946 of FIG. 41 includes two fixed wall segments 948, which are connected to the carriage housing 954 with anchors 956. This example also includes six wall segments 948, which are not anchored to the carriage housing 954, two of which are profiled and include a catch pad 952. The catch pads 952 catch and push the bone stock into the removal element 944, cause deformation of the wall 946, and facilitate movement of the bone stock within the preparation chamber 66 and ensures and removal of ligaments and other soft tissue from the bone stock.

In FIG. 41, the removal element 960 includes a fluted screw 962 rotationally mounted within the preparation chamber 964 and a shaving tube 966 statically disposed about fluted screw 962 mounted to the base 554. The removal element 960 illustrated includes the fluted screw 962 with helical flutes 974 having cutting edges 976. The fluted screw 962 is supported to rotate about an operational axis AO. The shaving tube 966 defines at least one cutter window 968 through which tissue attached to the bone stock is received for engagement by fluted screw 962. The cutter window 968 is bounded by shaver edges 970. The function of the removal element 960 is described in further detail above.

Figure 42:
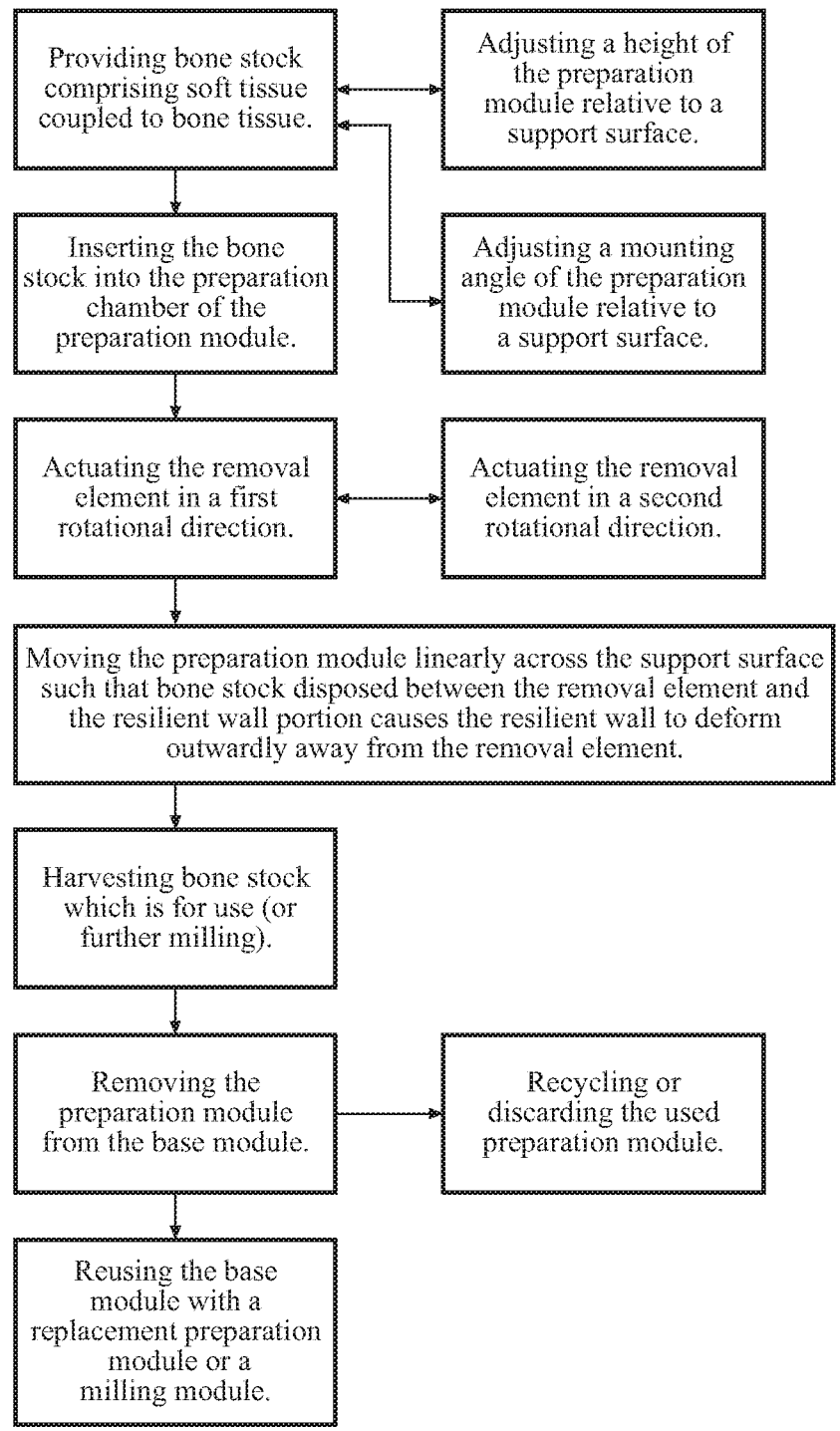
FIG. 42 is a flow chart highlighting steps utilized in an example method of preparing bone stock with the system described herein.

The subject disclosure also includes a method of preparing bone stock with the system 42. Generally speaking, harvested bone stock is placed in the preparation module 50. The motor 46 is actuated to result in an actuation of the carriage 62 and removal element 68. The action of the removal element 68 cuts the soft tissue and other debris from bone stock while leaving a progenitor layer around the bone in place. FIG. 42 is a flow diagram highlighting steps utilized in a non-limiting example method of preparing bone stock for use with the system 42 described herein.

The method includes the steps of: providing bone stock comprising soft tissue coupled to bone tissue; inserting the bone stock into the preparation chamber 66 of the carriage 62; actuating the removal element 68; and moving the carriage 62 across the support surface 56 such that bone stock disposed between the removal element 68 and the resilient wall portion causes the wall 64 to deform outwardly away from the removal element 68. Alternatively, or in addition to the moving step described above, the method may include moving the carriage 62 across the support surface 56 such that a portion of the wall 64 articulates, i.e., at least one segment of the wall articulates relative to another wall segment.

In some examples, the base module 44 is connected to a power supply. In other battery-powered examples, the method may require the step of charging the battery prior to use and then powering the system 42 on.

The system 42 of this disclosure is prepared for use by attaching the preparation module 50 to the base module 44. Prior to use, the height of the preparation module 50, relative to the mounting surface 106 that the system 42 is placed on, may be adjusted by slideably engaging upper and lower leg components 120, 118 as desired by a user for ergonomic and other reasons. Further, a user may adjust an angle at which the preparation module 50 is mounted on the base module 44 for optimal performance and/or user ergonomics. Once adjusted to a desired angle relative to the mounting surface 106, the bone stock is gravity fed across the inclined support surface 56 to facilitate contact with the removal element 68.

Once these steps are completed, push button 230 or other control element is depressed to actuate the system 42. The step of actuating the removal element 68 may be further defined as actuating the removal element 68 in a first rotational direction while concurrently moving the carriage 62 across the support surface 56 of the base 54. The drive train, including the cam assembly, allows for an additional step of actuating the removal element 68 in a second rotational direction, opposite the first rotational direction, while concurrently moving the carriage 62 across the support surface 56 of the base 54.

Once the bone stock is prepared and removed from the preparation module 50 for further use, e.g. milling, the preparation module 50 may be released from the base module 44. Once removed, the preparation module 50 may then be disposed or recycled. Otherwise, once removed, soft tissue may be removed from the preparation module 50 and the used preparation module 50 may be autoclaved for further use. Of course, a new preparation module 50 or a milling module may then be used with the base module 44 as needed.

Additional Formatted Disclosure: Assembly with Articulating Wall Segments

I. An assembly for preparing bone stock, said assembly including:
  a shell comprising a base having a support surface and an outer surface opposite said support surface, and a lid, said base and lid having a void space therebetween;
  a carriage disposed at least partially within said void space, and moveable across said support surface of said base, said carriage comprising a wall, said wall comprising a plurality of articulating wall segments, said wall cooperating with said support surface of said base to define a preparation chamber; and
  a removal element disposed at least partially in said preparation chamber, said removal element configured to prepare bone stock by removing soft tissue from said bone stock; and
  wherein said carriage is configured to receive power from a drive train to actuate linear movement of said carriage across said support surface, and said removal element is also configured to receive power from said drive train;
  wherein said plurality of articulating wall segments are configured to articulate relative to one another when bone stock is positioned between said removal element and said wall.

II. The assembly as set forth I. wherein said plurality of articulating wall segments are connected with a plurality of hinges.

III. The assembly as set forth in I. or II. wherein one or more of said plurality of articulating wall segments present a curved interior surface.

IV. The assembly as set forth in any one of I. through III. wherein said carriage further comprises a carriage housing spaced outwardly of and coupled to said wall, wherein said carriage housing extends at least partially around an outer perimeter of said wall and is moveable across said support surface of said base.

V. The assembly as set forth in IV. wherein said wall is coupled to said carriage housing with one or more anchors.

VI. The assembly as set forth in V. wherein said one or more anchors comprise an elastomer or a spring.

VII. The assembly as set forth in V. wherein at least one of said one or more anchors include a spring.

VIII. The assembly as set forth in any one of I. through VII. wherein said wall comprises at least six hinged wall segments, wherein at least two of said at least six wall segments are connected to said carriage housing with two of said one or more anchors.

IX. The assembly as set forth in any one of I. through VIII. wherein said carriage is moveably mounted in said void space on said support surface of said base.

X. The assembly as set forth in any one of I. through IX. wherein said base includes one or more slots with a drive element movably disposed therein, said drive element being operatively attached to said drive train.

XI. The assembly as set forth in any one of I. through X. wherein said base includes a first slot and a second slot parallel to said first slot, wherein a drive element is operatively attached to both said carriage and said drive train and is configured to move from a first position to a second position within each of said first and second slots to move said carriage laterally across said support surface of said base.

XII. The assembly as set forth in any one of I. through XI. wherein said base includes one or more guides mounted on said support surface in said void space which cooperate with an exterior of said carriage to guide linear movement of said carriage across said support surface of said base.

XIII. The assembly as set forth in any one of I. through XII. wherein said drive train is operably coupled to said carriage and configured to transfer rotary power from said drive train to cause linear movement of said carriage across said support surface of said base, and said drive train is operably coupled to said removal element and is configured to cause rotational movement of said removal element, wherein upon actuation of said drive train said carriage moves laterally across said support surface of said base and said removal element moves rotationally in said preparation chamber.

XIV. The assembly as set forth in XIII wherein said drive train is configured to cause rotational movement of said removal element in a forward movement (e.g. clockwise) and a reverse movement (e.g. counter-clockwise), opposite said forward movement, and concurrently cause linear movement of said carriage laterally across said support surface of said base.

XV. The assembly as set forth in any one of I. through XIV. wherein said drive train further comprises:
a cam follower having an upper surface, a lower surface having a track thereon with an oblong profile, and a drive slot, wherein said upper surface of said cam follower is adjacent said outer surface of said base such that said cam follower is opposite said carriage, and moveable across said outer surface of said base of said shell; and
a cam rotationally coupled to said drive train and disposed on and/or in said oblong track, said cam configured to cooperate with said oblong track and said drive slot to transfer rotary power from said drive train to cause linear movement of said cam follower across the outer surface of said base and cause the corresponding linear movement of said carriage across said support surface of said base.

XVI. The assembly as set forth in XV. wherein said cam has a spring-loaded tip that abuts an inner surface of said oblong track.

XVII. The assembly as set forth in any one of I. through XVI. wherein said removal element is rotatably mounted to said shell.

XVIII. The assembly as set forth in any one of I. through XVII. wherein said removal element is selected from: a rotating brush; a rotating grater; and a rotating fluted screw.

XIX. The assembly as set forth in any one of I. through XVIII. wherein said removal element comprises a rotating fluted screw and a windowed shaving tube, wherein said windowed shaving tube is adjacent said fluted screw and is statically mounted to said shell.

XX. The assembly as set forth in any one of I. through XIX. wherein said support surface is inclined so that gravity funnels said bone stock in said preparation chamber towards a chamber location that facilitates contact with said removal element.

Additional Formatted Disclosure: Assembly (Modular System)

I. A modular bone preparation system, the system comprising:
a base module including a motor and a drive train; and
a preparation module adapted for releasable attachment to the base module, the preparation module comprising:
a shell comprising a base having a support surface and an outer surface opposite said support surface, and a lid having a void space therebetween;
a carriage disposed at least partially within said void space and moveable across the base of the shell, the carriage comprising a wall, at least a portion of the wall being resiliently deformable, the wall cooperating with said base to define a preparation chamber;
a removal element disposed at least partially in the preparation chamber, the removal element configured to prepare the bone stock by removing soft tissue from the bone stock; and
the drive train being operably coupled to the carriage such that rotary power transferred from the drive train to move the carriage linearly across the base upon actuation of the drive train; the drive train also being operably coupled to the removal element to cause rotational movement of the removal element upon actuation of the drive train.

II. The system as set forth in I. wherein said at least a portion of the wall comprises a plurality of articulating wall segments.

III. The system as set forth in II. wherein the plurality of articulating wall segments are hinged.

IV. The system as set forth in II. or III. wherein the base includes one or more slots with a drive element disposed therein, the drive element being movably disposed in the one or more slots and operatively attached to the drive train.

V. The system as set forth in any one of I. through IV. wherein the base includes a first slot and a second slot parallel to the first slot and having the drive element disposed therein, wherein the drive element is operatively attached to both the carriage and the drive train and is configured to move from a first position to a second position within each of the first and second slots to move the carriage linearly across the support surface of the base.

VI. The system as set forth in any one of I. through V. wherein the drive train is operably coupled to said carriage and configured to transfer rotary power from the drive train to cause linear movement of the carriage across the support surface of the base, and the drive train is operably coupled to the removal element and is configured to cause rotational movement of the removal element, wherein upon actuation of the drive train the carriage moves linearly across the support surface of the base and the removal element moves rotationally in the preparation chamber.

VIII. The system as set forth in VII. wherein the drive train is configured to cause rotational movement of the removal element in a first direction (e.g. clockwise) and a second direction (e.g. counter-clockwise), opposite the first direction, and concurrently cause linear movement of the carriage across the support surface of the base.

IX. The system as set forth in any one of I. through VII. wherein the drive train further comprises:
a cam follower having an upper surface, a lower surface having a track thereon with an oblong profile, and a drive slot, wherein the upper surface of the cam follower is adjacent the outer surface of the base such that the cam follower is opposite the carriage, and moveable across the outer surface of the base of the shell; and
a cam rotationally coupled to the drive train and disposed in the oblong track, the cam configured to cooperate with the oblong track and the drive slot to transfer rotary power from the drive train to cause linear movement of the cam follower across the outer surface of the base and cause corresponding linear movement of the carriage across the support surface of the base.

X. The system as set forth in IX. wherein the cam follower and the cam are present in the preparation module.

XI. The system as set forth in IX. wherein the cam follower and the cam are present in the base module.

Additional Formatted Disclosure: Assembly (Method)

I. A method of preparing bone stock with a preparation module including a shell having a base with a support surface and defining a void space, a carriage at least partially disposed in the void space and comprising a resilient wall including a resilient portion which cooperates with the base to define a preparation chamber, and a removal element disposed within the preparation chamber, the method comprising the steps of:
providing bone stock comprising soft tissue coupled to bone tissue;
inserting the bone stock into the preparation chamber of the carriage;
actuating the removal element; and
moving the carriage across the support surface such that bone stock disposed between the removal element and the resilient portion causes the resilient wall to deform outwardly away from the removal element.

II. The method of preparing bone stock as set forth in I. further comprising the step of attaching the preparation module to a base module.

III. The method of preparing bone stock as set forth in II. further comprising the step of releasing the preparation module from the base module.

IV. The method of preparing bone stock as set forth in any one of I. through III. further comprising the step of disposing the preparation module.

V. The method of preparing bone stock as set forth in any one of I. through IV. wherein the step of actuating the removal element is further defined as actuating the removal element in a first rotational direction while concurrently moving the carriage across the support surface of the base.

VI. The method of preparing bone stock as set forth in V. further comprising the step of actuating the removal element in a second rotational direction, opposite the first rotational direction, while concurrently moving the carriage across the support surface.

VII. The method of preparing bone stock as set forth in any one of I. through VI. further comprising the step of gravity feeding the bone stock across the support surface, the support surface having an incline, to facilitate contact with the removal element.

It will be appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several examples have been discussed in the foregoing description. However, the examples discussed herein are not intended to be exhaustive or limit the device to any particular form. The terminology which has been used is intended to be in the nature of words of description rather than of limitation. Many modifications and variations are possible in light of the above teachings and the device may be practiced otherwise than as specifically described.

Accordingly, it is an object of the appended claims to cover all such variations and modifications that come within the true spirit and scope of this disclosure.

What is claimed is:

1. An assembly for preparing bone stock, said assembly including:
a shell comprising a base having a support surface and an outer surface opposite said support surface, and a lid having a void space therebetween;
a carriage disposed at least partially within said void space and moveable across said base of said shell, said carriage comprising a wall, at least a portion of said wall being resiliently deformable, said wall cooperating with said base to define a preparation chamber; and
a removal element disposed at least partially in said preparation chamber, said removal element configured to prepare said bone stock by removing soft tissue from said bone stock; and
wherein said carriage is configured to receive power from a drive train to actuate movement of said carriage across said support surface, and said removal element is also configured to receive power from said drive train; and
wherein said portion of said wall that is resiliently deformable is configured to deform when bone stock is positioned between said removal element and said wall.

2. The assembly as set forth claim 1, wherein said at least a portion of said wall comprises a plurality of articulating wall segments.

3. The assembly as set forth in claim 2, wherein said plurality of articulating wall segments are hinged.

4. The assembly as set forth in claim 2, wherein one or more of said plurality of articulating wall segments present a curved interior surface.

5. The assembly as set forth in claim 1, wherein said at least a portion of said wall comprises an elastomer.

6. The assembly as set forth in claim 1, wherein said carriage further comprises a carriage housing spaced outwardly of and coupled to said wall, wherein said carriage housing extends at least partially around an outer perimeter of said wall and is moveable across said support surface of said base.

7. The assembly as set forth in claim 6, wherein said wall is coupled to said carriage housing with one or more anchors.

8. The assembly as set forth in claim 7, wherein said one or more anchors comprise: an elastomer; and/or a spring.

9. The assembly as set forth in claim 7, wherein said wall comprises at least six hinged wall segments, wherein at least two of said at least six wall segments are connected to said carriage housing with said one or more anchors.

10. The assembly as set forth in claim 1, wherein said carriage is moveably mounted in said void space on said surface of said base.

11. The assembly as set forth in claim 1, wherein said base includes one or more slots with a drive element movably disposed therein, said drive element being operatively attached to said drive train.

12. The assembly as set forth in claim 1, wherein said base includes a first slot and a second slot parallel to said first slot and a drive element respectively disposed therein, wherein said drive element is operatively attached to both said carriage and said drive train and is configured to move from a first position to a second position within each of said first and second slots to move said carriage linearly across said support surface of said base.

13. The assembly as set forth in claim 1, wherein said base includes one or more guides mounted on said support surface in said void space that cooperate with an exterior of said carriage to guide movement of said carriage across said support surface of said base.

14. The assembly as set forth in claim 1, wherein said drive train is operably coupled to said carriage and configured to transfer rotary power from said drive train to cause linear movement of said carriage across said support surface of said base, and said drive train is operably coupled to said removal element and is configured to cause rotational movement of said removal element, wherein upon actuation of said drive train said carriage moves linearly across said support surface of said base and said removal element moves rotationally in said preparation chamber.

15. The assembly as set forth in claim 14, wherein said drive train is configured to cause rotational movement of said removal element in a forward movement (e.g. clockwise) and a reverse movement (e.g. counter-clockwise), opposite said forward movement, and concurrently cause linear movement of said carriage linearly across said support surface of said base.

16. The assembly as set forth in claim 1, wherein said drive train further comprises:
   a cam follower having an upper surface, a lower surface having a track thereon with an oblong profile, and a drive slot, wherein said upper surface of said cam follower is adjacent said outer surface of said base such that said cam follower is opposite said carriage, and moveable across said outer surface of said base of said shell; and
   a cam rotationally coupled to said drive train and disposed in said oblong track, said cam configured to cooperate with said oblong track and said drive slot to transfer rotary power from said drive train to cause linear movement of said cam follower across said outer surface of said base and cause corresponding linear movement of said carriage across said support surface of said base.

17. The assembly as set forth in claim 16, wherein said cam has a spring-loaded tip that abuts an inner surface of said oblong track.

18. The assembly as set forth in claim 1, wherein said removal element is rotatably mounted to said shell.

19. The assembly as set forth in claim 18, wherein said removal element is selected from: a rotating brush; a rotating grater; and a rotating fluted screw.

20. The assembly as set forth in claim 1, wherein said support surface is inclined so that gravity funnels said bone stock in said preparation chamber towards a chamber location that facilitates contact with said removal element.

21. A method of preparing bone stock with a preparation module including a shell having a base with a support surface and defining a void space, a carriage at least partially disposed in the void space and comprising a resilient wall including a resilient portion which cooperates with the base to define a preparation chamber, and a removal element disposed within the preparation chamber, the method comprising the steps of:
   providing bone stock comprising soft tissue coupled to bone tissue;
   inserting the bone stock into the preparation chamber of the carriage;
   actuating the removal element; and
   moving the carriage across the support surface such that bone stock disposed between the removal element and the resilient portion causes the resilient wall to deform outwardly away from the removal element.

22. An assembly for preparing bone stock, said assembly including:
   a shell comprising a base having a support surface and an outer surface opposite said support surface, and a lid, said base and lid having a void space therebetween;
   a carriage disposed at least partially within said void space, and moveable across said support surface of said base, said carriage comprising a wall, said wall comprising a plurality of articulating wall segments, said wall cooperating with said support surface of said base to define a preparation chamber; and
   a removal element disposed at least partially in said preparation chamber, said removal element configured to prepare bone stock by removing soft tissue from said bone stock;
   and wherein said carriage is configured to receive power from a drive train to actuate linear movement of said carriage across said support surface, and said removal element is also configured to receive power from said drive train;
   wherein said plurality of articulating wall segments are configured to articulate relative to one another when bone stock is positioned between said removal element and said wall.

* * * * *